(12) United States Patent
Ishii et al.

(10) Patent No.: US 12,322,094 B2
(45) Date of Patent: Jun. 3, 2025

(54) IMAGE ACQUIRING DEVICE, CANCER DETERMINATION DEVICE, CANCER DETERMINATION METHOD, AND COMPUTER-READABLE MEDIUM

(71) Applicants: OSAKA UNIVERSITY, Osaka (JP); NIKON CORPORATION, Tokyo (JP)

(72) Inventors: Masaru Ishii, Suita (JP); Takahiro Matsui, Suita (JP); Ryo Tamoto, Yokohama (JP); Akio Iwasa, Yokohama (JP); Masafumi Mimura, Ageo (JP)

(73) Assignees: OSAKA UNIVERSITY, Osaka (JP); NIKON CORPORATION, Tokyo (JP)

( * ) Notice: Subject to any disclaimer, the term of this patent is extended or adjusted under 35 U.S.C. 154(b) by 448 days.

(21) Appl. No.: 17/727,218

(22) Filed: Apr. 22, 2022

(65) Prior Publication Data

US 2022/0366561 A1    Nov. 17, 2022

Related U.S. Application Data

(63) Continuation of application No. PCT/JP2020/039977, filed on Oct. 23, 2020.

(30) Foreign Application Priority Data

Oct. 23, 2019  (JP) .................................. 2019-192469
Oct. 23, 2019  (JP) .................................. 2019-192470

(51) Int. Cl.
G06T 7/00      (2017.01)
G01N 21/64     (2006.01)
G01N 33/483    (2006.01)

(52) U.S. Cl.
CPC ....... *G06T 7/0012* (2013.01); *G01N 21/6428* (2013.01); *G01N 21/6486* (2013.01);
(Continued)

(58) Field of Classification Search
USPC .......................................................... 382/170
See application file for complete search history.

(56) References Cited

U.S. PATENT DOCUMENTS 11,010,881 B2 *  5/2021  Toussaint ............. G02B 21/008
11,555,819 B2 *  1/2023  Mizoguchi ............... A61B 1/00
(Continued)

FOREIGN PATENT DOCUMENTS

| CN | 109299679 A | 2/2019 |
| EP | 3459424 A1 | 3/2019 |
| WO | WO 2017/200066 A1 | 11/2017 |

OTHER PUBLICATIONS

Javier Adur et al., "Optical Biomarkers of Serous and Mucinous Human Ovarian Tumor Assessed with Nonlinear Optics Microscopies", Oct. 8, 2012, PLOS ONE, vol. 7, Issue 10, pp. 1-13 (Year: 2012).*
(Continued)

Primary Examiner — Neil R McLean
(74) Attorney, Agent, or Firm — SQUIRE PATTON BOGGS (US) LLP

(57) ABSTRACT

An image acquire device comprising: an irradiator configured to irradiate an undyed tissue with excitation light; an image sensor configured to acquire a third harmonic image of the undyed tissue based on light generated in third harmonic generation caused by interaction between the undyed tissue and the excitation light.

16 Claims, 39 Drawing Sheets

(52) U.S. Cl.
CPC . *G01N 33/4833* (2013.01); *G01N 2021/6439* (2013.01); *G06T 2207/10056* (2013.01); *G06T 2207/20076* (2013.01); *G06T 2207/20081* (2013.01); *G06T 2207/30024* (2013.01); *G06T 2207/30096* (2013.01)

(56) References Cited

U.S. PATENT DOCUMENTS

| | | | | |
|---|---|---|---|---|
| 2017/0053398 | A1* | 2/2017 | Mahoor | G06T 7/42 |
| 2018/0253590 | A1* | 9/2018 | Lloyd | G06V 20/698 |
| 2018/0253845 | A1* | 9/2018 | Liu | G06V 20/698 |
| 2019/0339202 | A1* | 11/2019 | Yamada | G01N 21/6458 |

OTHER PUBLICATIONS

Jian Lin et al., "Study of Acetowhitening Mechanism in Live Mammalian Cells with Label-Free Subcellular-Level Multimodal Nonlinear Optical Microscopy", Mar. 5, 2015, SPIE—International Society for Optical Engineering, vol. 9329, pp. 93290T-1-93290T-6 (Year: 2015).*

Notice of Reasons for Refusal mailed Aug. 6, 2024 for Japanese Patent Application No. 2021-553576; with English translation, 8 pages.

Gavgiotaki, et al., "Non-linear microscopy differentiates normal from pathological breast tissue", Proceedings of SPIE 2018; vol. 10685; pp. 106854I-1 to 106854I-9; doi: 1117/12.2315365.

Van Huizen, et al., "Second and third harmonic generation microscopy visualizes key structural components in fresh unprocessed healthy human breast tissue", Journal of Biophotonics; Jun. 2019; vol. 12, e201800297; pp. 1-11; doi: 10.1002/jbio.201800297.

International Search Report mailed Dec. 8, 2020 for PCT/JP2020/039977, with English translation, 6 pages.

Written Opinion of the International Searching Authority mailed Dec. 8, 2020 for PCT/JP2020/039977, with English translation, 8 pages.

Adur, et al., "Optical Biomarkers of Serous and Mucinous Human Ovarian Tumor Assessed with Nonlinear Optics Microscopies", PLOS ONE; Oct. 8, 2012; vol. 7, Issue 10, e47007.

Ali, et al., "Artificial neural network based screening of cervical cancer using a hierarchical modular neural network architecture (HMNNA) and novel benchmark uterine cervix cancer database", Neural Comput & Applic 2019; vol. 31, pp. 2979-2993.

Ambekar et al., "Quantifying collagen structure in breast biopsies using second-harmonic generation imaging", Biomedical Optics Express 2012; vol. 3(9), pp. 2021-2035.

Gavgiotaki, et al., "Nonlinear imaging of female breast tissue biopsies", Proceedings of SPIE; Jul. 22, 2019; vol. 11076, pp. 110760I-1 -110760I-6, pp. 4-5.

Lin, et al., "Study of acetowhitening mechanisms in live mammalian cells with label-free subcellular-level multimodal nonlinear optical microscopy", Proceeding of SPIE 2015; vol. 9329, pp. 93290T-1-93280T-711076, pp. 110760I-1-110760I-6, pp. 3-11.

Sheikhzadeh, et al., "Confocal Fluorescence Microscopy for Detection of Cervical Preneoplastic Lesions", Proceedings of SPIE 2015, vol. 9420, pp. 942009-1-942009-6; abstract.

Tokarz, et al., "Characterization of Pancreatic Cancer Tissue Using Multiphoton Excitation Fluorescence and Polarization-Sensitive Harmonic generation Microscopy", Frontiers in Oncology; Apr. 17, 2019; vol. 9(272), pp. 1-10.

EPO Communication dated Nov. 23, 2023 forwarding the extended search report for European Patent Application No. 20878152.6; 15 pages.

Communication pursuant to Article 94(3) EPC dated Nov. 13, 2024, forwarding the examination report for European Patent Application No. 20878152.6; 4 pages.

Office Action dated Mar. 12, 2025 for Chinese Patent Application No. 202080089076.X; with English (machine) translation, 20 pages.

* cited by examiner

FIG. 6

| FEATURE AMOUNT | STATISTICAL VALUE | NORMAL (UPPER LAYER) | NORMAL (INTERMEDIATE LAYER) | NORMAL (LOWER LAYER) | CANCER① | CANCER② |
|---|---|---|---|---|---|---|
| AREA | MEDIAN | SMALL | MEDIUM | MEDIUM | LARGE | MEDIUM |
| | MEDIAN ABSOLUTE ERROR | SMALL | SMALL | SMALL | LARGE | LARGE |
| ROUNDNESS | MEDIAN | LARGE | LARGE | LARGE | LARGE | SMALL |
| | MEDIAN ABSOLUTE ERROR | SMALL | SMALL | SMALL | SMALL | LARGE |
| NEAREST DISTANCE | MEDIAN | LARGE | LARGE | MEDIUM | SMALL | MEDIUM |
| | MEDIAN ABSOLUTE ERROR | SMALL | SMALL | SMALL | LARGE | LARGE |
| NUMBER | — | FEW | MEDIUM | MEDIUM | MANY | MEDIUM |

| MEASURED VALUE | DEFINITION |
|---|---|
| AREA | NUMBER OF PIXELS OF CELL NUCLEUS REGION × AREA PER PIXEL ($\mu m^2$) |
| ROUNDNESS | $4\pi \times$ (AREA)/(SQUARE OF CIRCUMFERENCE) [0 – 1.0]<br>UNEVENNESS OF OBJECT IS EASILY REFLECTED IN VALUE<br><br>(MEASUREMENT EXAMPLE)<br><br>0.870  0.820  0.601 |
| NEAREST DISTANCE | EUCLIDEAN DISTANCE FROM CENTER OF GRAVITY OF LABEL TO CENTER OF GRAVITY OF ANOTHER CLOSEST LABEL |

FIG. 19
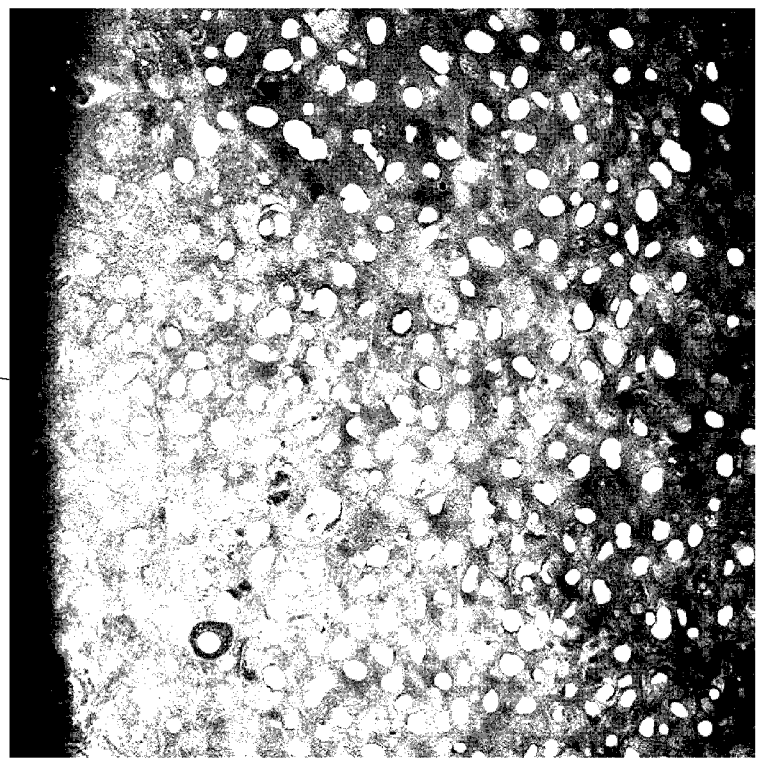
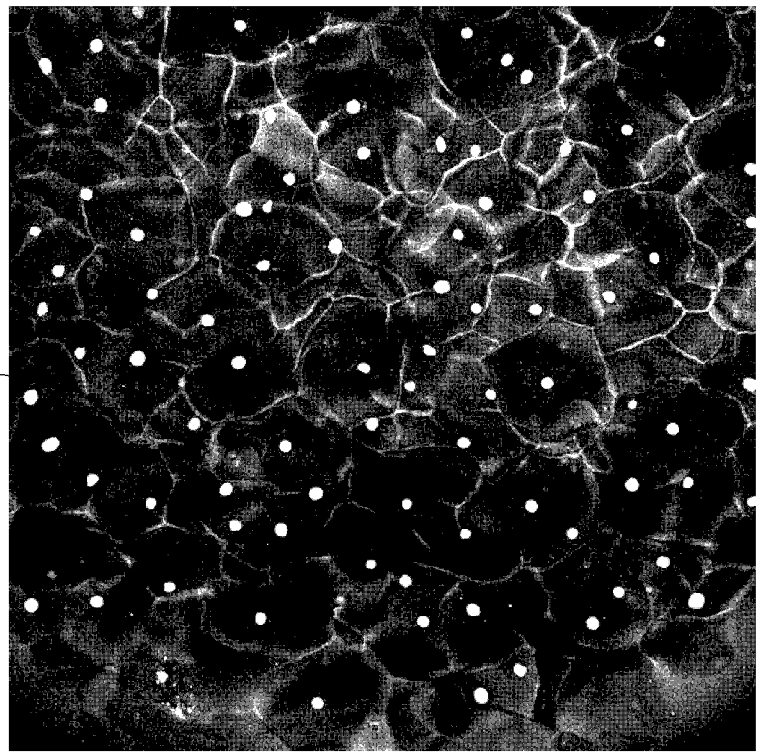

FIG. 27
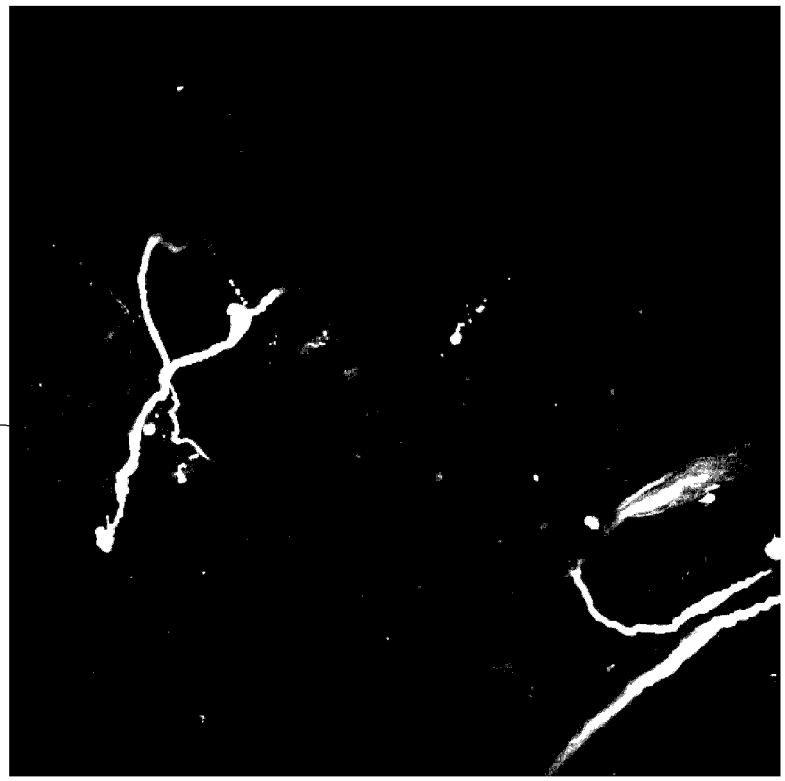

| DETERMINATION THRESHOLD | SENSITIVITY | SPECIFICITY |
|---|---|---|
| 0.0001 | 100.0% | 0.0% |
| 0.0005 | 100.0% | 66.7% |
| 0.001 | 93.8% | 66.7% |
| 0.0025 | 81.3% | 100.0% |
| 0.005 | 62.5% | 100.0% |
| 0.0075 | 62.5% | 100.0% |
| 0.01 | 50.0% | 100.0% |

FIG. 37
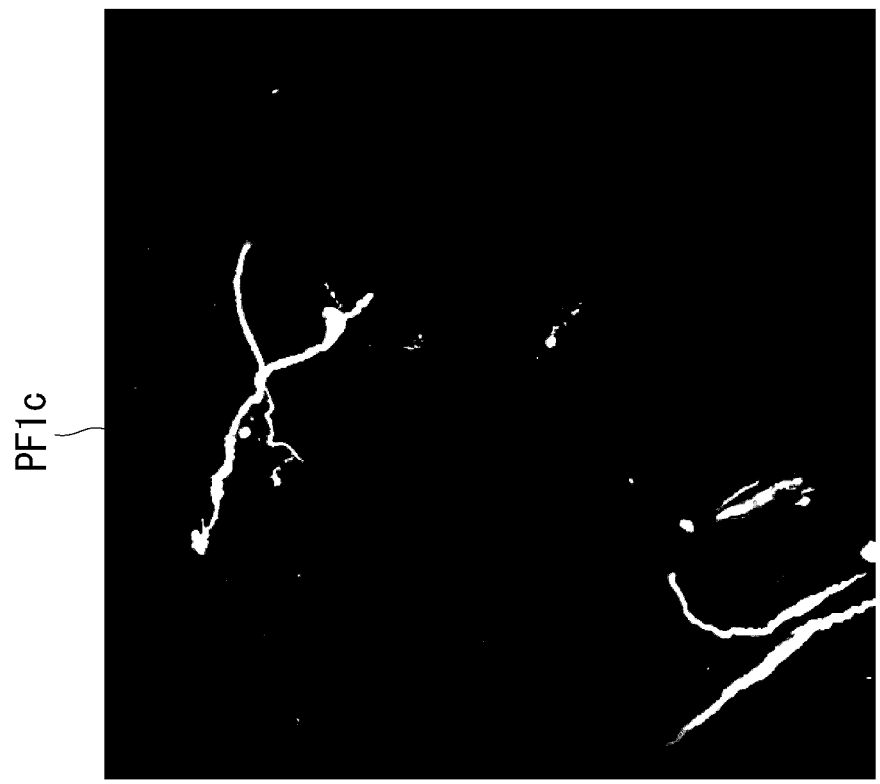
PF1c
PS1c

| DETERMINATION THRESHOLD | SENSITIVITY | SPECIFICITY |
|---|---|---|
| 0.0001 | 100.0% | 0.0% |
| 0.0005 | 100.0% | 66.7% |
| 0.001 | 93.8% | 66.7% |
| 0.0025 | 81.3% | 100.0% |
| 0.005 | 62.5% | 100.0% |
| 0.0075 | 62.5% | 100.0% |
| 0.01 | 50.0% | 100.0% |

IMAGE ACQUIRING DEVICE, CANCER DETERMINATION DEVICE, CANCER DETERMINATION METHOD, AND COMPUTER-READABLE MEDIUM

CROSS-REFERENCE

This application is a continuation of International Patent Application No. PCT/JP2020/039977, filed Oct. 23, 2020, which claims the benefit of and priority to Japanese Patent Application No. 2019-192469 and Patent Application No. 2019-192470, filed Oct. 23, 2019, the contents of all of which are hereby incorporated by reference in their entireties for all purposes.

TECHNICAL FIELD

The present invention relates to a cancer determination device, a cancer determination method, and a computer-readable medium.

BACKGROUND ART

The shapes of cell nuclei have important information in pathological diagnosis. Dyeing cell nuclei in samples of pathologic tissues is an essential procedure. On the other hand, technologies for determining cancer tissues by analyzing images in which biological tissues are imaged are known. When cancer tissues are determined through image analysis, images captured by dyeing biological tissues are used.

For example, a cancer examination device including a determination unit that images a biological cell group to which a dyeing agent for selectively dyeing a cancer-related gene product of a biological cell in a chromatic color is applied and determines a malignancy level of canceration of the biological cell group based on a dyed state of the biological cell group in an obtained image is known (see Patent Document 1).

In the related art, it is difficult to analyze the state of an undyed tissue with a cell level.

CITATION LIST

Patent Literature

[Patent Document 1]
PCT International Publication No. WO 2017/200066

BRIEF DESCRIPTION OF DRAWINGS

FIG. 6 is a diagram showing examples of feature amounts according to the first embodiment.

FIG. 19 is a diagram showing an example of a result of a nucleus region determination process according to the second embodiment.

FIG. 27 is a diagram showing an example of a fiber-like structure image according to the third embodiment.

FIG. 37 is a diagram showing an example of a fiber-like structure image according to the fourth embodiment.

DESCRIPTION OF EMBODIMENTS

First Embodiment

Figure 1:
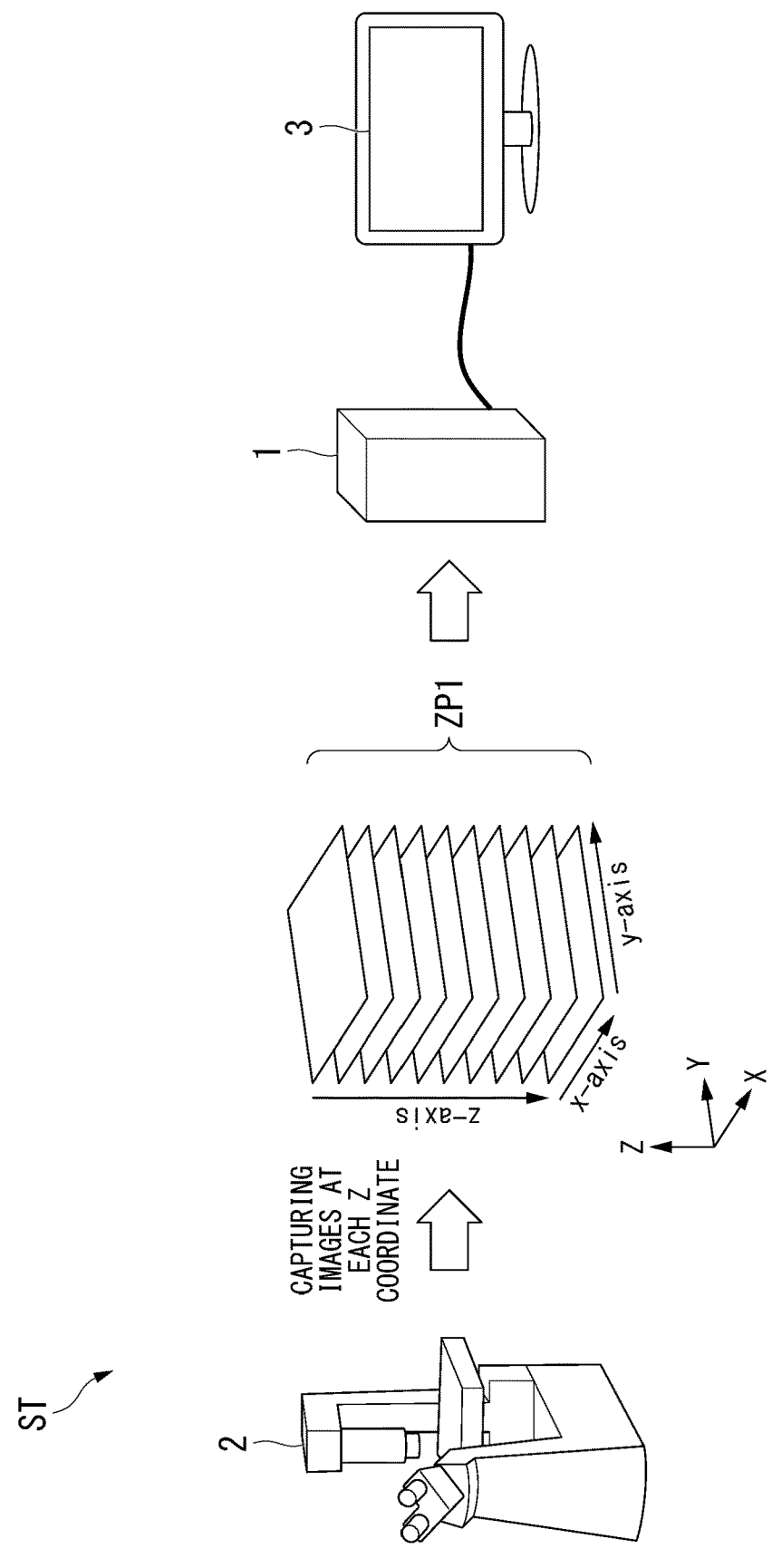
FIG. 1 is a diagram showing an example of a uterine cancer determination system according to a first embodiment.

Hereinafter, a first embodiment will be described in detail with reference to the drawings. FIG. 1 is a diagram showing an example of a uterine cancer determination system ST according to the embodiment. The uterine cancer determination system ST includes a uterine cancer determination device 1, a multiphoton microscope 2, and a display device 3. In the uterine cancer determination system ST, the uterine cancer determination device 1 analyzes Z stack captured images ZP1 of a uterine tissue of an examinee captured by the multiphoton microscope 2 and determines the likelihood that the uterine tissue captured as the Z stack captured images ZP1 is a cancer tissue. The uterine cancer determination device 1 causes the display device 3 to display a determined result.

In the embodiment, a uterine tissue is, for example, a cervix tissue. The uterine tissue may include a corpus uteri. In the embodiment, a uterine tissue will be described as an example, but a tissue is not limited thereto.

The Z stack captured images ZP1 are Z stack images. The Z stack images are a set of a plurality of images captured by changing a distance from a uterine tissue in the Z axis direction. The Z stack captured images ZP1 are formed from a plurality of images obtained by capturing images of the uterine tissue at each Z coordinate. Here, capturing images of the uterine tissue at each Z coordinate involves capturing images of the uterine tissue by variously changing the distance between an objective lens and the uterine tissue. The Z stack captured images ZP1 are a plurality of images captured by the multiphoton microscope 2 by changing a distance between the uterine tissue and a lens.

In the embodiment, the Z axis is selected in a direction oriented inward from an epithelial tissue of a uterine tissue. That is, a value of the Z axis is smaller on an imaging surface close to a uterine epithelial tissue. A value of the Z axis increases as the imaging surface is deeper inside the uterine tissue. The origin of the Z axis is selected at a shallow position close to the uterine epithelial tissue.

In this way, the Z stack captured images ZP1 are a plurality of cross-sectional images perpendicular in a depth direction of the uterine epithelial tissue of the examinee and are simply referred to as cross-sectional images. The depth direction is a direction oriented from a surface layer to a basal layer. The plurality of cross-sectional images may not be completely perpendicular in the depth direction of the uterine epithelial tissue of the examinee and may be inclined about ±5 degrees.

The multiphoton microscope 2 observes and images the uterine tissue of the examinee in an undyed state. The multiphoton microscope 2 images the uterine tissue using a nonlinear optical phenomenon. As the nonlinear optical phenomenon used in the imaging of the multiphoton microscope 2, there are second harmonic generation (SHG) and third harmonic generation (THG).

SHG is a phenomenon in which light with a double frequency of excitation light is generated. SHG occurs by interaction with a nonlinear optical crystal of a collagen fiber or the like.

THG is a phenomenon in which light with a triple frequency of excitation light is generated. THG occurs by interaction with a boundary surface or a layered structure.

In the embodiment, the multiphoton microscope 2 images a uterine tissue using THG to generate a third harmonic image. The third harmonic image is an image of a cross section of a uterine tissue generated based on light generated in third harmonic generation caused by interaction between the uterine tissue and excitation light emitted from an irradiation unit of the multiphoton microscope 2. Captured images included in the Z stack captured images ZP1 are third harmonic images which are images obtained by imaging the uterine tissue using THG. Hereinafter, a third harmonic image is referred to as a THG image.

Hereinafter, the Z stack captured images ZP1 are referred to Z stack THG images ZT1. The Z stack THG images ZT1 are a plurality of THG images obtained by imaging the uterine tissue using THG while changing a distance from the uterine tissue in the Z axis direction. That is, the third harmonic images of the uterine tissue of an examinee are a plurality of cross-sectional images of a uterine epithelial tissue of the examinee.

A plurality of images included in the Z stack THG images ZT1 are expressed as THG images PTi (where i=1, 2, ..., N: N is the number of images included in the Z stack THG images ZT1) or the like.

The multiphoton microscope 2 visualizes cell nuclei in the uterine tissue of the examinee using THG. The uterine tissue of the examinee is exposed to acetic acid in advance.

Figure 2:
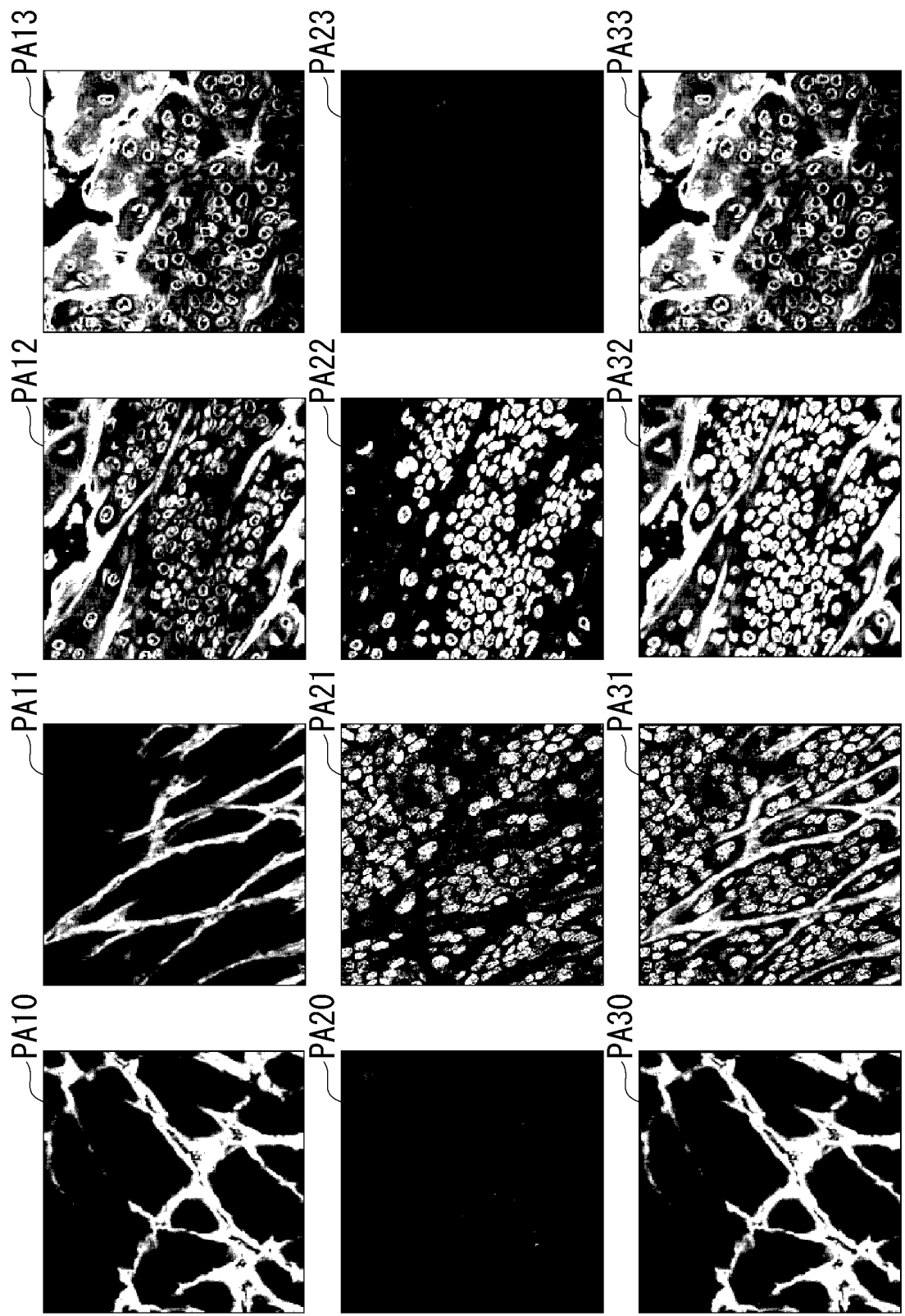
FIG. 2 is a diagram showing examples of captured images of a skin tissue of a mouse to show visualization of cell nuclei implemented using third harmonic generation according to the first embodiment.

Here, visualization of cell nuclei implemented using THG will be described with reference to FIGS. 2 and 3. FIG. 2 is a diagram showing examples of captured images of a skin tissue of a mouse to show visualization of cell nuclei implemented using THG.

A THG image PA10, a THG image PA11 a THG image PA12, and a THG image PA13 are images obtained by imaging the skin tissue of the mouse using THG. A fluorescent image PA20, a fluorescent image PA21, a fluorescent image PA22, and a fluorescent image PA23 are images obtained by dyeing cell nuclei of the skin tissue of the mouse with a fluorochrome and imaging the cell nuclei using the fluorescence. The fluorochrome is Hoechst 33342. A combined image PA30, a combined image PA31, a combined image PA32, and a combined image PA33 are images obtained by combining the images captured using THG and the images captured through the dyeing with Hoechst 33342 and fluorescence.

The THG image PA10 and the fluorescent image PA20 are the images obtained by imaging the skin tissue of the mouse without adding fluorochrome and acetic acid. In the THG image PA10 and the fluorescent image PA20, a common part of the skin tissue is imaged. The combined image PA30 is an image obtained by combining the THG image PA10 and the fluorescent image PA20.

The THG image PA11 and the fluorescent image PA21 are the images obtained by imaging the skin tissue of the mouse after adding fluorochrome. In the THG image PA11 and the fluorescent image PA21, a common part of the skin tissue is imaged. The combined image PA31 is an image obtained by combining the THG image PA11 and the fluorescent image PA21.

The THG image PA12 and the fluorescent image PA22 are the images obtained by imaging the skin tissue of the mouse after adding fluorochrome and acetic acid. In the THG image PA12 and the fluorescent image PA22, a common part of the skin tissue is imaged. The combined image PA32 is an image obtained by combining the THG image PA12 and the fluorescent image PA22.

The THG image PA13 and the fluorescent image PA23 are the images obtained by imaging the skin tissue of the mouse after adding acetic acid. In the THG image PA13 and the fluorescent image PA23, a common part of the skin tissue is imaged. The combined image PA33 is an image obtained by combining the THG image PA13 and the fluorescent image PA23.

The fluorescent image PA22 shows imaging of the cell nucleus. Here, looking at the combined image PA32, it can be understood that the image of the cell nucleus shown in the THG image PA12 matches the image of the dyed cell nucleus shown in the fluorescent image PA22. In the image of the cell nucleus captured using THG after adding fluorochrome and acetic acid, it can be understood that the cell nucleus is imaged similarly to the image of the cell nucleus captured using fluorescence after adding acetic acid.

Next, when the THG image PA13 is compared with the THG image PA12, it can be understood that the image of the cell nucleus is captured in the THG image PA13 similarly to the THG image PA12. That is, in the image captured using THG after adding acetic acid, it can be understood that the cell nucleus is imaged similarly to the image captured using THG after adding fluorochrome and acetic acid.

Accordingly, in the THG image PA13, the cell nucleus is imaged similarly to the fluorescent image PA22. That is, in the image captured using THG after adding acetic acid, the cell nucleus is imaged similarly to the image of the cell nucleus captured using the fluorochrome after adding acetic acid.

In this way, it is possible to capture the image of the cell nucleus without dyeing the cell nucleus by using THG after adding acetic acid.

Figure 3:
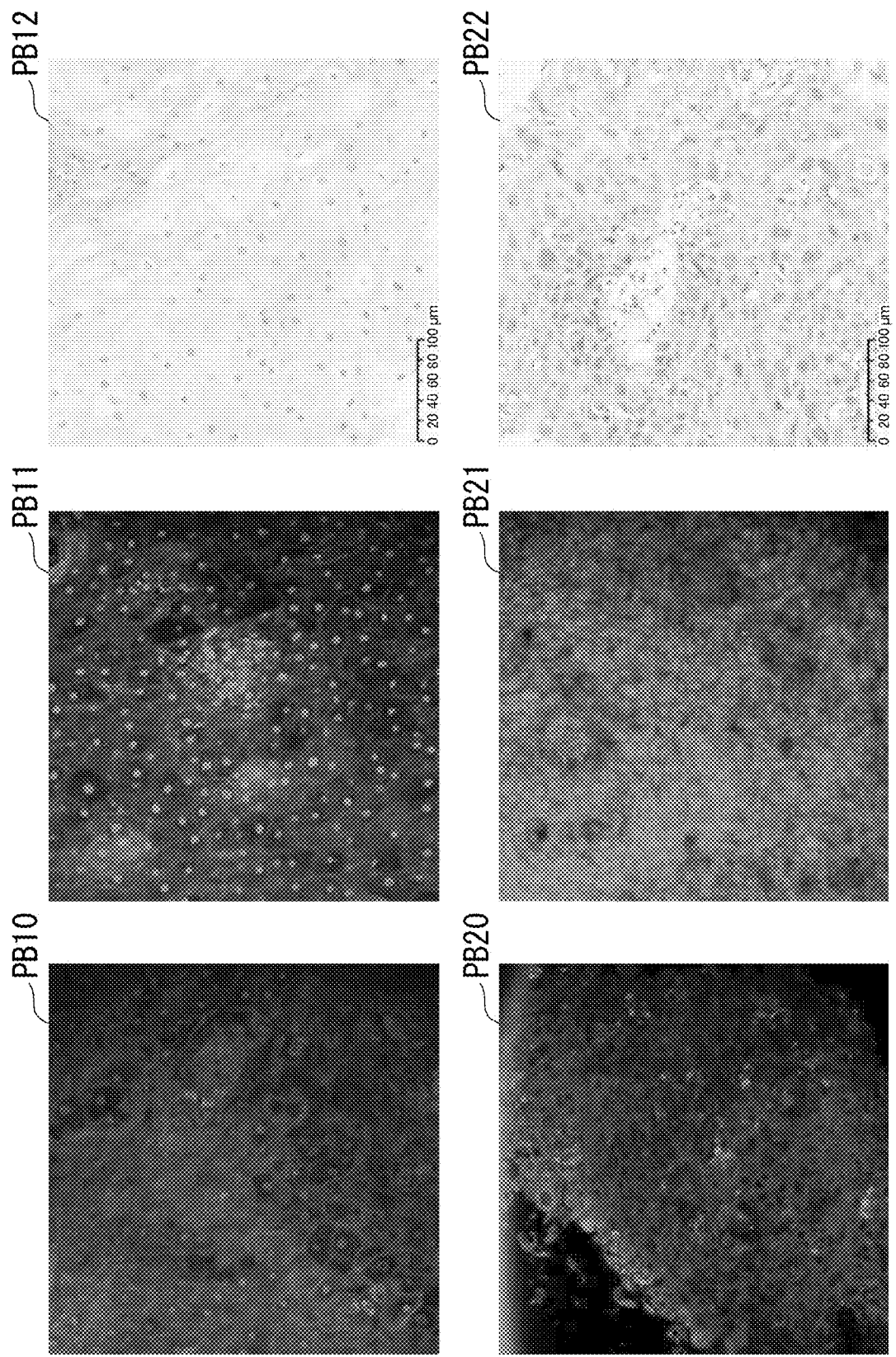
FIG. 3 is a diagram showing examples of captured images of a human uterine tissue according to the first embodiment.

FIG. 3 is a diagram showing examples of captured images of a human uterine tissue according to the embodiment. In the captured images illustrated in FIG. 3, a cervical tissue in a human uterine tissue is imaged. THG images PB10 and PB11 are images obtained by imaging a normal human cervical tissue using THG. THG images PB20 and PB21 are images obtained by imaging a cervical tissue which is a human cancer tissue using THG.

Dyed images PB12 and PB22 are images compared with the THG images. The dyed image PB12 is an image captured by dyeing a normal human cervical tissue with a dyeing agent. The dyed image PB22 is an image captured by dyeing a cervical tissue which is a human cancer tissue with a dyeing agent. The dyeing agent is hematoxylin.

In the THG images PB10 and PB20, the cervical tissue is imaged without adding acetic acid. In the THG images PB11 and PB21, on the other hand, the cervical tissue is imaged after adding acetic acid.

When the THG images PB11 and PB21 are compared with the THG images PB10 and PB20, it can be understood that the cell nuclei are imaged more clearly in the THG images captured after adding acetic acid than in the THG images captured without adding acetic acid.

When the THG images PB11 and PB21 are compared with the dyed images PB12 and PB22, it can be understood that the cell nuclei are imaged in the THG images PB11 and PB21 similarly to the dyed images PB12 and PB22.

That is, for a human cervical tissue, an image of a cell nucleus can also be captured without dyeing the cell nucleus by using THG after adding acetic acid similarly to the skin tissue of the mouse illustrated in FIG. 2.

In the related art, tissues in which cell nuclei are imaged in the THG images captured with a multiphoton microscope are small. In the THG images captured by the multiphoton microscope 2, on the other hand, the cell nucleus of the uterine tissue is imaged.

Configuration of Uterine Cancer Determination Device

Figure 4:
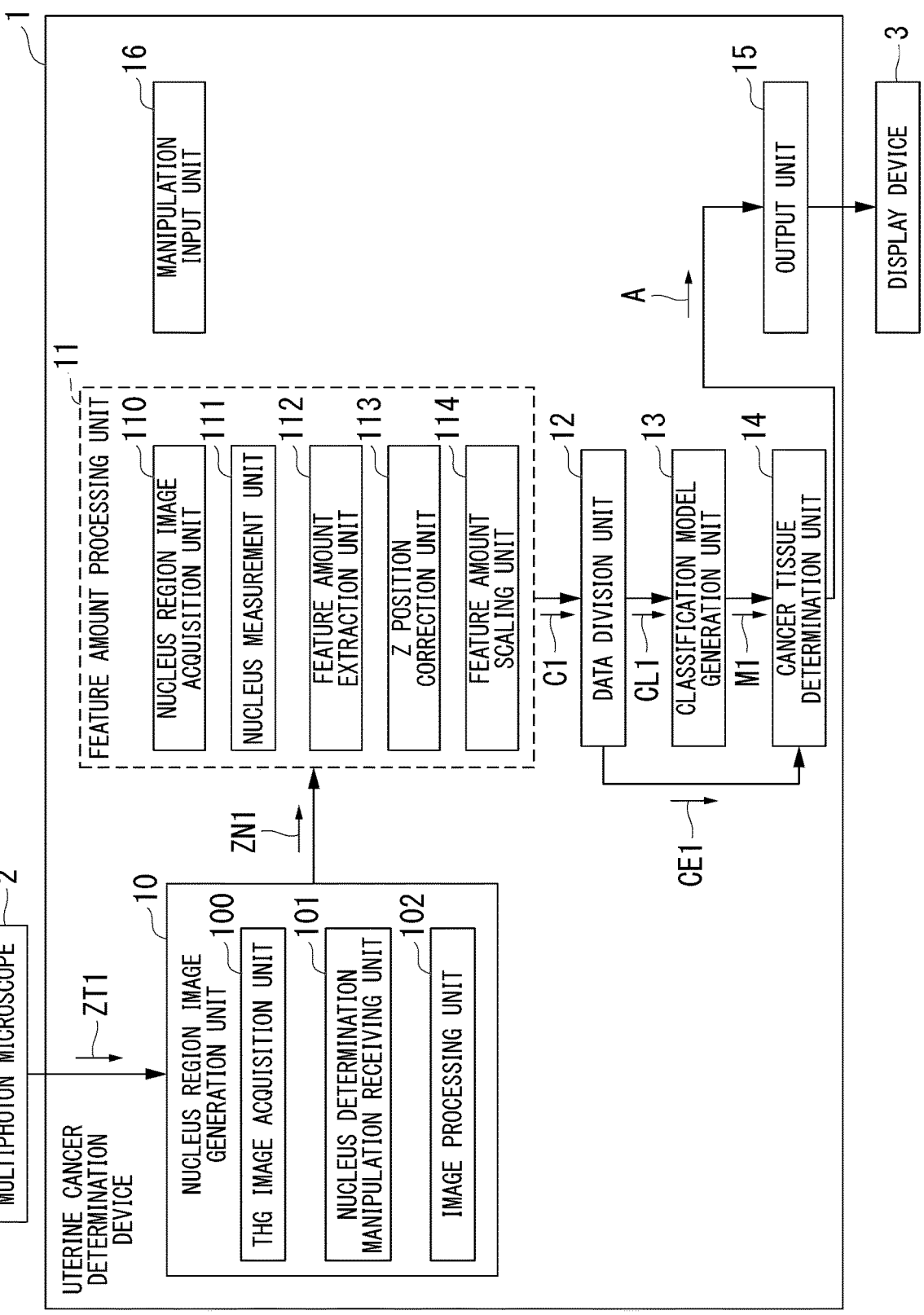
FIG. 4 is a diagram showing an example of a configuration of a uterine cancer determination device according to the first embodiment.

Next, a configuration of the uterine cancer determination device 1 will be described with reference to FIG. 4. FIG. 4 is a diagram showing an example of a configuration of a uterine cancer determination device 1 according to the embodiment. The uterine cancer determination device 1 is, for example, a computer.

The uterine cancer determination device 1 includes a nucleus region image generation unit 10, a feature amount processing unit 11, a data division unit 12, a classification model generation unit 13, a cancer tissue determination unit 14, an output unit 15, and a manipulation input unit 16. The nucleus region image generation unit 10, the feature amount processing unit 11, the data division unit 12, the classification model generation unit 13, the cancer tissue determination unit 14, and the output unit 15 are modules implemented by causing a central processing unit (CPU) to read a program from a read-only memory (ROM) and performing a process.

The nucleus region image generation unit 10 generates Z stack nucleus region images ZN1 from the Z stack THG images ZT1 captured by the multiphoton microscope 2. Here, the Z stack nucleus region images ZN1 are a plurality of images in which regions indicating cell nuclei of the uterine tissue are shown in the THG images PTi (where i=1, 2, . . . , N: N is the number of images included in the Z stack THG images ZT1) which are a plurality of images included in the Z stack THG images ZT1.

The plurality of images included in the Z stack nucleus region images ZN1 are referred to as nucleus region images PNi (where i=1, 2, . . . , N: N is the number of images included in the Z stack nucleus region images ZN1).

In the embodiment, the nucleus region which is a region indicating a cell nucleus is determined by, for example, a user of the uterine cancer determination device 1. The user of the uterine cancer determination device 1 visually checks the Z stack captured images ZP1 and determines the nucleus region based on knowledge and experience.

Figure 5:
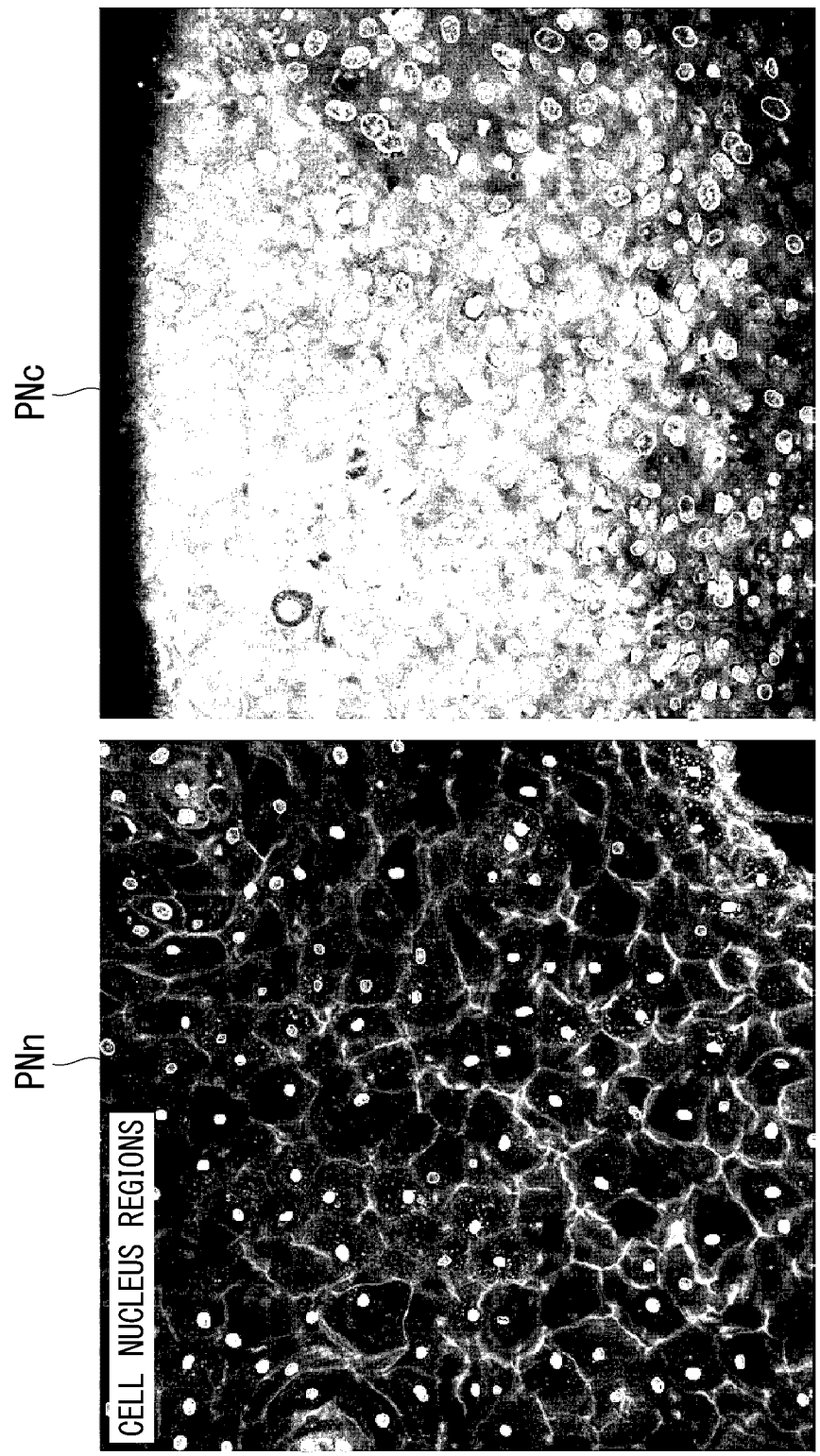
FIG. 5 is a diagram showing examples of nucleus region images according to the first embodiment.

Here, examples of the nucleus region images PNi will be described with reference to FIG. 5. FIG. 5 is a diagram showing examples of the nucleus region images PNi according to the embodiment. In a nucleus region PNn, a nucleus region is determined in a THG image PTi of a normal uterine tissue and the contour of the determined nucleus region is colored. In a nucleus region PNc, a region indicating a cell nucleus is determined in a THG image PTi of a uterine tissue which is a cancer tissue and the contour of the determined nucleus region is colored.

Referring back to FIG. 4, the description of the configuration of the uterine cancer determination device 1 will continue.

The nucleus region image generation unit 10 includes a THG image acquisition unit 100, a nucleus determination manipulation receiving unit 101, and an image processing unit 102.

The THG image acquisition unit 100 acquires the Z stack captured images ZP1 captured by the multiphoton microscope 2.

The nucleus determination manipulation receiving unit 101 receives a nucleus determination manipulation from the user of the uterine cancer determination device 1 via the manipulation input unit 16. Here, the nucleus determination manipulation is a manipulation of determining a region indicating a cell nucleus of a uterine tissue in each of the THG images PTi included in the Z stack captured images ZP1.

The image processing unit 102 generates Z stack nucleus region images ZN1 from the Z stack captured images ZP1 based on the nucleus determination manipulation received by the nucleus determination manipulation receiving unit 101.

The feature amount processing unit 11 extracts feature amounts C1 from the Z stack nucleus region images ZN1 and performs various processes on the extracted feature amounts C1. The feature amounts C1 are feature amounts indicating states of cell nuclei and are extracted from each nucleus region image PNi. In the embodiment, the state of the cell nucleus is at least one selected from a group formed of areas of the cell nuclei, densities of the cell nuclei, and shapes of the cell nuclei.

The feature amount processing unit 11 includes a nucleus region image acquisition unit 110, a nucleus measurement unit 111, a feature amount extraction unit 112, a Z position correction unit 113, and a feature amount scaling unit 114.

The nucleus region image acquisition unit 110 acquires the Z stack nucleus region image ZN1 supplied from the nucleus region image generation unit 10.

The nucleus measurement unit 111 performs various kinds of measurement on each cell nucleus based on the images of the cell nuclei captured in the Z stack nucleus region image ZN1. Examples of the various kinds of measurement include the area, roundness, and nearest distance.

The feature amount extraction unit 112 extracts the feature amounts C1 for each nucleus region image PNi included in the Z stack nucleus region images ZN1 based on a result measured by the nucleus measurement unit 111.

Here, the details of the feature amounts C1 will be described with reference to FIG. 6. FIG. 6 is a diagram showing examples of the feature amounts C1 according to the embodiment. The feature amounts C1 include, for example, the areas of cell nuclei, roundness of the cell nuclei, the nearest distances between cell nuclei, and the number of cell nuclei. For the areas, the roundness, and the nearest distances of the feature amounts C1, the median and the median absolute error are calculated and used.

An image of a normal cervical tissue captured through multiphoton excitation imaging matches pathological knowledge because a cell nucleus expresses a distinctive feature according to a depth from the surface. Here, the depth from the surface is classified into an upper layer, an intermediate layer, and a lower layer. FIG. 6 illustrates a qualitative feature of a feature amount at each depth from the surface which is classified in accordance with a value of "large," "medium," and "small."

In the uterine cancer determination device 1, effective feature amounts of cell nuclei are selected in advance to determine the likelihood that a uterine tissue is a cancer tissue.

For example, the median area of cell nuclei is, for example, "small" in the upper layer, "medium" in the intermediate layer, and "medium" in the lower layer for a normal tissue. That is, for the normal tissue, "large" is not indicated in any layer as the median area. On the other hand, the median area is "large" in a first cancer tissue. Thus, a cancer tissue indicating "large" is confirmed. Therefore, a "large" median of the areas is at least a first feature of cancer, and is considered to be a feature by which a cancer tissue can be distinguished from a normal tissue.

A "large" median area corresponds to a pathological feature indicating that a cell nucleus swells.

Similarly, a "large" median absolute error of the areas of the cell nuclei, a "small" median value of roundness of the cell nuclei, a "large" median absolute error of the roundness of the cell nuclei, a "small" median value of nearest distances between cell nuclei, a "large" median absolute error of nearest distances between cell nuclei, and "many" cell nuclei, respectively, are considered to be features by which a cancer tissue can be distinguished from a normal tissue.

A "large" median absolute error of the areas of cell nuclei corresponds to a pathological feature indicating that of a nucleus size is ununiform. A "small" median of the roundness of cell nuclei corresponds to a pathological feature indicating that the cell nuclei are heteromorphic. A "large" median absolute error of the roundness of cell nuclei corresponds to a pathological feature indicating that the cell nuclei are heteromorphic. A "small" median of the nearest distances between the cell nuclei corresponds to a pathological feature indicating that density of the cell nuclei is high. A "large" median absolute error of the nearest distances between the cell nuclei corresponds to a pathological feature indicating that a distribution in a region where there are cell nuclei is ununiform. The "many" cell nuclei correspond to a pathological feature indicating that density of the cell nuclei is high.

In summary, the features of the cell nuclei of the uterine tissue which is a cancer tissue are the following features (i) to (vi):

(i) the average of areas of cell nuclei is larger than in normal uterine tissues;

(ii) the variation in the areas of the cell nuclei is greater than in the normal uterine tissues;

(iii) the density of the cell nuclei is higher than in the normal uterine tissues;

(iv) the variation in the density of the cell nuclei is greater than in the normal uterine tissues;

(v) the distortion of the shapes of the cell nuclei is greater than in the normal uterine tissues; and (vi) the variation in the shapes of the cell nuclei is greater than in the normal uterine tissues.

Referring back to FIG. 4, the description of the configuration of the uterine cancer determination device 1 will continue.

The Z position correction unit 113 corrects the Z stack nucleus region images ZN1 in the Z axis direction.

The feature amount scaling unit 114 scales the feature amounts C1 extracted by the feature amount extraction unit 112 based on normalization or standardization.

The data division unit 12 divides the feature amounts C1 extracted by the feature amount processing unit 11 into learning feature amount data CL1 used for learning and determination feature amount data CE1 used for determination.

The classification model generation unit 13 generates a classification model M1 based on machine learning using the learning feature amount data CL1. Here, the machine learning used by the classification model generation unit 13 is, for example, a nonlinear support vector machine.

The cancer tissue determination unit 14 determines the likelihood that a uterine tissue is a cancer tissue based on the determination feature amount data CE1 and the classification model M1 generated by the classification model generation unit 13.

The output unit 15 outputs a determination result A of the cancer tissue determination unit 14 to the display device 3. The determination result A indicates whether the uterine tissue is a cancer tissue or a normal tissue. The determination result A according to the embodiment is exemplary. The cancer tissue determination unit 14 may output a probability indicating whether the uterine tissue is a cancer tissue or a normal tissue to the display device 3 or may output the determination result to the display device 3 in parallel to the learning feature amount data CL1 used for learning.

The manipulation input unit 16 receives various manipulations from the user of the uterine cancer determination device 1. The manipulation input unit 16 is, for example, a touch panel, a mouse, or a keyboard.

The display device 3 displays the determination result A determined by the uterine cancer determination device 1. The display device 3 is, for example, a display.

Process of Uterine Cancer Determination System

Figure 7:
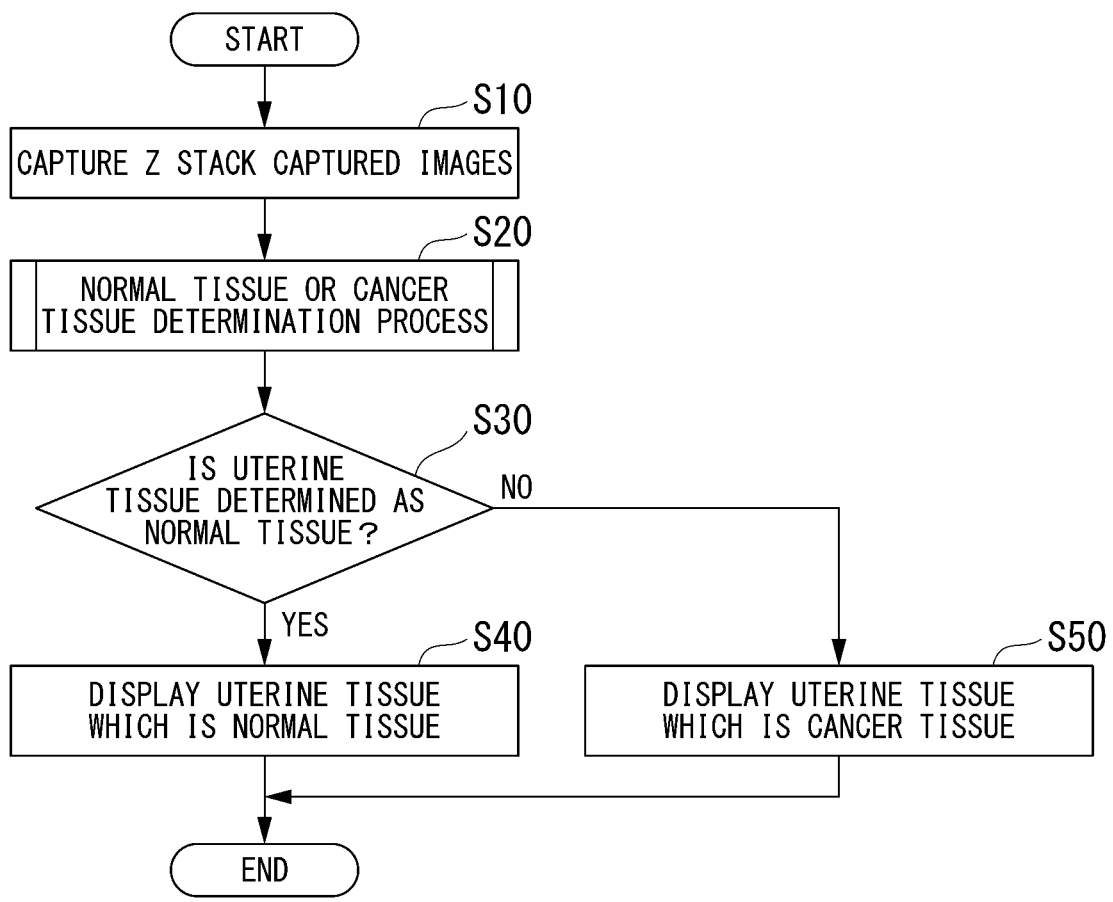
FIG. 7 is a diagram showing an example of a uterine cancer determination process according to the first embodiment.

Next, a uterine cancer determination process which is a process of the uterine cancer determination system ST will be described. FIG. 7 is a diagram showing an example of a uterine cancer determination process according to the embodiment.

Step S10: the multiphoton microscope 2 captures the Z stack captured images ZP1 of the uterine tissue of the examinee. Here, in the embodiment, as described above, the Z stack captured images ZP1 are Z stack THG images ZT1. The multiphoton microscope 2 outputs the captured Z stack captured images ZP1 to the uterine cancer determination device 1.

Step S20: the uterine cancer determination device 1 performs a normal tissue or cancer tissue determination process which is a process of determining whether the uterine tissue of the examinee is a normal tissue or a cancer tissue based on the Z stack captured images ZP1 captured by the multiphoton microscope 2. The details of the normal tissue or cancer tissue determination process will be described below with reference to FIG. 8.

Step S30: the output unit 15 of the uterine cancer determination device 1 performs a process based on the determination result A. When it is determined that the uterine tissue of the examinee is a normal tissue (YES in step S30), the output unit 15 outputs a result indicating that the uterine tissue of the examinee is a normal tissue to the display device 3. Thereafter, the display device 3 performs a process of step S40.

Conversely, when it is determined that the uterine tissue of the examinee is not a normal tissue, that is, is a cancer tissue (NO in step S30), the output unit 15 outputs a result indicating that the uterine tissue of the examinee is a cancer tissue to the display device 3. Thereafter, the display device 3 performs a process of step S50.

Step S40: the display device 3 displays a result indicating that the uterine tissue of the examinee is a normal tissue.

Step S50: the display device 3 displays a result indicating that the uterine tissue of the examinee is a cancer tissue.

With this, the uterine cancer determination system ST ends the uterine cancer determination process.

Process of Uterine Cancer Determination Device 1

Next, the details of the normal tissue or cancer tissue determination process of the uterine cancer determination device 1 will be described. As the normal tissue or cancer tissue determination process, there is a nucleus region image generation process of generating the Z stack nucleus region images ZN1, a learning process of generating the classification model M1, and a determination process of determining the likelihood that the uterine tissue is a cancer tissue based on the classification model M1.

Figure 8:
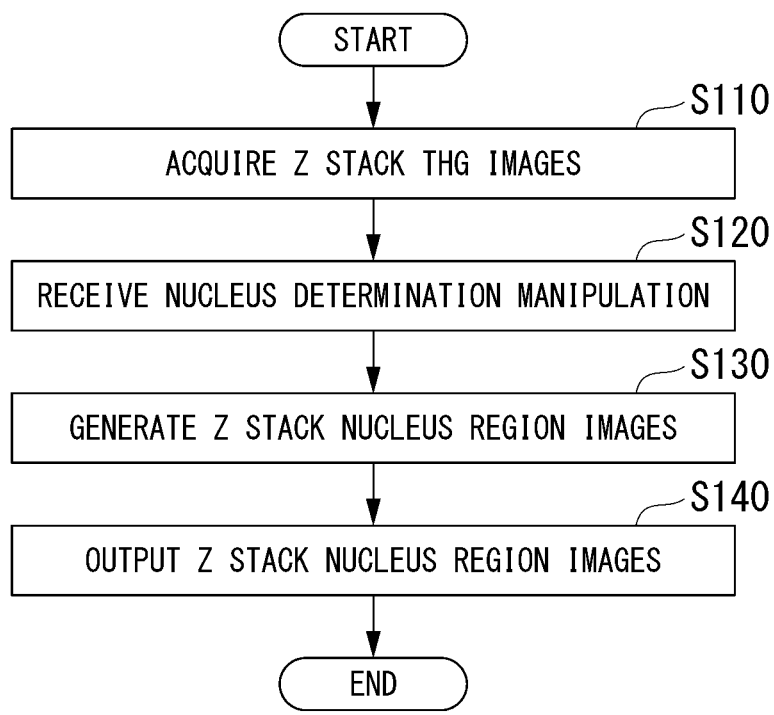
FIG. 8 is a diagram showing an example of a nucleus region image generation process according to the first embodiment.

FIG. 8 is a diagram showing an example of a nucleus region image generation process according to the embodiment.

Step S110: the THG image acquisition unit 100 acquires the Z stack captured images ZP1 captured by the multiphoton microscope 2. That is, the THG image acquisition unit 100 acquires a third harmonic image of the uterine tissue of the examinee obtained with the multiphoton microscope 2.

The THG image acquisition unit 100 supplies the acquired Z stack captured images ZP1 to the nucleus determination manipulation receiving unit 101.

Figure 9:
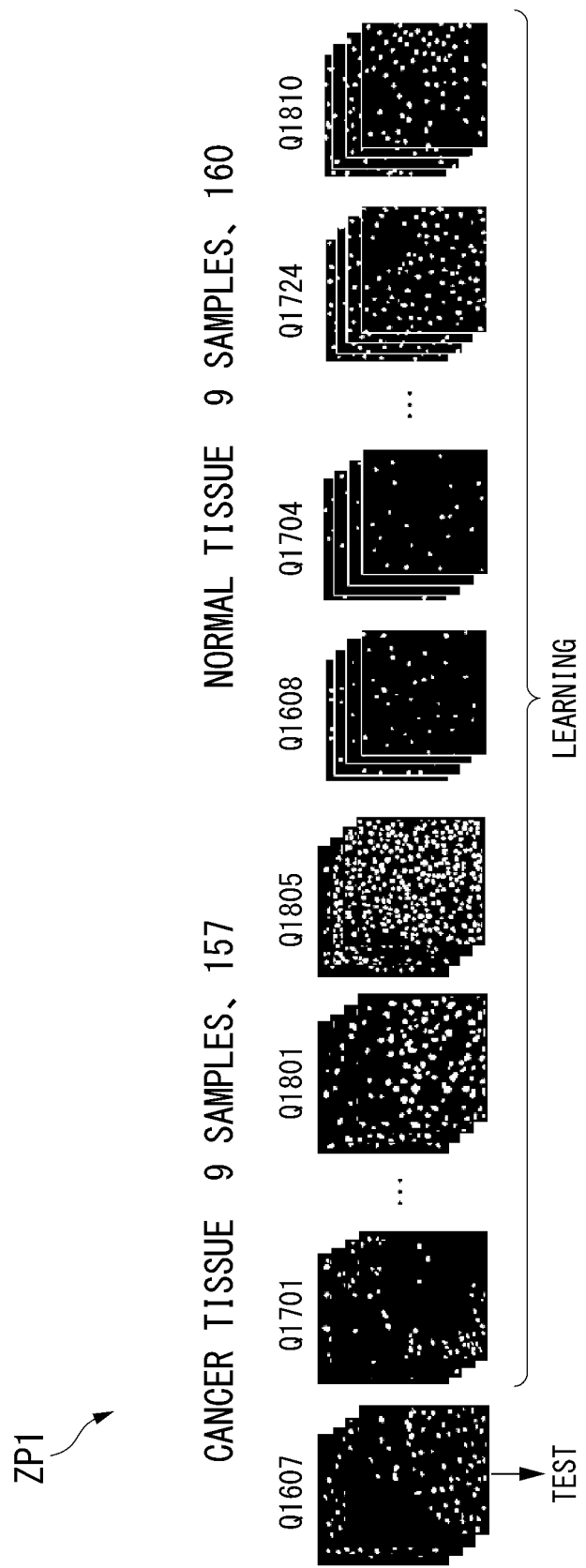
FIG. 9 is a diagram showing examples of Z stack nucleus region images according to the first embodiment.

Here, the details of the Z stack nucleus region images ZN1 will be described with reference to FIG. 9. FIG. 9 is a diagram showing examples of the Z stack nucleus region images ZN1 according to the embodiment. In the embodiment, the Z stack nucleus region images ZNZP1 are a plurality of images. THG images PTi (where i=1, 2, . . . , 317) included in the Z stack captured images ZP1 are formed from 512×512 pixels.

The Z stack captured images ZP1 include 157 THG images PTi in which the uterine tissue which is a cancer tissue is imaged and 160 THG images PTi in which the uterine tissue which is a normal tissue is imaged. In the imaging of the THG images PTi in which the uterine tissue which is a cancer tissue is imaged and the THG images PTi in which the uterine tissue which is a normal tissue is imaged, respectively, uterine tissues of nine samples are used.

In a determination process, the uterine cancer determination device 1 uses images for one certain sample among the THG images PTi in which a uterine tissue which is a cancer tissue is imaged. In the learning process, the uterine cancer determination device 1 uses images for 17 samples which are the remaining images unused in the determination process for the THG images PTi in which the uterine tissue which is the cancer tissue is imaged and the THG images PTi in which the uterine tissue which is the normal tissue is imaged.

Learning third harmonic images which are a plurality of THG images PTi used in the learning process are a plurality of cross-sectional images of a uterine epithelial tissue.

Referring back to FIG. 8, description of the nucleus region image generation process will continue.

Step S120: the nucleus determination manipulation receiving unit 101 receives a nucleus determination manipulation from the user of the uterine cancer determination device 1 via the manipulation input unit 16. The nucleus determination manipulation receiving unit 101 supplies information indicating the received nucleus determination manipulation and the Z stack captured images ZP1 to the image processing unit 102.

Here, for example, the nucleus determination manipulation receiving unit 101 causes the display device 3 to display the Z stack captured images ZP1 acquired by the THG image acquisition unit 100. The user of the uterine cancer determination device 1 determines a region indicating the cell nuclei of the uterine tissue of each THG image PTi while checking the THG images TPi included in the Z stack captured images ZP1 displayed on the display device 3. The user of the uterine cancer determination device 1 inputs a manipulation of determining a region indicating the cell nuclei via the manipulation input unit 16. The nucleus determination manipulation is performed, for example, by tracing the contour of a region determined to be the region indicating the cell nuclei with a mouse pointer via the manipulation input unit 16 which is a mouse in the THG image PTi displayed on the display device 3 which is a display.

The nucleus determination manipulation may be performed by tracking the contour of a region determined to be the region indicating the cell nuclei using the manipulation input unit 16 which is a touch pen in the THG image PTi displayed on the display device 3 which is a touch panel.

Step S130: the image processing unit 102 generates the Z stack nucleus region images ZN1 from the Z stack captured images ZP1 based on the nucleus determination manipulation received by the nucleus determination manipulation receiving unit 101. Here, the image processing unit 102 generates the Z stack nucleus region images ZN1 by coloring the contour of the region indicating the cell nuclei of the uterine tissue in each THG image PTi based on the nucleus determination manipulation.

Step S140, the image processing unit 102 outputs the generated Z stack nucleus region images ZN1 to the feature amount processing unit 11.

With this, the uterine cancer determination device 1 ends the nucleus region image generation process.

Figure 10:
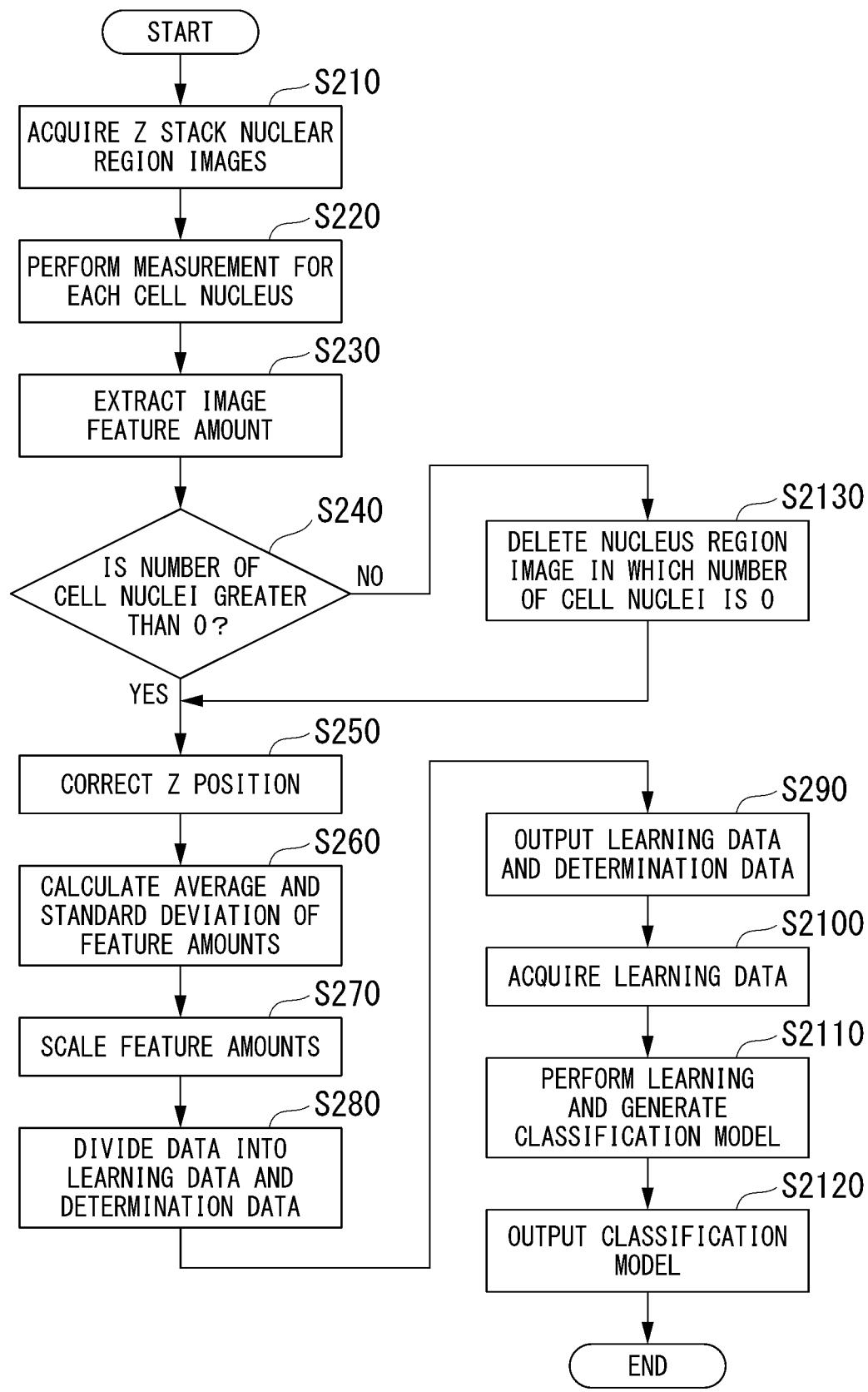
FIG. 10 is a diagram showing an example of a learning process according to the first embodiment.

Next, a learning process of the uterine cancer determination device 1 will be described with reference to FIG. 10. FIG. 10 is a diagram showing an example of the learning process according to the embodiment.

Step S210: the nucleus region image acquisition unit 110 acquires the Z stack nucleus region images ZN1 supplied from the nucleus region image generation unit 10. Here, the Z stack nucleus region images ZN1 supplied from the nucleus region image generation unit 10 are generated in the above-described nucleus region image generation process. The nucleus region images PNi in which the uterine tissue which is a cancer tissue is imaged and the nucleus region images PNi in which the uterine tissue which is a normal tissue is imaged are determined in advance. The nucleus region image acquisition unit 110 supplies the acquired Z stack nucleus region images ZN1 to the nucleus measurement unit 111.

Step S220: the nucleus measurement unit 111 measures an area, roundness, and the nearest distance for each cell nucleus based on the images of the cell nuclei captured in the Z stack nucleus region images ZN1 acquired by the nucleus region image acquisition unit 110. The nucleus measurement unit 111 supplies a measurement result to the feature amount extraction unit 112.

Figure 11:
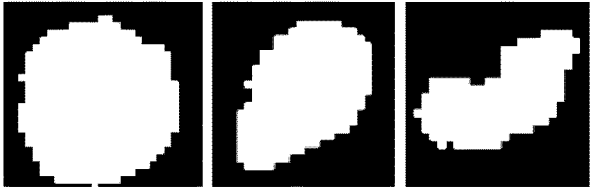
FIG. 11 is a diagram showing an example of measurement of a cell nucleus according to the first embodiment.

Here, measurement of the cell nucleus performed by the nucleus measurement unit 111 will be described with reference to FIG. 11. FIG. 11 is a diagram showing an example of the measurement of the cell nucleus according to the embodiment.

The nucleus measurement unit 111 measures the number of pixels of the cell nucleus region×an area per pixel. Here, the area per pixel depends on magnification of the multiphoton microscope 2 and is, for example, 1 μm².

The nucleus measurement unit 111 measures $4\pi \times (area)/(square\ of\ circumference)$ as the roundness. The roundness can take a value from 0 to 1. The roundness takes a value closer to 1 as the contour of the cell nucleus is closer to a circle.

The nucleus measurement unit 111 calculates, as the nearest distance, the Euclidean distance from the center of gravity of a measurement target label to the center of gravity of another label closest to that center of gravity by causing the labels to correspond to the cell nuclei.

Referring back to FIG. 10, description of the learning process will continue.

Step S230: the feature amount extraction unit 112 extracts the feature amounts C1 for each nucleus region image PNi included in the Z stack nucleus region images ZN1 based on a result measured by the nucleus measurement unit 111.

Step S240: the feature amount extraction unit 112 determines whether the number of cell nuclei is greater than 0 for each nucleus region image PNi. As described above, the number of cell nuclei is included in the feature amount C1 and the feature amount extraction unit 112 performs determination based on the feature amount C1.

A case in which the number of cell nuclei captured in the nucleus region images PNi is 0 is, for example, a case in which the uterine tissue is imaged with the uterine tissue not included in the imaging surface in the imaging near the epithelium of the uterine tissue because the epithelium is inclined in a direction perpendicular to the Z axis direction.

When the feature amount extraction unit 112 determines that the number of cell nuclei is greater than 0 for each nucleus region image PNi (YES in step S240), the feature amount processing unit 11 performs a process of step S250. Conversely, when the feature amount extraction unit 112 determines that the number of cell nuclei is 0 for each nucleus region image PNi (NO in step S240), the feature amount processing unit 11 performs a process of step S2130.

Step S250: the Z position correction unit 113 performs correction on the Z stack nucleus region images ZN1 in the Z axis direction. Here, the Z position correction unit 113 corrects a value of the Z coordinate, for example, so that the Z coordinate of the imaging surface corresponding to the nucleus region image PNi in which the Z coordinate is the smallest becomes the origin of the Z axis from the nucleus region images PNi in which the feature amount extraction unit 112 determines that the number of cell nuclei is greater than 1.

The Z position correction unit 113 can perform the correction in the Z axis direction even when the number of nucleus region images included in the Z stack nucleus region images ZN1 is 1.

Step S260: the feature amount scaling unit 114 calculates average and standard deviation of each kind of feature amount C1 extracted by the feature amount extraction unit 112 with regard to the nucleus region images PNi included in the Z stack nucleus region images ZN1.

Step S270: the feature amount scaling unit 114 performs scaling using the average or the standard deviation calculated for each kind of feature amount C1 extracted by the feature amount extraction unit 112. Here, the feature amount scaling unit 114 performs the scaling on the feature amounts C1 based on, for example, normalization or standardization. For example, the feature amount scaling unit 114 unifies ranges of values taken by the different kinds of feature amounts included in the feature amounts C1 through normalization. Alternatively, the feature amount scaling unit 114 sets 0 as the average of the different types of feature amounts included in the feature amounts C1 and sets 1 as dispersion of the different types of feature amounts through standardization.

Step S280: the data division unit 12 divides the feature amounts C1 scaled by the feature amount scaling unit 114 into the learning feature amount data CL1 used for learning and the determination feature amount data CE1 used for determination. The data division unit 12 sets, as the determination feature amount data CE1, the feature amounts extracted for one certain sample in the THG image PTi obtained by imaging the uterine tissue which is a cancer tissue in the feature amounts C1. The data division unit 12 sets the remaining feature amounts among the feature amounts C1 as the learning feature amount data CL1.

Here, as described above, in the Z stack nucleus region images ZN1 acquired by the nucleus region image acquisition unit 110 in step S210, the nucleus region images PNi in which the uterine tissue which is a cancer tissue is imaged and the nucleus region images PNi in which the uterine tissue which is a normal tissue is imaged are determined in advance. The data division unit 12 maps labels to distinguish the feature amounts extracted from the nucleus region images PNi in which the uterine tissue which is a cancer tissue is imaged from the feature amounts extracted from the nucleus region images PNi in which the uterine tissue which is a normal tissue is imaged for each piece of data of the learning feature amount data CL1.

Step S290: the data division unit 12 outputs the learning feature amount data CL1 to the classification model generation unit 13. The data division unit 12 outputs the determination feature amount data CE1 to the cancer tissue determination unit 14.

Step S2100: the classification model generation unit 13 acquires the learning feature amount data CL1 output from the data division unit 12.

Step S2110: the classification model generation unit 13 generates the classification model M1 based on machine learning using the acquired learning feature amount data CL1. Here, the classification model generation unit 13 generates the classification model M1 based on, for example, a nonlinear support vector machine. The classification model generation unit 13 may generate the classification model M1 based on machine learning other than the nonlinear support vector machine.

As described above, the learning feature amount data CL1 is extracted from the Z stack nucleus region images ZN1 generated from the Z stack captured images ZP1 formed from the THG images PTi in which the uterine tissue which is a cancer tissue is imaged and the THG images PTi in which the uterine tissue which is a normal tissue is imaged. Accordingly, the classification model M1 is a classification model learned using the learning third harmonic images of normal uterine tissues obtained with the multiphoton microscope and/or the learning third harmonic images of uterine cancer tissues obtained with the multiphoton microscope.

Step S2120: the classification model generation unit 13 outputs the generated classification model M1 to the cancer tissue determination unit 14.

With this, the uterine cancer determination device 1 ends the learning process.

Step S2130: the feature amount extraction unit 112 deletes the nucleus region images PNi in which the number of cell nuclei is 0. That is, the feature amount extraction unit 112 does not use the nucleus region images PNi in which the number of cell nuclei is determined to be 0 in the subsequent processes (processes from step S250 to S2130).

Figure 12:
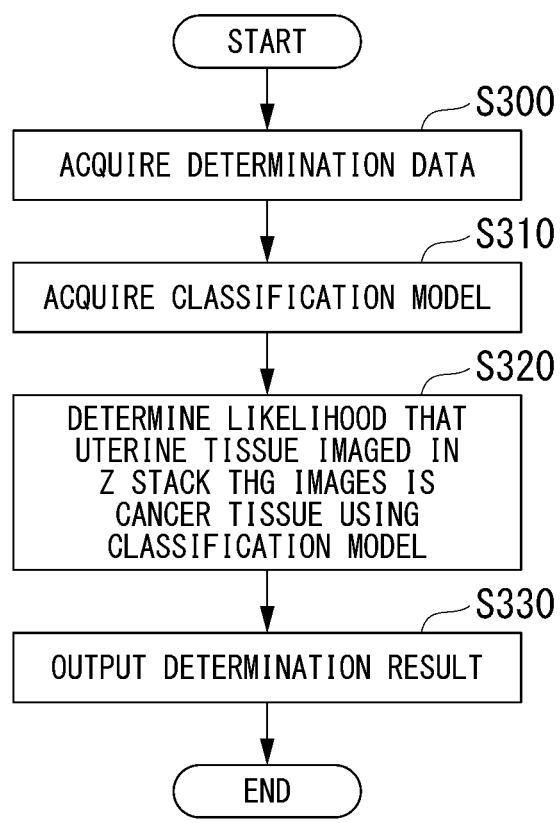
FIG. 12 is a diagram showing an example of a determination process according to the first embodiment.

Next, a determination process of the uterine cancer determination device 1 will be described with reference to FIG. 12. FIG. 12 is a diagram showing an example of the determination process according to the embodiment.

Step S300: the cancer tissue determination unit 14 acquires the determination feature amount data CE1 output from the data division unit 12.

Step S310: the cancer tissue determination unit 14 acquires the classification model M1 output from the classification model generation unit 13.

Step S320: the cancer tissue determination unit 14 determines the likelihood that a uterine tissue imaged in the Z stack THG image ZT1 is a cancer tissue using the determination feature amount data CE1 and the classification model M1. Here, as described above, the feature amounts C1 are extracted for each nucleus region image PNi included in the Z stack nucleus region images ZN1 generated from the Z stack THG images ZT1. Therefore, it is possible to determine the likelihood that the uterine tissue imaged in the THG images PTi corresponding to the nucleus region images PNi from which the determination feature amount data CE1 is extracted is a cancer tissue by using the determination feature amount data CE1.

As described above, the feature amounts C1 are feature amounts indicating states of the cell nuclei imaged in the nucleus region images PNi included in the Z stack nucleus region images ZN1. Accordingly, the cancer tissue determination unit 14 determines the likelihood that the uterine tissue of the examinee is a cancer tissue based on the states of the cell nuclei in the third harmonic images of the uterine tissue of the examinee.

As described above, the cancer tissue determination unit 14 determines the likelihood that the uterine tissue imaged in the Z stack THG images ZN1 is a cancer tissue based on the classification model M1. As described above, the classification model M1 is a classification model learned using the learning third harmonic images of normal uterine tissues obtained with the multiphoton microscope and/or the learning third harmonic images of uterine cancer tissues obtained with the multiphoton microscope. The cancer tissue determination unit 14 determines the likelihood that the uterine tissue of the examinee is a cancer tissue based on the states of the cell nuclei in third harmonic images of the uterine tissue of the examinee with reference to the classification model M1 learned using the learning third harmonic images of normal uterine tissues obtained with the multiphoton microscope and/or the learning third harmonic images of uterine cancer tissues obtained with the multiphoton microscope.

As described above, the classification model M1 is a model obtained as a result of performing the machine learning using the feature amounts C1. The feature amounts C1 include the median and the median absolute error of areas of cell nuclei, the median and the median absolute error of roundness of the cell nuclei, and the median and the median absolute error of the nearest distances between the cell nuclei.

The cancer tissue determination unit 14 determines that the likelihood that the uterine tissue of the examinee is a cancer tissue is high when at least one of the following features is satisfied:

(i) the average of areas of cell nuclei is larger than in normal uterine tissues;

(ii) the variation in the areas of the cell nuclei is greater than in the normal uterine tissues;

(iii) the density of the cell nuclei is higher than in the normal uterine tissues;

(iv) the variation in the density of the cell nuclei is greater than in the normal uterine tissues;

(v) the distortion of the shapes of the cell nuclei is greater than in the normal uterine tissues; and (vi) the variation in the shapes of the cell nuclei is greater than in the normal uterine tissues.

The cancer tissue determination unit 14 calculates the likelihood that the uterine tissue is a cancer tissue based on, for example, a ratio of the determination Z stack captured images ZP1 in which the likelihood that the uterine tissue is determined to be a cancer tissue is high to all the determination Z stack captured images ZP1. First, the cancer tissue determination unit 14 determines the likelihood that the uterine tissue imaged in each of the plurality of THG images PT1 included in the determination Z stack captured images ZP1 is a cancer tissue. Subsequently, the cancer tissue determination unit 14 calculates the likelihood that the uterine tissue is a cancer tissue based on the ratio of the determination Z stack captured images ZP1 in which the likelihood that the uterine tissue is determined to be a cancer tissue is high to all the determination Z stack captured images ZP1.

That is, the cancer tissue determination unit 14 determines the likelihood that the uterine tissue of the examinee is a cancer tissue in each of the plurality of third harmonic images of the uterine tissue of the examinee and calculates the likelihood that the uterine tissue of the examinee is a cancer tissue based on the ratio of the third harmonic images in which the likelihood that the uterine tissue is determined to be a cancer tissue is high to all the third harmonic images.

Step S330: the cancer tissue determination unit 14 outputs the determination result A to the output unit 15.

With this, the uterine cancer determination device 1 ends the determination process.

Figure 13:
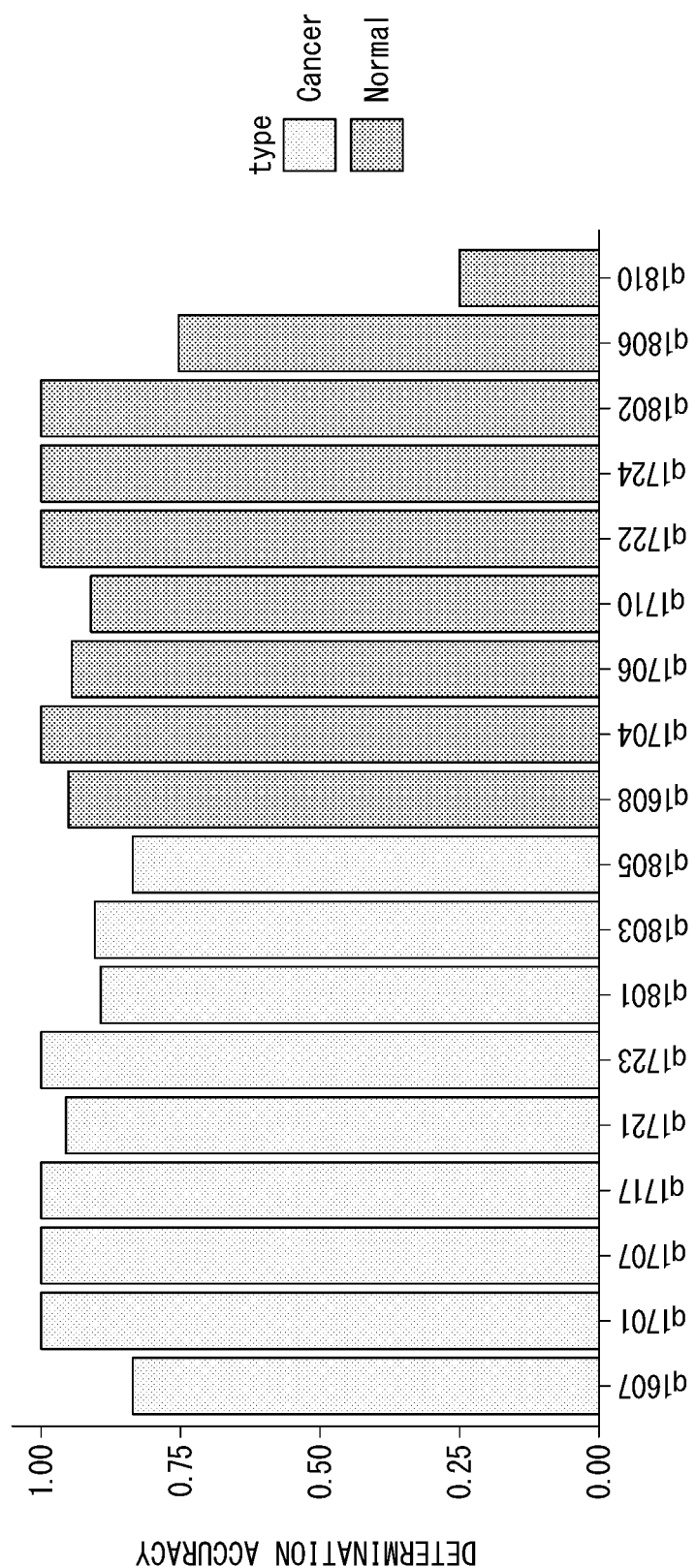
FIG. 13 is a diagram showing an example of a determination result according to the first embodiment.

FIG. 13 is a diagram showing an example of a determination result A according to the embodiment. Determination accuracy is expressed by percentage as a ratio of the number of determination Z stack captured images ZP1 in which a correct determination result is calculated to the number of determination Z stack captured images ZP1 used in the determination process. A sample "q1607" in FIG. 13 is a sample used for the determination and determination accuracy for the sample "q1607" was 83.3 percent.

In FIG. 13, determination accuracy of each sample is indicated for the learning Z stack captured images ZP1 including the THG images of cancer tissues and the THG images of normal tissues. In FIG. 13, the average of the determination accuracy for all the Z stack captured images ZP1 on which the calculation of the accuracy is repeated by the number of samples using a certain sample as a determination sample and using the other samples as learning samples was 90.1 percent. The uterine cancer determination device 1 can determine the likelihood that the uterine tissue is a cancer tissue at the determination accuracy of about 90 percent.

Conclusion

As described above, the uterine cancer determination device 1 according to the embodiment includes the THG image acquisition unit 100 and the cancer tissue determination unit 14.

The THG image acquisition unit 100 acquires the third harmonic images (in this example, the Z stack THG images ZT1) of the uterine tissue of the examinee obtained by the multiphoton microscope 2.

The cancer tissue determination unit 14 determines the likelihood that the uterine tissue of the examinee is a cancer tissue based on the states of the cell nuclei in the third harmonic images (in this example, the Z stack THG images ZT1) of the uterine tissue of the examinee.

In this configuration, the uterine cancer determination device 1 according to the embodiment can determine the likelihood that the uterine tissue of the examinee is a cancer tissue based on the states of the cell nuclei in the third harmonic images of the uterine tissue of the examinee. Therefore, it is possible to determine the likelihood that the uterine tissue is a cancer tissue without dyeing the uterine tissue.

In the uterine cancer determination device 1 according to the embodiment, the state of the cell nucleus is at least one selected from a group formed of the areas of the cell nuclei, the density of the cell nuclei, the shapes of the cell nuclei, and states of nucleoli.

In this configuration, the uterine cancer determination device 1 according to the embodiment can determine the likelihood that the uterine tissue of the examinee is a cancer tissue based on at least one selected from a group formed of the areas of the cell nuclei, the density of the cell nuclei, the shapes of the cell nuclei, and the states of nucleoli in the third harmonic images of the uterine tissue of the examinee. Therefore, it is possible to determine the likelihood that the uterine tissue is a cancer tissue with accuracy higher than in a case which is not based on at least one selected from the group.

In the uterine cancer determination device 1 according to the embodiment, the cancer tissue determination unit 14 determines that the likelihood that the uterine tissue of the examinee is a cancer tissue is high when at least one of the followings is satisfied:

(i) the average of the areas of the cell nuclei is larger than in normal uterine tissues;

(ii) the variation in the areas of the cell nuclei is greater than in the normal uterine tissues;

(iii) the density of the cell nuclei is higher than in the normal uterine tissues;

(iv) the variation in the density of the cell nuclei is greater than in the normal uterine tissues;

(v) the distortion of the shapes of the cell nuclei is greater than in the normal uterine tissues; and (vi) the variation in the shapes of the cell nuclei is greater than in the normal uterine tissues.

In this configuration, the uterine cancer determination device 1 according to the embodiment can determine the likelihood that the uterine tissue is a cancer tissue based on the features (i) to (vi) matching the pathological knowledge about the cell nuclei of a cancer tissue in the uterine tissue. Therefore, it is possible to determine the likelihood that the uterine tissue is a cancer tissue with accuracy higher than in a case which is not based on the features (i) to (vi).

In the uterine cancer determination device 1 according to the embodiment, the uterine tissue of the examinee is exposed to acetic acid in advance.

In this configuration, the uterine cancer determination device 1 according to the embodiment can image the cell nuclei in the third harmonic images of the uterine tissue of the examinee more clearly than in a case which the uterine tissue is not exposed to acetic acid in advance. Therefore, it is possible to determine the likelihood that the uterine tissue is a cancer tissue with accuracy higher than in a case which the uterine tissue is not exposed to acetic acid in advance.

In the uterine cancer determination device 1 according to the embodiment, the cancer tissue determination unit 14 determines the likelihood that the uterine tissue of the examinee is a cancer tissue based on the states of the cell nuclei in third harmonic images (in this example, the Z stack THG images ZT1) of the uterine tissue of the examinee with reference to the classification model M1 learned using the learning third harmonic images of normal uterine tissues obtained with the multiphoton microscope 2 and/or the learning third harmonic images of uterine cancer tissues obtained with the multiphoton microscope 2.

In this configuration, the uterine cancer determination device 1 according to the embodiment can determine the likelihood that the uterine tissue of the examinee is a cancer tissue with reference to the classification model M1. Therefore, it is possible to determine the likelihood that the uterine tissue is a cancer tissue with accuracy higher than in a case in which the classification model M1 is not referred to.

In the uterine cancer determination device 1 according to the embodiment, the learning third harmonic images are a plurality of cross-sectional images of a uterine epithelial tissue.

In this configuration, the uterine cancer determination device 1 according to the embodiment can perform learning using the plurality of cross-sectional images of the uterine epithelial tissue. Therefore, it is possible to determine the likelihood that the uterine tissue is a cancer tissue with accuracy higher than in a case in which one cross-sectional image is used for learning.

In the uterine cancer determination device 1 according to the embodiment, the third harmonic images (in this example, the Z stack THG images ZT1) of the uterine tissue of the examinee are a plurality of cross-sectional images of the uterine epithelial tissue of the examinee.

In this configuration, the uterine cancer determination device 1 according to the embodiment can determine the likelihood that the uterine tissue is a cancer tissue in each depth direction of the uterine epithelial tissue of the examinee. Therefore, it is possible to determine the likelihood that the uterine tissue is a cancer tissue with accuracy higher than in a case in which one cross-sectional image is used for the determination.

In the uterine cancer determination device 1 according to the embodiment, the cancer tissue determination unit 14 determines the likelihood that the uterine tissue is a cancer tissue in each of the plurality of third harmonic images (in this example, the Z stack THG images ZT1) of the uterine tissue of the examinee and calculates the likelihood that the uterine tissue of the examinee is a cancer tissue based on the ratio of the third harmonic images in which the likelihood that the uterine tissue is a cancer tissue is determined to be high to all the third harmonic images (in this example, the Z stack THG images ZT1).

In this configuration, the uterine cancer determination device 1 according to the embodiment can calculate the likelihood that the uterine tissue of the examinee is a cancer tissue based on the ratio of the third harmonic images in which the likelihood that the uterine tissue is a cancer tissue is determined to be high to the plurality of third harmonic images of the uterine tissue of the examinee. Therefore, it is possible to calculate the likelihood that the uterine tissue is a cancer tissue in the whole depth direction of the uterine tissue of the examinee.

Second Embodiment

Hereinafter, a second embodiment will be described in detail with reference to the drawings.

In the foregoing first embodiment, the uterine cancer determination device in which the nucleus region images are generated from the THG images based on a nucleus determination manipulation received from the user has been described. In the embodiment, a uterine cancer determination device in which nucleus regions are determined among the regions included in the THG images based on machine learning and nucleus region images are generated will be described.

The uterine cancer determination process according to the embodiment is referred to as a uterine cancer determination device 1a.

Configuration of Uterine Cancer Determination Device

Figure 14:
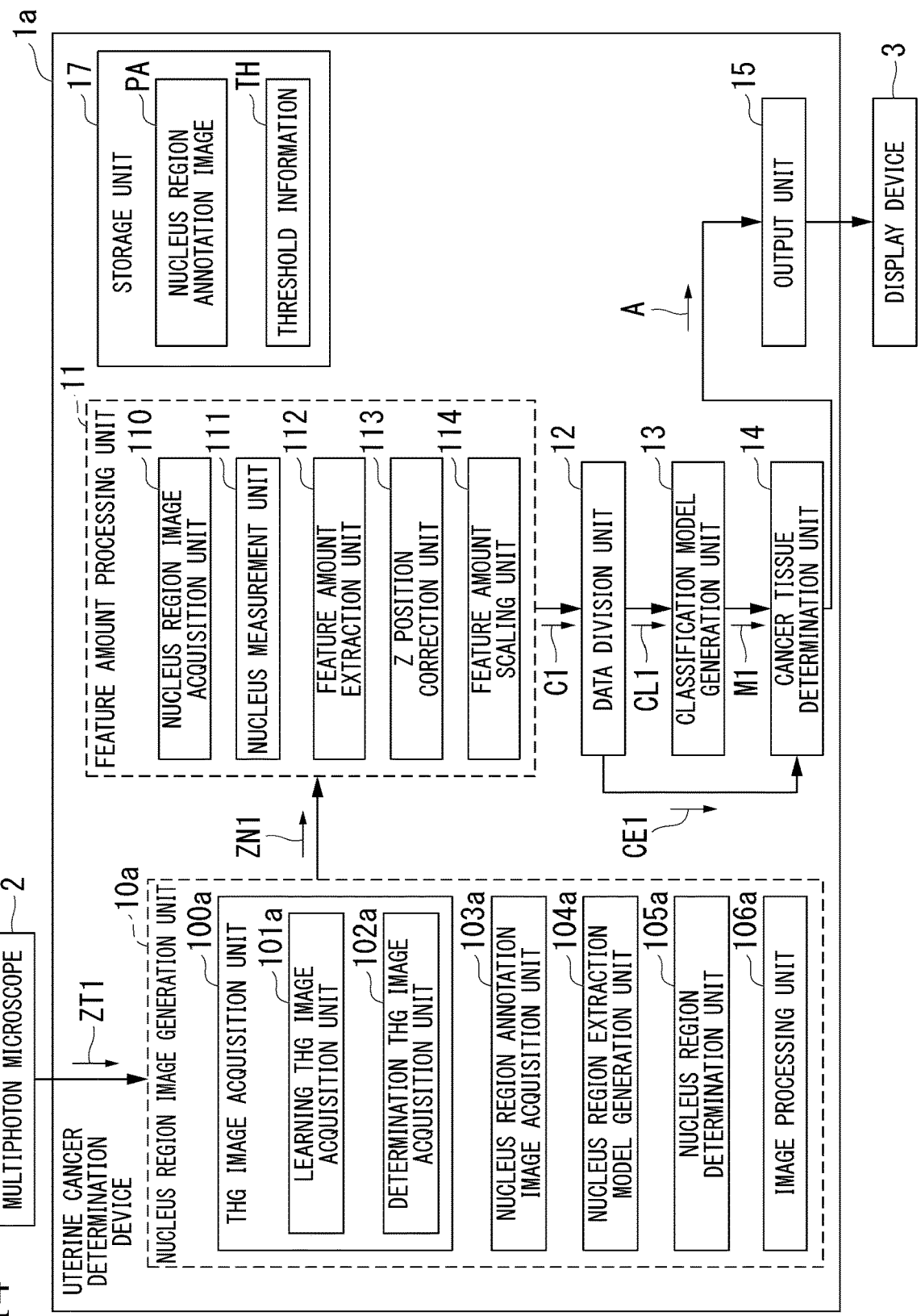
FIG. 14 is a diagram showing an example of a uterine cancer determination device according to a second embodiment.

FIG. 14 is a diagram showing an example of the uterine cancer determination device 1a according to the embodiment. The uterine cancer determination device 1a (see FIG. 14) according to the embodiment differs from the uterine cancer determination device 1 (see FIG. 4) according to the first embodiment in that a nucleus region image generation unit 10a and a storage unit 17 instead of the manipulation input unit 16 are included. Here, functions of other constituent elements (the feature amount processing unit 11, the data division unit 12, the classification model generation unit 13, the cancer tissue determination unit 14, and the output unit 15) are the same as those of the first embodiment. The description of the functions which are the same as those of the first embodiment will be omitted and differences from the first embodiment will be described mainly in the second embodiment.

The uterine cancer determination device 1a includes the nucleus region image generation unit 10a, the feature amount processing unit 11, the data division unit 12, the classification model generation unit 13, the cancer tissue determination unit 14, the output unit 15, and the storage unit 17.

The nucleus region image generation unit 10a generates Z stack nucleus region images ZN1a from the Z stack captured images ZP1 based on machine learning. Here, the machine learning used by the nucleus region image generation unit 10a is, for example, deep learning.

Figure 15:
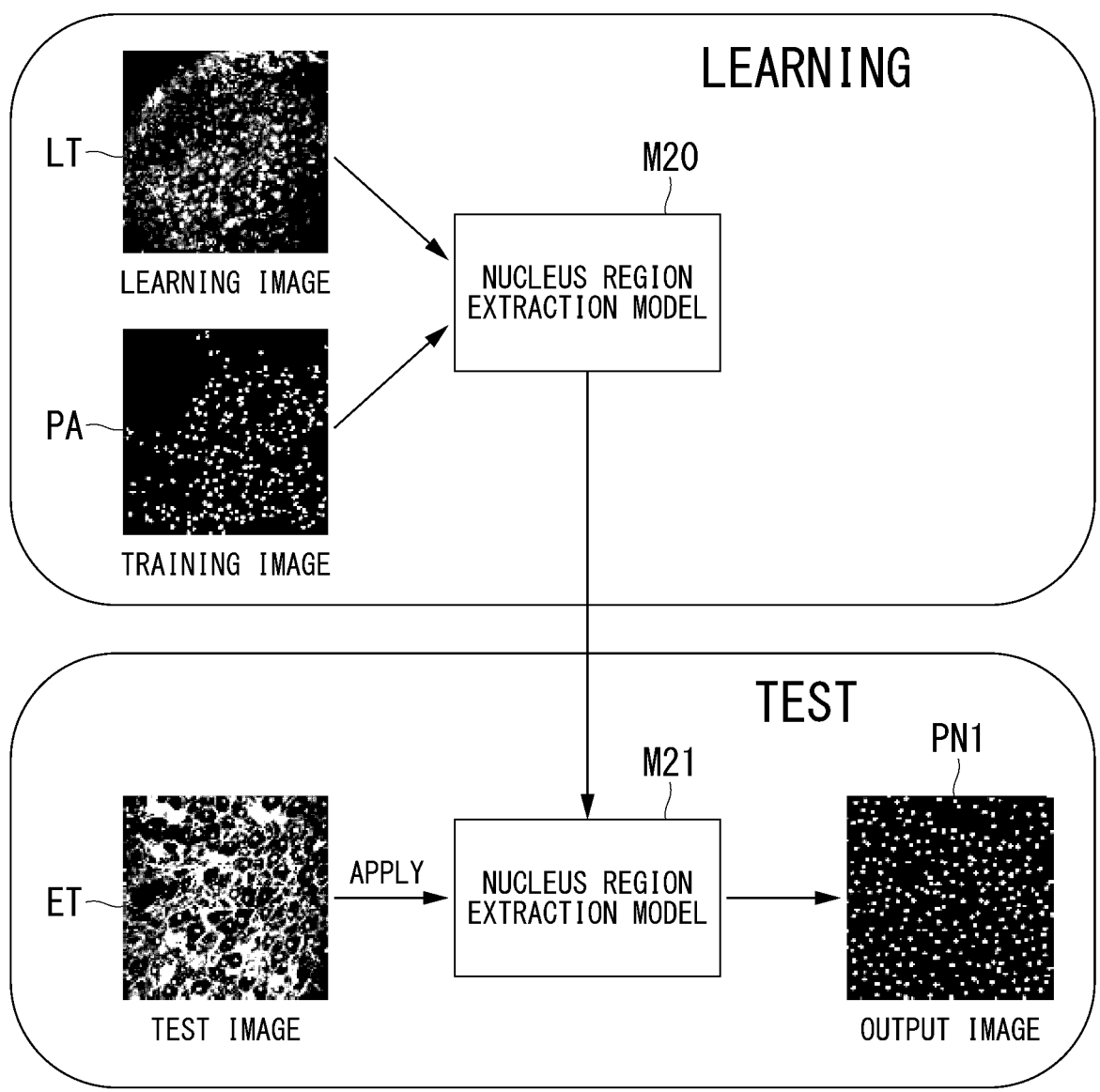
FIG. 15 is a diagram showing an example of deep learning used by a nucleus region image generation unit according to the second embodiment.

Here, an overview of the deep learning used by the nucleus region image generation unit 10a will be described with reference to FIG. 15. FIG. 15 is a diagram showing an example of the deep learning used by the nucleus region image generation unit 10a according to the embodiment.

The nucleus region image generation unit 10a uses, for example, U-Net which known as an architecture of the deep learning as the nucleus region extraction model is M20. U-net is a convolutional neural network (CNN) and high accuracy is reported in segmentation of medical image. By using U-Net, it is possible to ascertain features of a whole image and it is possible to minimize an error of a correct solution image (a distribution of cell nuclei and non-cell nuclei) at a multiple solution in the whole image. In U-Net, all the layers are configured with convolution layers and an Up-Cony layer is included toward an output layer.

As a parameter of the nucleus region extraction model M20, an input size is 512×512 which is a size of an image of the Z stack captured image ZP1.

The nucleus region image generation unit 10a performs learning using a learning Z stack THG image LT and a nucleus region annotation image PA based on the nucleus region extraction model M20. Here, the nucleus annotation image PA is an image indicating a nucleus region of each of a plurality of THG images included in the learning Z stack THG images LT.

The nucleus region image generation unit 10a generates a nucleus region extraction model M21 as a result obtained by performing learning. The nucleus region image generation unit 10a applies the generated nucleus region extraction model M21 to determination Z stack THG images ET and outputs the nucleus region images PN1 which are images in which the nucleus regions of the determination Z stack THG images ET are determined.

Referring back to FIG. 14, the description of the configuration of the uterine cancer determination device 1a will continue.

The nucleus region image generation unit 10a includes a THG image acquisition unit 100a, a nucleus region annotation image acquisition unit 103a, a nucleus region extraction model generation unit 140a, a nucleus region determination unit 105a, and an image processing unit 106a.

The THG image acquisition unit 100a acquires the Z stack captured images ZP1. The THG image acquisition unit 100a includes a learning THG image acquisition unit 101a and a determination THG image acquisition unit 102a. As the Z stack captured images ZP1 acquired by the THG image acquisition unit 100a, there are the learning Z stack THG images LT and the determination Z stack THG images ET.

The learning THG image acquisition unit 101a acquires the learning Z stack THG images LT.

The determination THG image acquisition unit 102a acquires the determination Z stack THG images ET.

The nucleus region annotation image acquisition unit 103a acquires the nucleus region annotation image PA from the storage unit 17.

The nucleus region extraction model generation unit 140a performs the learning using the learning Z stack THG images LT and the nucleus region annotation images PA based on the nucleus region extraction model M20 to generate the nucleus region extraction model M21 as a learning result.

The nucleus region determination unit 105a determines the nucleus regions of the determination Z stack THG images ET based on the nucleus region extraction model M21 generated by the nucleus region extraction model generation unit 140a.

The image processing unit 106a generates the Z stack nucleus region images ZN1a based on the determination result of the nucleus region determination unit 105a.

The storage unit 17 stores various kinds of information. The various kinds of information include the nucleus region annotation images PA and threshold information TH. The threshold information TH is information indicating various thresholds used in image processing performed by the image processing unit 106a.

Nucleus Region Image Generation Process

Next, details of the nucleus region image generation process in which the uterine cancer determination device 1a generates the Z stack nucleus region images ZN1a will be described. As the nucleus region image generation process, there are a nucleus region learning process of generating the nucleus region extraction model M21 and a nucleus region determination process of determining a nucleus region based on the nucleus region extraction model M21.

Figure 16:
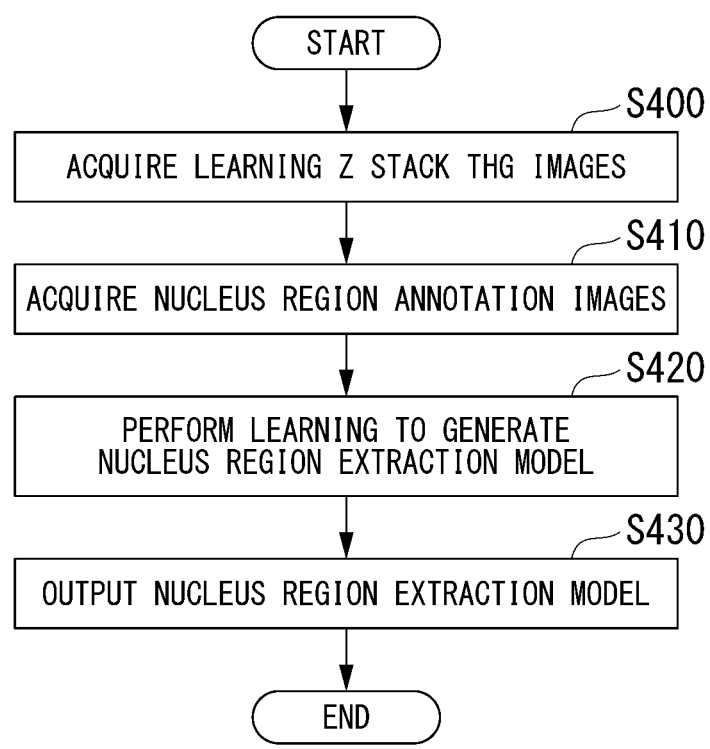
FIG. 16 is a diagram showing an example of a nucleus region learning process according to the second embodiment.

FIG. 16 is a diagram showing an example of a nucleus region learning process according to the embodiment.

Step S400: the learning THG image acquisition unit 101a acquires the learning Z stack THG images LT. The learning THG image acquisition unit 101a supplies the acquired learning Z stack THG images LT to the nucleus region extraction model generation unit 140a.

Step S410: the nucleus region annotation image acquisition unit 103a acquires the nucleus region annotation images PA from the storage unit 17. The nucleus region annotation image acquisition unit 103a supplies the acquired nucleus region annotation images PA to the nucleus region extraction model generation unit 140a.

Step S420: the nucleus region extraction model generation unit 140a performs learning using the learning Z stack THG images LT supplied from the learning THG image acquisition unit 101a and the nucleus region annotation images PA supplied from the nucleus region annotation image acquisition unit 103a based on the nucleus region extraction model M20 to generate the nucleus region extraction model M21 as a learning result. Here, the nucleus region extraction model generation unit 140a changes a weight between nodes of the nucleus region extraction model M20 based on the learning Z stack THG images LT and the nucleus region annotation images PA to generate the nucleus region extraction model M21.

Step S430: the nucleus region extraction model generation unit 140a outputs the generated nucleus region extraction model M21 to the nucleus region determination unit 105a.

Figure 17:
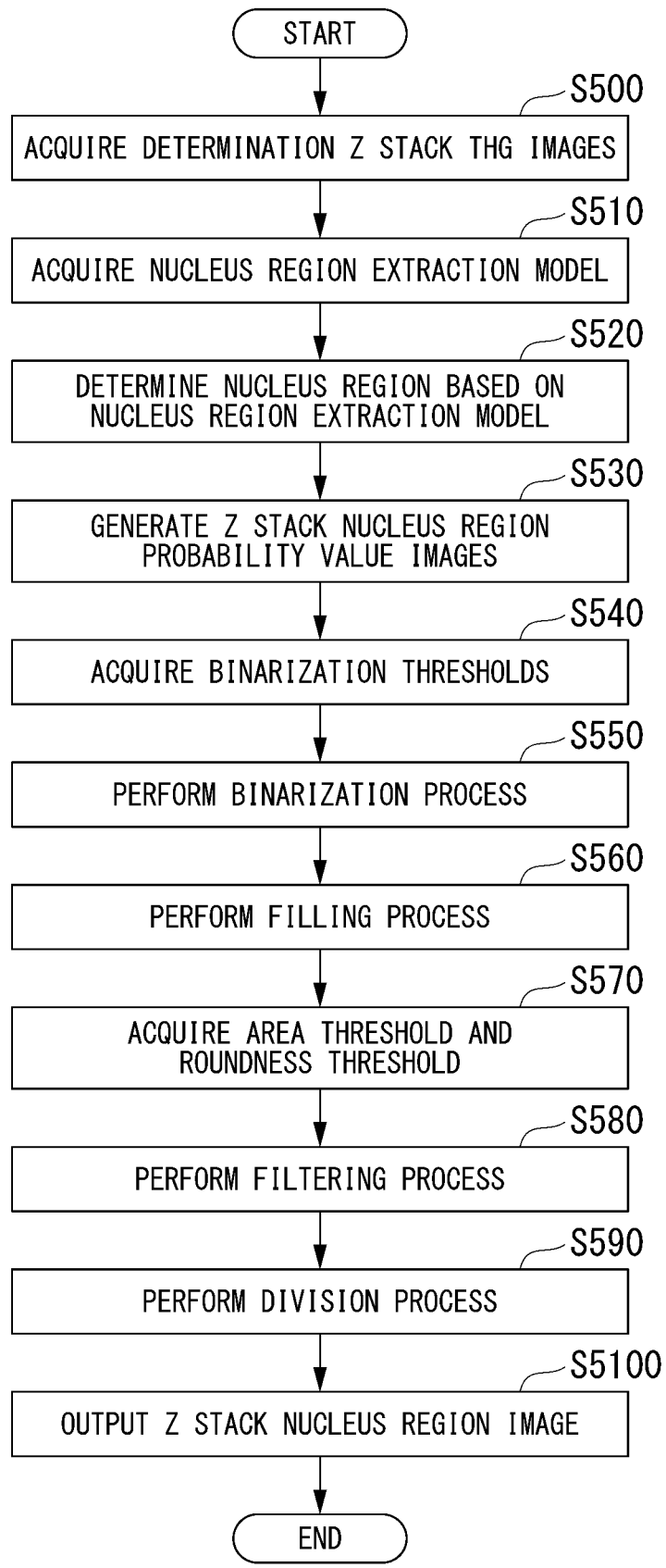
FIG. 17 is a diagram showing an example of a nucleus region determination process according to the second embodiment.

Next, the nucleus region determination process will be described with reference to FIG. 17. FIG. 17 is a diagram showing an example of the nucleus region determination process according to the embodiment.

Step S500: the determination THG image acquisition unit 102a acquires the determination Z stack THG images ET. The determination THG image acquisition unit 102a supplies the acquired determination Z stack THG images ET to the nucleus region determination unit 105a.

Step S510: the nucleus region determination unit 105a acquires the nucleus region extraction model M21 output from the nucleus region extraction model generation unit 140a.

Step S520: the nucleus region determination unit 105a determines nucleus regions in the determination Z stack THG images ET supplied from the determination THG image acquisition unit 102a based on the acquired nucleus region extraction model M21. Here, the nucleus region determination unit 105a determines nucleus regions for each of pixels of the plurality of THG images PTi included in the determination Z stack THG images ET. The nucleus region determination unit 105a causes a probability value indicating the likelihood that there are the nucleus regions to correspond to each of the pixels of the plurality of THG images PTi as a determination result.

The nucleus region determination unit 105a supplies the determination result of the nucleus regions to the image processing unit 106a.

Step S530: the image processing unit 106a generates Z stack nucleus region probability value images based on the determination result of the nucleus images supplied from the nucleus region determination unit 105a. The Z stack nucleus region probability value images are images in which probability values indicating likelihoods of the nucleus regions in each of the pixels of the THG images PTi. Here, the probability values indicating the likelihoods of the nucleus regions are shown, for example, with gray scales.

Step S540: the image processing unit 106a acquires binarization thresholds from the storage unit 17. Here, the binarization thresholds are included in the threshold information TH.

Step S550: the image processing unit 106a performs a binarization process. The image processing unit 106a performs the binarization process on the generated Z stack nucleus region probability value images based on the acquired binarization thresholds. The image processing unit 106a generates Z stack binarized images from the Z stack nucleus region probability value images through the binarization process.

Here, when the probability value indicating the likelihood of the nucleus region is equal to or greater than the binarization threshold in each pixel of the Z stack nucleus region probability value images, the image processing unit 106a allocates, for example, one luminance value of 1 (for example, a luminance value corresponding to white) between binary values of luminance to the pixels. When the probability value indicating the likelihood of the nucleus region is less than the binarization threshold in each pixel of the Z stack nucleus region probability value images, the image processing unit 106a allocates the other luminance value of 2 (for example, a luminance value corresponding to black) between the binary values of luminance to the pixels.

Step S560: the image processing unit 106a performs a filling process on the generated Z stack binarized images. Here, the image processing unit 106a uses, for example, closing or opening as the filling process. The image processing unit 106a generates Z stack filled images from the Z stack binarized images through the filling process.

Step S570: the image processing unit 106a acquires an area threshold and a roundness threshold from the storage unit 17. Here, the area threshold and the roundness threshold are included in the threshold information TH.

Step S580: the image processing unit 106a performs the filtering process. The image processing unit 106a performs the filtering process on the generated Z stack filled images based on the acquired area threshold and roundness threshold.

Here, the image processing unit 106a pairs adjacent pixels among the pixels to which the luminance value of 1 is applied (for example, pixels to which white is allocated) included in the Z stack filled images and determines candidate regions which are candidates for the nucleus regions. The image processing unit 106a determines the candidate region even when only one pixel is isolated.

The image processing unit 106a measures an area and roundness of each of the determined candidate regions. When the measured area is equal to or greater than the area threshold and the measured roundness is equal to or greater than the roundness threshold in a certain candidate region, the image processing unit 106a determines that this candidate region is not excluded. Conversely, when the measured area is less than the area threshold or the measured roundness is less than the roundness threshold in a certain candidate region, the image processing unit 106a determines that this candidate region is excluded.

The image processing unit 106a changes a luminance value of the pixel included in the candidate region determined to be excluded to the luminance value of 2 among the candidate regions included in the Z stack filled images. For example, when the candidate region is white, the image processing unit 106a sets black in the candidate region determined to be excluded.

Step S590: the image processing unit 106a performs a division process. The image processing unit 106a performs the division process on the Z stack filled image on which the filtering process has been performed. The image processing unit 106a uses, for example, WaterShed as a scheme for the division process. The image processing unit 106a determines a contour of the nucleus region through the division process and divides a region of the Z stack filled image on which the filtering process has been performed into a nucleus region and a region other than the nucleus region.

The image processing unit 106a generates a Z stack nucleus region image ZN1a as a result of the division process.

Step S5100: the image processing unit 106a outputs the generated Z stack nucleus region image ZN1a to the feature amount processing unit 11.

Then, the nucleus region image generation unit 10a ends the nucleus region determination process.

Figure 20:
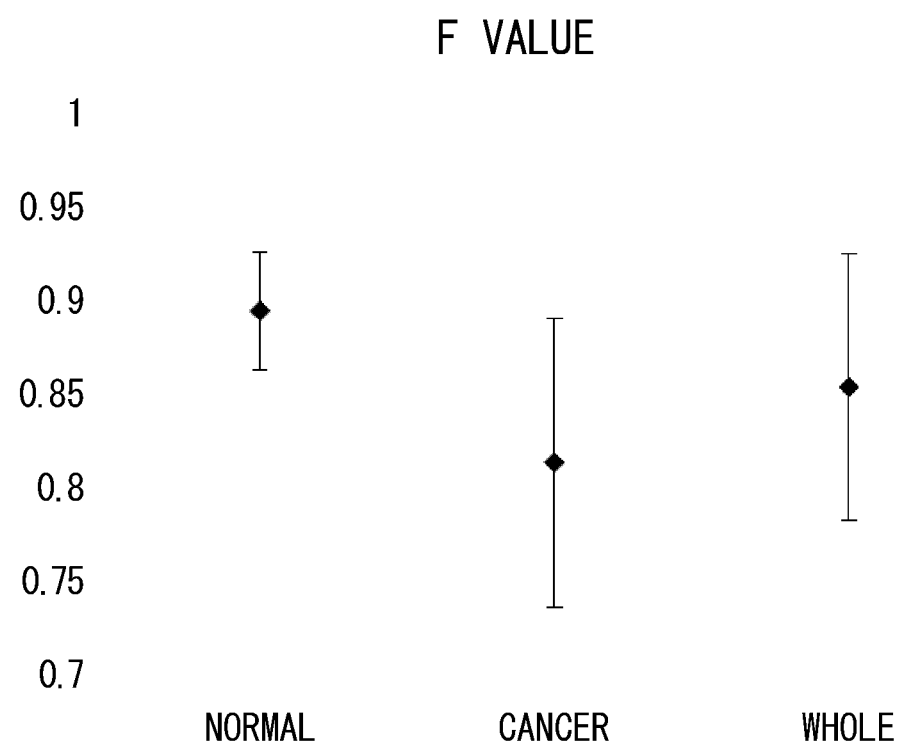
FIG. 20 is a diagram showing an example of an F value in a whole Z stack nucleus region image according to the second embodiment.

A result of the nucleus region determination process will be described with reference to FIGS. 18 to 20.

Figure 18:
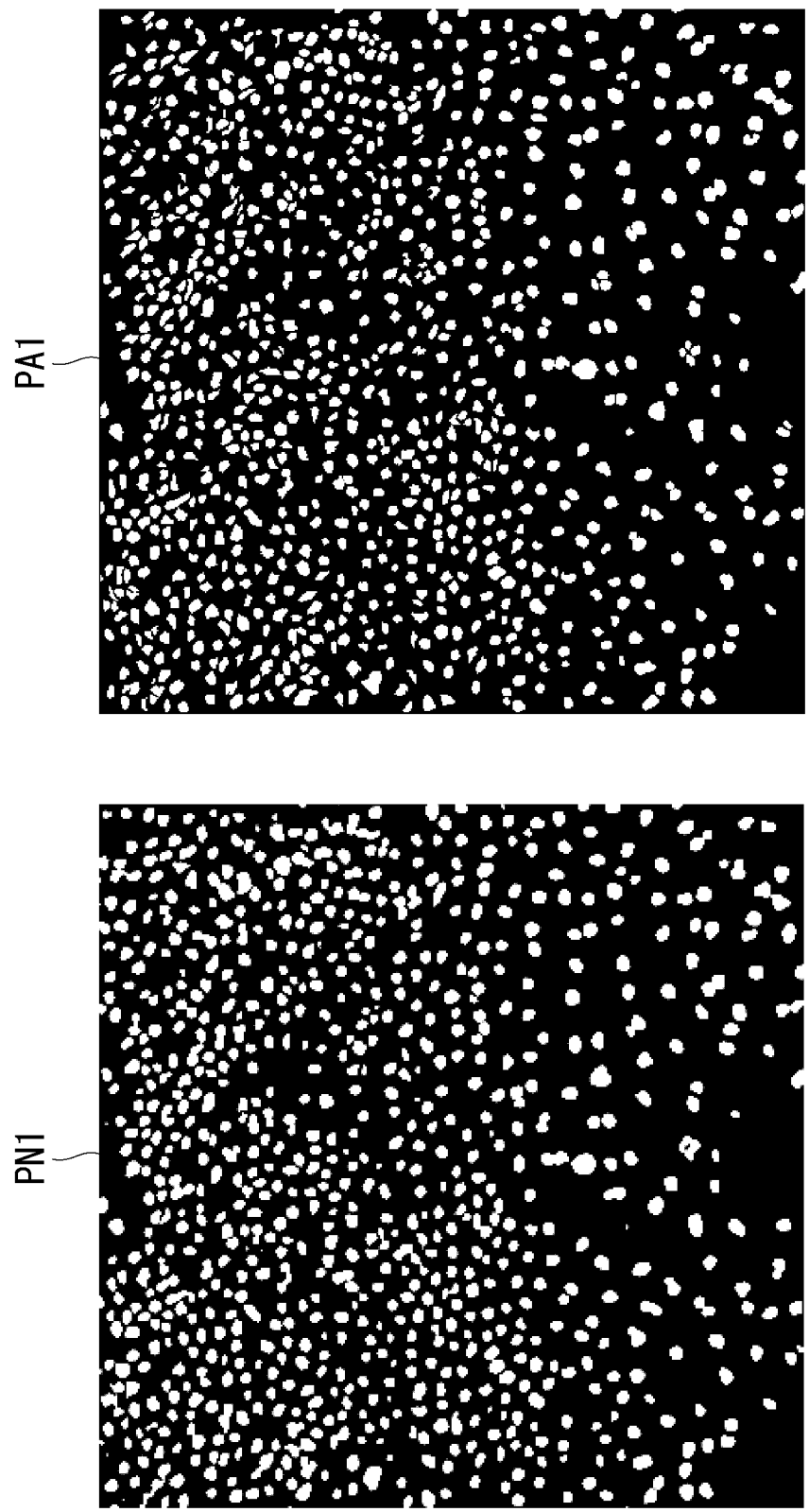
FIG. 18 is a diagram showing examples of a nucleus region image and a nucleus region annotation image according to the second embodiment.

FIG. 18 is a diagram showing examples of a nucleus region image and a nucleus region annotation image according to the embodiment. In FIG. 18, a nucleus region image PNj is illustrated as an example of the nucleus region image obtained through the nucleus region determination process. A nucleus region annotation image PAj is a nucleus region annotation image used to generate the nucleus region image PNj.

Next, determination accuracy of the nucleus region determination process will be described with reference to FIG. 19.

FIG. 19 is a diagram showing an example of a result of a nucleus region determination process according to the embodiment. As the nucleus regions indicated in the nucleus region images obtained through the nucleus region determination process, there are first and second regions. The first region is a region which coincides with the nucleus region indicated in the nucleus region annotation image. The second region is a region which is erroneously determined and does not coincide with the nucleus region indicated in the nucleus region annotation image. On the other hand, as a nucleus region indicated in the nucleus region annotation image, there is a third region which is a region not included in the nucleus region of the nucleus region image omitted from the determination.

In FIG. 19, the first and second regions are distinguished in the nucleus region images obtained through the nucleus region determination process, and images PC1 and PC2 to which the third region is further added are illustrated. The image PC1 is a nucleus region image of a normal tissue. The image PC2 is a nucleus region image of a cancer tissue.

Here, determination accuracy of the nucleus region determination process is evaluated using an F value. The F value is the harmonic mean of the precision ratio and the recall ratio and takes a value in a range from 0 to 1. As the F value is closer to 1, determination accuracy is higher. The precision ratio is a ratio of the number of first regions to the number of extracted nucleus regions (the first and second regions). The recall ratio is a ratio of the number of first regions to the number of nucleus regions (the first and third regions) indicated in the nucleus region annotation image.

By using the F value, it is possible to calculate determination accuracy which does not depend on a ratio of an area occupied by the nucleus region in the nucleus region image to an area occupied by a background other than the nucleus region.

An F value of the image PC1 was 0.932 and an F value of the image PC2 was 0.909.

Next, an F value in the whole Z stack nucleus region image ZN1a will be described with reference to FIG. 20. FIG. 20 is a diagram showing an example of an F value in the whole Z stack nucleus region image ZN1a according to the embodiment. An average F value in the whole Z stack nucleus region image ZN1a was 0.854. In the uterine cancer determination device 1a, the nucleus regions are extracted with high accuracy in both the images PC1 and PC2.

Figure 21:
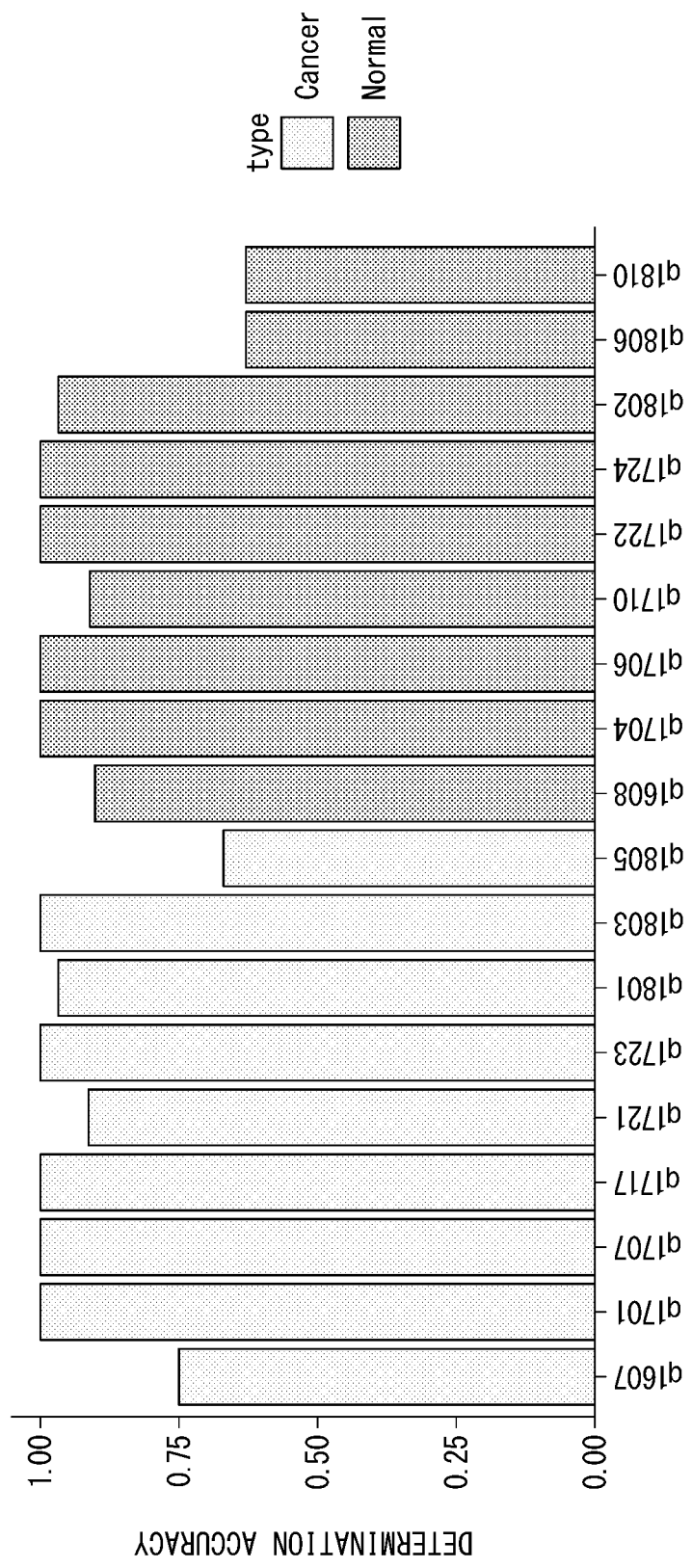
FIG. 21 is a diagram showing an example of a determination result according to the second embodiment.

Next, a determination result Aa of a uterine cancer determination process of the uterine cancer determination device 1a will be described with reference to FIG. 21. FIG. 21 is a diagram showing an example of the determination result Aa according to the embodiment. The uterine cancer determination process of the uterine cancer determination device 1a is a uterine cancer determination process when the Z stack nucleus region image ZN1a is generated through the nucleus region determination process. When the uterine cancer determination process ends, the uterine cancer determination device 1a performs the uterine cancer determination process by performing processes similar to the learning process of FIG. 10 and the determination process of FIG. 12, as described above.

The average of the determination accuracy of all the Z stack captured images ZP1 obtained by setting a certain sample as a determination sample, setting the others as learning samples, and repeating the calculation of the accuracy by the number of samples was 90.7 percent. The uterine cancer determination device 1a can determine the likelihood that the uterine tissue is a cancer tissue with the determination accuracy of about 90 percent even when the Z stack nucleus region images ZN1a is generated through the nucleus region determination process.

Conclusion

As described above, the uterine cancer determination device 1a according to the embodiment includes the nucleus region image generation unit 10a. The nucleus region image generation unit 10a generates the Z stack nucleus region images ZN1a which are a plurality of images in which the regions indicating the cell nuclei of the uterine tissue are determined from the Z stack captured images ZP1 based on the machine learning.

In this configuration, the uterine cancer determination device 1a according to the embodiment can generate the Z stack nucleus region images ZN1a based on the machine learning. Therefore, it is possible to reduce time and effort for determining the regions indicating the cell nuclei of the uterine tissue from the Z stack captured images ZP1.

Third Embodiment

Hereinafter, a third embodiment will be described in detail with reference to the drawings.

In the first and second embodiments, the uterine cancer determination device which determines the likelihood that the uterine tissue of the examinee is a cancer tissue based on the THG images has been described. In the embodiment, a uterine cancer determination device that determines cancer progress of a uterine tissue highly likely to be a cancer tissue based on the THG images based on second harmonic images will be described.

A uterine cancer determination system according to the embodiment is referred to as a uterine cancer determination system STb. A uterine cancer determination device according to the embodiment is referred to as a uterine cancer determination device 1b and a multiphoton microscope is referred to as a multiphoton microscope 2b.

When a tumor develops, fibrosis occurs in a surrounding tissue. Fibers occurring due to the fibrosis are formed from molecules containing various kinds of collagen. In some fibrillar collagen, SHG occurs. The multiphoton microscope 2b according to the embodiment images a uterine tissue using SHG to generate second harmonic images in addition to THG images. The second harmonic image is an image of a cross section of a uterine tissue generated based on light generated in second harmonic generation caused by interaction between the uterine tissue and excitation light emitted from an irradiation unit of the multiphoton microscope 2b.

In the embodiment, captured images included in the Z stack captured images include the THG images and the second harmonic images which are images obtained by imaging the uterine tissue using SGH. Hereinafter, the second harmonic images are referred to as SHG images. The Z stack captured images of the SHG images are referred to as Z stack SHG images ZS1. That is, the Z stack SHG images ZS1 are a plurality of SHG images obtained by imaging the uterine tissue using SHG while changing the distance from the uterine tissue in the Z axis direction.

Each of a plurality of images included in the Z stack SHG images ZS1 are expressed as SHG images PSi (where i=1, 2, . . . , N: N is the number of images included in the Z stack SHG images ZS1) or the like.

The multiphoton microscope 2b captures the THG images and the SHG images at each depth of the uterine tissue. The SHG images PSi included in the Z stack SHG images ZS1 and the THG images PTi included in the Z stack THG images ZT1 are images captured at the common depths of the uterine tissue and correspond to each other.

Figure 22:
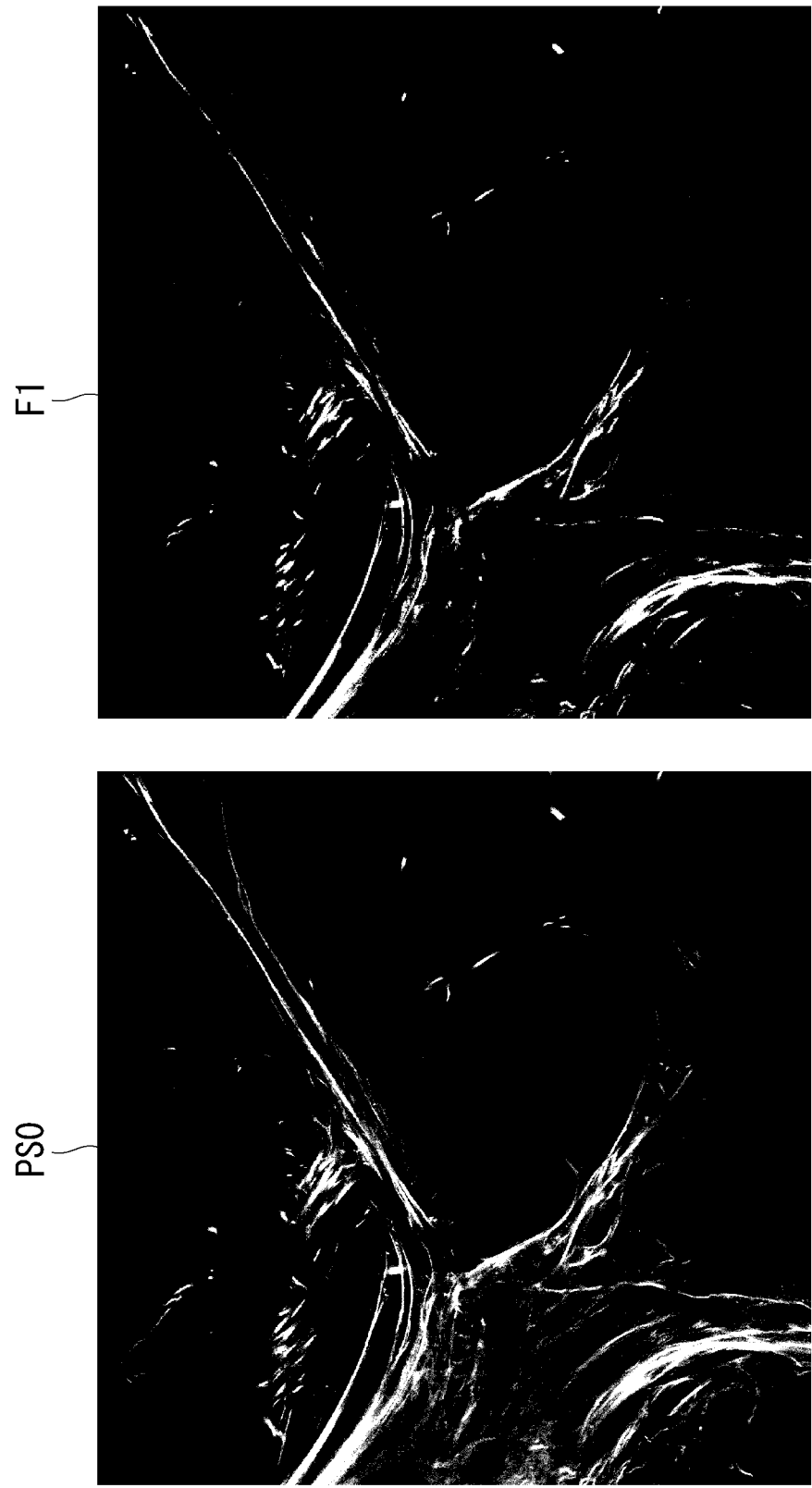
FIG. 22 is a diagram showing an example of a second harmonic image according to a third embodiment.

Here, the SHG images captured by the multiphoton microscope 2b will be described with reference to FIG. 22. FIG. 22 is a diagram showing an example of an SHG image PS0 according to the embodiment. In FIG. 22, a fiber-like structure image F1 is illustrated along with the SHG image PS0 for comparison. The fiber-like structure image F1 is an image detected and extracted from the SHG image PS0 by machine learning. In the SHG image PS0 captured by the multiphoton microscope 2b, it can be understood that a fiber-like structure is imaged to the same degree as that of a fiber-like structure imaged in the fiber-like structure image F1.

As a tumor develops, fibrosis spreads from a deep part to a superficial part of a uterine tissue.

Here, an aspect in which the fibrosis spreads from a deep part to a superficial part of a uterine tissue will be described with reference to FIG. 23. FIG. 23 is a diagram showing an example of a cross section of a uterine tissue at each stage of tumor progress according to the embodiment.

Figure 23A:
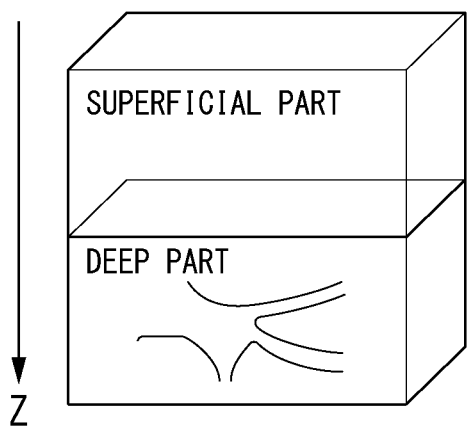
FIG. 23A is a diagram showing an example of a cross section of a uterine tissue at each stage of tumor progress according to the third embodiment.
Figure 23B:
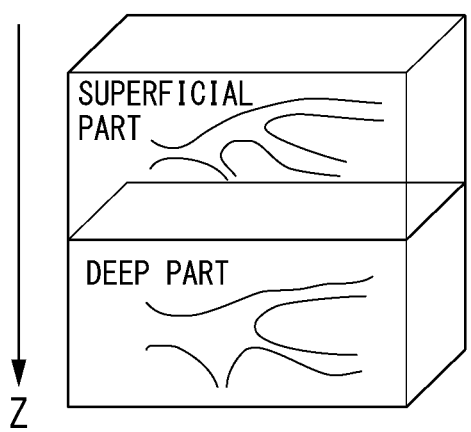
FIG. 23B is a diagram showing an example of a cross section of a uterine tissue at each stage of tumor progress according to the third embodiment.

In FIG. 23A, there is a fiber-like structure in the deep part of the uterine tissue. In FIG. 23B, fibrosis occurs in the superficial part on a cross section of the uterine tissue when the tumor develops.

In the embodiment, the Z axis is also set in a direction oriented inward from an epithelial tissue of the uterine tissue. As the tumor develops, the fibrosis spread from a part in which a value of the Z coordinate is large to a part in which a value of the Z coordinate is small in the uterine tissue.

In the superficial part of the uterine tissue, it is not known in advance at which depth the fibrosis occurs because of a difference in accordance with tumor progress. In the uterine cancer determination device $1b$, the fiber-like structure can also be extracted even when the fibrosis occurs at any depth of the superficial part of the tissue by using the Z stack SHG images ZS1.

Configuration of Uterine Cancer Determination Device

Figure 24:
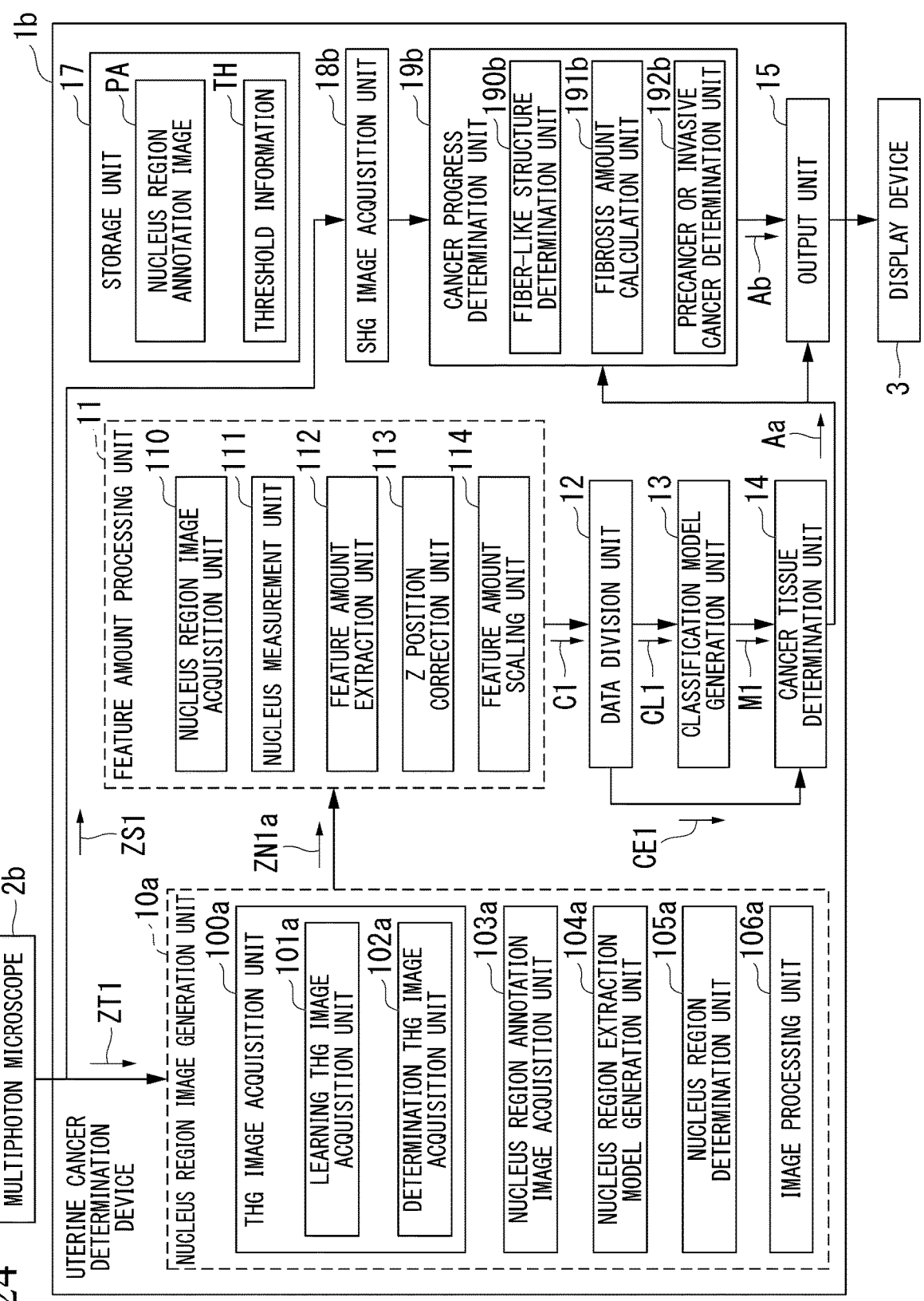
FIG. 24 is a diagram showing an example of a uterine cancer determination device according to the third embodiment.

FIG. 24 is a diagram showing an example of a uterine cancer determination device $1b$ according to the embodiment. The uterine cancer determination device $1b$ (see FIG. 24) according to the embodiment differs from the uterine cancer determination device $1a$ (see FIG. 14) according to the second embodiment that an SHG image acquisition unit $18b$ and a cancer progress determination unit $19b$. Here, functions of other constituent elements (nucleus region image generation unit $10a$, the feature amount processing unit $11$, the data division unit $12$, the classification model generation unit $13$, the cancer tissue determination unit $14$, and the output unit $15$) are the same as those of the second embodiment. The description of the functions which are the same as those of the second embodiment will be omitted and differences from the second embodiment will be described mainly in the third embodiment.

The uterine cancer determination device $1b$ classifies the stages of tumor progress by extracting a fiber-like structure feature from the Z stack SHG images ZS1 of the superficial part of the uterine tissue with the multiphoton microscope $2b$ and quantifying the fiber-like structure feature as a fibrosis amount. Here, the stages of tumor progress are classified into, for example, non-invasion and invasion. The non-invasion corresponds to a precancer and the invasion corresponds to an invasive cancer.

The uterine cancer determination device $1b$ includes the nucleus region image generation unit $10a$, the feature amount processing unit $11$, the data division unit $12$, the classification model generation unit $13$, the cancer tissue determination unit $14$, the output unit $15$, the storage unit $17$, the SHG image acquisition unit $18b$, and the cancer progress determination unit $19b$. The uterine cancer determination device $1b$ may include the nucleus region image generation unit $10$ as in the uterine cancer determination device $1$ (see FIG. 4) according to the first embodiment instead of the nucleus region image generation unit $10a$.

The SHG image acquisition unit $18b$ acquires the Z stack SHG images ZS1 captured by the multiphoton microscope $2b$.

The cancer progress determination unit $19b$ determines cancer progress based on the state of the fiber-like structure in the SHG images PSi included in the Z stack SHG image ZS1 when the likelihood that the uterine tissue of the examinee is a cancer tissue is determined to be high by the cancer tissue determination unit $14$.

The cancer progress determination unit $19b$ includes a fiber-like structure determination unit $190b$, a fibrosis amount calculation unit $191b$, and a precancer or invasive cancer determination unit $192b$.

The fiber-like structure determination unit $190b$ determines the fiber-like structure in the Z stack SHG images ZS1. Here, in the embodiment, the fiber-like structure determination unit $190b$ determines the fiber-like structure based on, for example, machine learning. The fiber-like structure determination unit $190b$ generates Z stack fiber-like structure images ZF1 from the Z stack SHG images ZS1 based on a determination result. The Z stack fiber-like structure image ZF1 is a Z stack image in which the fiber-like structure is shown.

Each of a plurality of images included in the Z stack fiber-like structure images ZF1 are referred to as fiber-like structure images PFi (where i=1, 2, . . . , N: N is the number of images included in the Z stack fiber-like structure images ZF1) or the like.

The fibrosis amount calculation unit $191b$ calculates a fibrosis amount of the superficial part of the uterine tissue captured as the Z stack SHG images ZS1 based on the Z stack fiber-like structure images ZF1 generated by the fiber-like structure determination unit $190b$.

The precancer or invasive cancer determination unit $192b$ determines whether the uterine tissue determined to be highly likely to be a cancer tissue is a precancer or an invasive cancer based on the fibrosis amount calculated by the fibrosis amount calculation unit $191b$.

Process of Uterine Cancer Determination System

Figure 25:
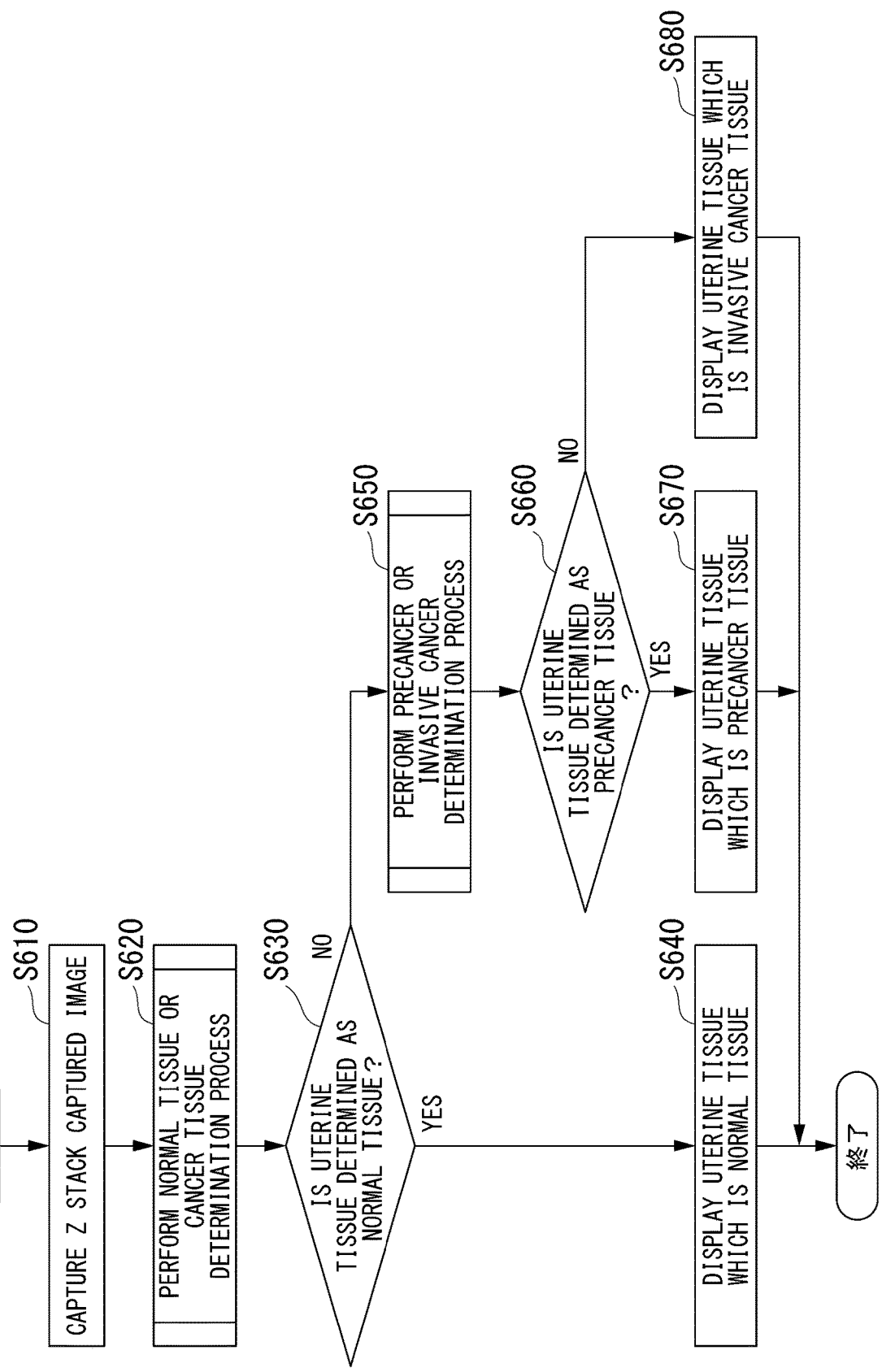
FIG. 25 is a diagram showing an example of a uterine cancer determination process according to the third embodiment.

Next, a uterine cancer determination process which is a process of a uterine cancer determination system STb will be described. FIG. 25 is a diagram showing an example of a uterine cancer determination process according to the embodiment.

Since each process of steps S610, S620, S630, and S640 is similar to each process of steps S10, S20, S30, and S40 in FIG. 7, description thereof will be omitted.

Step S650: the uterine cancer determination device $1b$ performs a precancer or invasive cancer determination process which is a process of determining whether the uterine tissue of the examinee is a precancer tissue or an invasive cancer tissue based on the Z stack SHG images ZS1 captured by the multiphoton microscope $2b$. The details of the precancer or invasive cancer determination process will be described below with reference to FIG. 26.

Step S660: the output unit $15$ of the uterine cancer determination device $1b$ performs a process based on a determination result Ab of the cancer progress determination unit $19b$. The determination result Ab indicates whether the uterine tissue of the examinee is a precancer or an invasive cancer. When the uterine tissue of the examinee is determined to be a precancer (YES in step S660), the output unit $15$ outputs a result indicating the uterine tissue of the examinee is a precancer to the display device $3$. Thereafter, the display device $3$ performs a process of step S670.

Conversely, when the uterine tissue of the examinee is not a precancer, that is, an invasive cancer (NO in step S660), the output unit $15$ outputs a result indicating that the uterine tissue of the examinee is an invasive cancer to the display device $3$.

Step S670: the display device 3 displays the result indicating that the uterine tissue of the examinee is a precancer.

Step S680: the display device 3 displays the result indicating that the uterine tissue of the examinee is an invasive cancer.

Then, the uterine cancer determination system STb ends the uterine cancer determination process.

Figure 26:
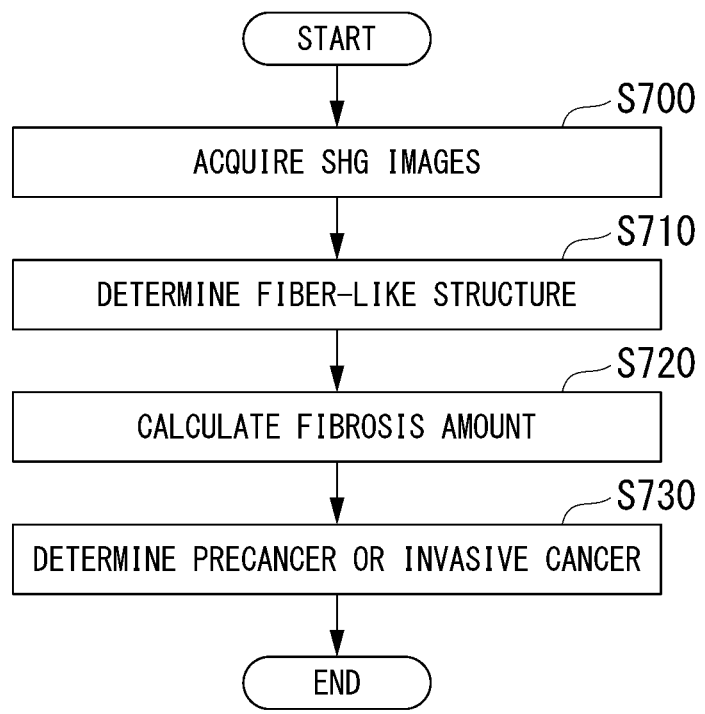
FIG. 26 is a diagram showing an example of a precancer or invasive cancer determination process according to the third embodiment.

Next, the precancer or invasive cancer determination process will be described with reference to FIG. 26. FIG. 26 is a diagram showing an example of a precancer or invasive cancer determination process according to the embodiment.

Step S700: the SHG image acquisition unit 18b acquires the Z stack SHG images ZS1 captured by the multiphoton microscope 2b. That is, the SHG image acquisition unit 18b acquires the second harmonic images of the uterine tissue of the examinee obtained by the multiphoton microscope 2b.

The SHG image acquisition unit 18b supplies the acquired Z stack SHG images ZS1 to the fiber-like structure determination unit 190b.

Step S710: the fiber-like structure determination unit 190b determines the fiber-like structure in the Z stack SHG image ZS1. The fiber-like structure determination unit 190b generates the Z stack fiber-like structure images ZF1 from the Z stack SHG images ZS1 based on a determination result. The fiber-like structure determination unit 190b supplies the generated Z stack fiber-like structure images ZF1 to the fibrosis amount calculation unit 191b.

Here, the fiber-like structure determination unit 190b performs determination based on, for example, machine learning. The fiber-like structure determination unit 190b uses, for example, U-Net as the machine learning.

Here, the fiber-like structure images PF1 included in the Z stack fiber-like structure images ZF1 generated by the fiber-like structure determination unit 190b will be described with reference to FIG. 27. FIG. 27 is a diagram showing an example of a fiber-like structure image PF1 according to the embodiment.

The fiber-like structure image PF1 is an image in which the fiber-like structure is determined based on the SHG image PS1 included in the Z stack SHG images ZS1. The SHG image PS1 is an SHG image in which a tissue of which a depth oriented inward from an epithelial tissue of a uterine tissue is 15 μm is imaged.

In the embodiment, the example of the fiber-like structure determination unit 190b that determines the fiber-like structure in the Z stack SHG images ZS1 using the machine learning has been described, but the present invention is not limited thereto. The fiber-like structure may be determined by a user of the uterine cancer determination device 1b. When the fiber-like structure is determined by the user of the uterine cancer determination device 1b, the cancer progress determination unit 19b receives, for example, a manipulation of determining the fiber-like structure in the Z stack SHG image ZS1 via the manipulation input unit 16. The cancer progress determination unit 19b generates the Z stack fiber-like structure image ZF1 based on the received manipulation of determining the fiber-like structure.

Referring back to FIG. 26, the precancer or invasive cancer determination process will be described.

Step S720: the fibrosis amount calculation unit 191b calculates a fibrosis amount of the superficial part of the uterine tissue imaged as the Z stack SHG images ZS1 based on the Z stack fiber-like structure images ZF1 generated by the fiber-like structure determination unit 190b. The fibrosis amount calculation unit 191b supplies the calculated fibrosis amount to the precancer or invasive cancer determination unit 192b.

Here, the fibrosis amount calculation unit 191b calculates a ratio of an area of a part in which the fiber-like structure is imaged to a whole area of the Z stack fiber-like structure image ZFi as the fibrosis amount. The fibrosis amount calculation unit 191b calculates the areas based on the number of pixels. That is, the fibrosis amount calculation unit 191b calculates the ratio of the number of pixels of a part in which the fiber-like structure is imaged to the number of whole pixels of the Z stack fiber-like structure image ZFi as the fibrosis amount. Hereinafter, this ratio is referred to as a detection pixel ratio.

Figure 28:
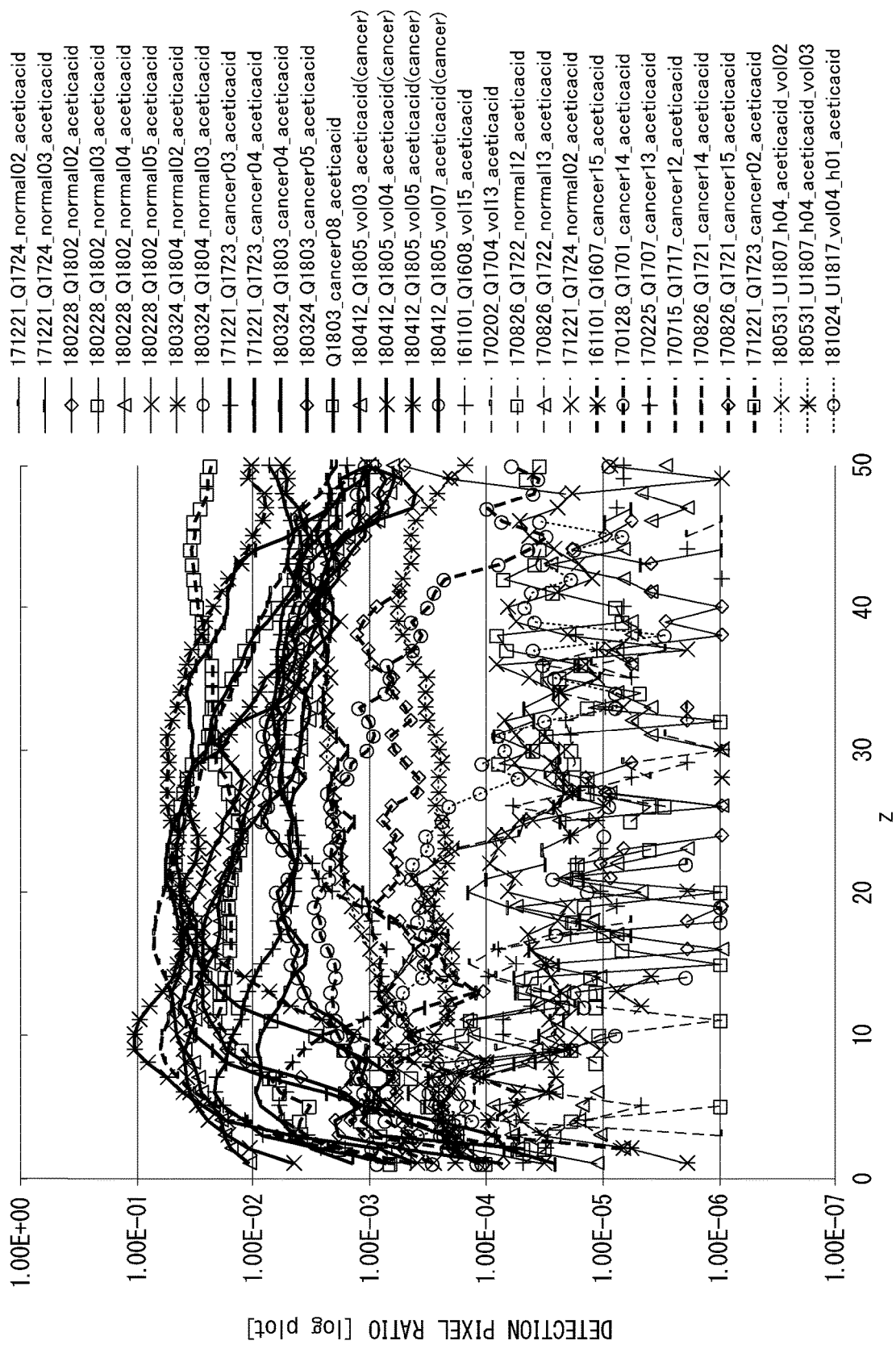
FIG. 28 is a diagram showing examples of detection pixel ratios according to the third embodiment.

Here, the detection pixel ratio calculated by the fibrosis amount calculation unit 191b will be described with reference to FIGS. 28 and 29. FIG. 28 is a diagram showing examples of detection pixel ratios according to the embodiment. In FIG. 28, when uterine tissues of the invasive cancer are 16 samples, uterine tissues of the precancer are 5 samples, and normal uterine tissues are 15 samples, each detection pixel ratio is shown in the Z axis of the Z stack images.

As described above, the precancer or invasive cancer determination process is performed after the uterine tissue is determined to be a cancer tissue. In FIG. 28, however, the detection pixel ratios calculated using the Z stack SHG images of the normal tissue are shown for comparison in addition to the cancer tissues (the invasive cancer and the precancer).

As a value of a coordinate of the Z axis increases, a depth from an epithelial tissue of the superficial part of the imaged uterine tissue is deeper. The value of the Z coordinate of the epithelial tissue is 0. A value of the Z coordinate of a boundary between a deep part and a superficial part of the uterine tissue is 50.

Figure 29:
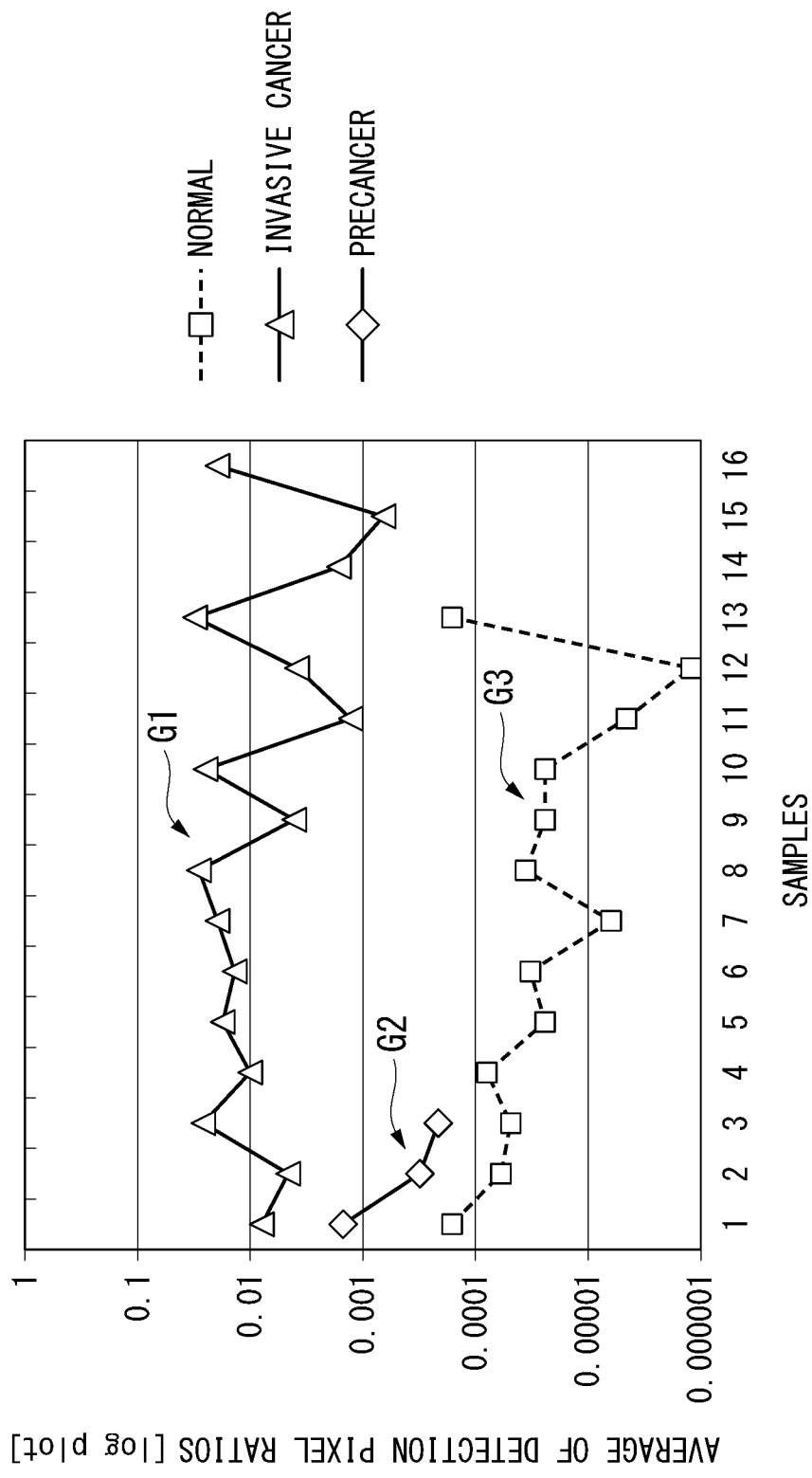
FIG. 29 is a diagram showing an example of the average of the detection pixel ratios in a superficial part of a uterine tissue according to the third embodiment.

FIG. 29 is a diagram showing an example of an average of the detection pixel ratios in a superficial part of a uterine tissue according to the embodiment. The average in the superficial part of the uterine tissue is an average at the values of the Z stack images on the Z axis. Three graphs illustrated in FIG. 29 indicate averages of the detection pixel ratios in the superficial part of the uterine tissue with numbers indicating samples. A graph G1 indicates the average of the detection pixel ratios in the uterine tissue of the invasive cancer. A graph G2 indicates the average of the detection pixel ratios in the uterine tissue of the precancer. A graph G3 indicates the average of the detection pixel ratios in the normal uterine tissue.

From the graphs G1, G2, and G3, it can be understood that the detection pixel ratios are larger in the cancer tissue than in the normal tissue. From the graphs G1 and G2, it can be understood that the detection pixel ratios are larger in the invasive cancer than in the precancer. As the cancer progress develops, the detection pixel ratios increase. Here, the detection pixel ratio corresponds to a fibrosis amount of the superficial part of the uterine tissue. Accordingly, as the cancer progress develops, the fibrosis amount of the superficial part of the uterine tissue increases.

Referring back to FIG. 26, description of the precancer or invasive cancer determination process will continue.

Step S730: the precancer or invasive cancer determination unit 192b determines whether the uterine tissue determined to be highly likely to be a cancer tissue is the precancer or the invasive cancer based on the detection pixel ratio calculated by the fibrosis amount calculation unit 191b. The precancer or invasive cancer determination unit 192b supplies the determined result as the determination result Ab to the output unit 15.

Here, when the average of the detection pixel ratios is greater than a predetermined determination threshold in a sample, the precancer or invasive cancer determination unit 192b determines that the uterine tissue is the invasive cancer. Conversely, when the average of the detection pixel ratios is less than the predetermined determination threshold in the sample, the precancer or invasive cancer determination unit 192b determines that the uterine tissue is the precancer.

Then, the cancer progress determination unit 19b ends the precancer or invasive cancer determination process.

The average of the detection pixel ratios in the superficial part of the uterine tissue according to the embodiment has been used in description. However, the present invention is not limited thereto. For example, a maximum value of the detection pixel ratios of the superficial part may be determined instead of the average.

Figures 30, 31:
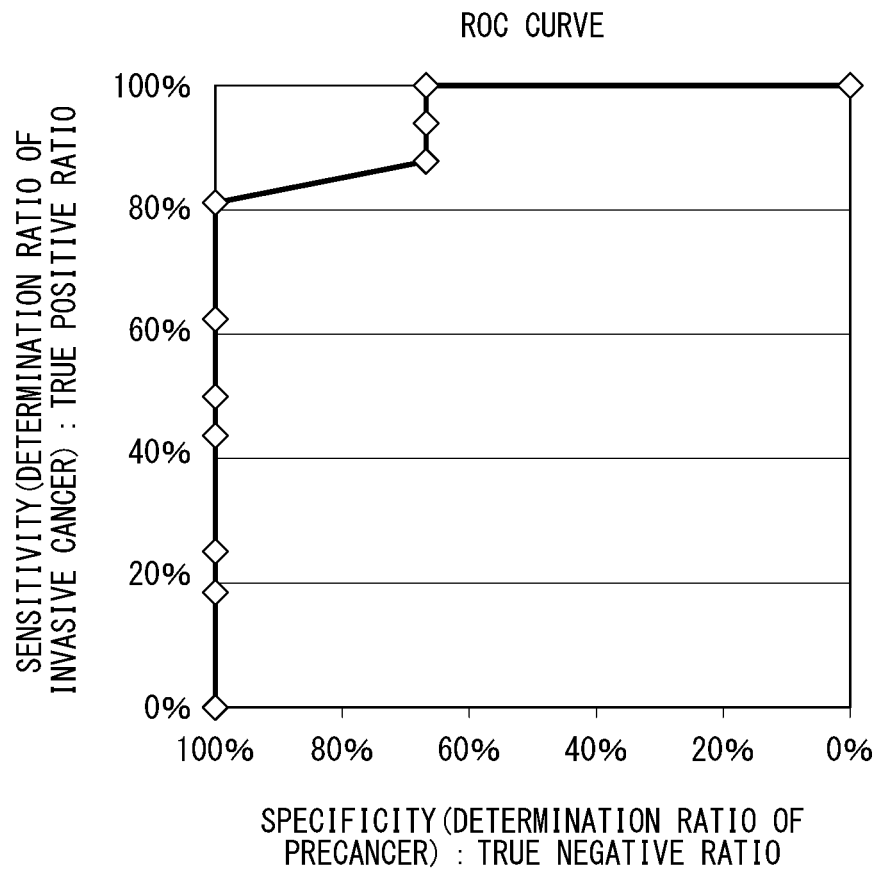
FIG. 30 is a diagram showing an example of an ROC curve indicating a determination ratio of a cancer progress determination unit according to the third embodiment.
FIG. 31 is a diagram showing an example of a relation between a determination ratio and a determination threshold of the cancer progress determination unit according to the third embodiment.

Here, the determination ratio of the cancer progress determination unit 19b will be described using a receiver operating characteristic (ROC) curve with reference to FIGS. 30 and 31. FIG. 30 is a diagram showing an example of an ROC curve indicating a determination ratio of the cancer progress determination unit 19b according to the embodiment. FIG. 31 is a diagram showing an example of a relation between a determination ratio and a determination threshold of the cancer progress determination unit 19b according to the embodiment.

The ROC curve of FIG. 30 indicates a determination ratio of an invasive cancer as sensitivity to a determination ratio of a precancer as specificity. In FIG. 30, an invasive cancer is caused to correspond to positiveness and a precancer is caused to correspond to negativeness for evaluation. That is, the determination ratio of the precancer corresponds to a true negative ratio and a determination ratio of the invasive cancer correspond to a true positive ratio. In the ROC curve of FIG. 30, the value of the area under the ROC curve (AUC) is 0.88.

As illustrated in FIG. 31, when the determination threshold used by the precancer or invasive cancer determination unit 192b is changed and the determination threshold is 0.0025, the determination ratios at which sensitivity is 81.3 percent and specificity is 80.0 percent could be obtained. The value of the AUC of the ROC curve of FIG. 30 is the value when the determination threshold is 0.0025.

In the embodiment, the example of the cancer progress determination unit 19b that determines which is applied between the precancer or the invasive cancer as the cancer progress has been described, but the present invention is not limited thereto. The cancer progress determination unit 19b may determine which is applied among the following as the cancer progress:

(A) a precancer;
(B) an invasive cancer;
(C) mild dysplasia (CIN1), intermediate dysplasia (CIN2), or severe dysplasia carcinoma in situ (CIN3);
(D) a microinvasive squamous cell carcinoma or a squamous cell carcinoma; and
(E) a cancer for which treatment is necessary or a cancer for which treatment is not necessary.

Conclusion

As described above, the uterine cancer determination device 1b according to the embodiment includes the second harmonic image acquisition unit (in this example, the SHG image acquisition unit 18b) and the cancer progress determination unit 19b.

The second harmonic image acquisition unit (in this example, the SHG image acquisition unit 18b) acquires the second harmonic images (in this example, the Z stack SHG images ZS1) of the uterine tissue of the examinee obtained by the multiphoton microscope 2b.

When the cancer tissue determination unit 14 determines that the likelihood that the uterine tissue of the examinee is a cancer tissue is high, the cancer progress determination unit 19b determines the cancer progress (in this example, classified in accordance with the precancer and the invasive cancer) based on the state of the fiber-like structure in the second harmonic image (in this example, the Z stack SHG image ZS1).

In this configuration, the uterine cancer determination device 1b according to the embodiment can determine the cancer progress based on the state of the fiber-like structure in the second harmonic image of the superficial part of the uterine tissue of the examinee. Therefore, it is possible to determine the cancer progress of the uterine tissue without dyeing the uterine tissue. That is, the uterine cancer determination device 1b can determine the cancer progress of the uterine tissue without investigating a deep part of the uterine tissue and without dyeing the uterine tissue.

In the uterine cancer determination device 1b according to the embodiment, the cancer progress determination unit 19b may determine which is applied among the following as the cancer progress:

(A) a precancer;
(B) an invasive cancer;
(C) mild dysplasia (CIN1), intermediate dysplasia (CIN2), or severe dysplasia carcinoma in situ (CIN3);
(D) a microinvasive squamous cell carcinoma or a squamous cell carcinoma; and
(E) a cancer for which treatment is necessary or a cancer for which treatment is not necessary.

In this configuration, the uterine cancer determination device 1b according to the embodiment can determine which is applied among the above-described items (A) to (E) as the cancer progress based on the state of the fiber-like structure in the second harmonic image of the superficial part of the uterine tissue of the examinee. Therefore, it is possible to determine which is applied among the above-described items (A) to (E) as the cancer progress without dyeing the uterine tissue.

Fourth Embodiment

Hereinafter, a fourth embodiment will be described in detail with reference to the drawings.

As uterine cancers, there are a cervical cancer which is a cancer of a cervical tissue and a corpus uteri cancer which is a cancer of a corpus uteri tissue. For the cervical cancer, cervical carcinoma in situ in which a cancer occurs in an epithelial tissue develops to an invasive cancer in accordance with the degree of cancer progress. It is known that fibrosis occurs in a surrounding tissue when a cancer develops.

On the other hand, a technology for determining a cancer tissue by analyzing an image obtained by imaging a biological tissue is known. When the cancer tissue is determined through image analysis, an image obtained by imaging a dyed biological tissue is used.

For example, a cancer examination device including a determination unit that images a biological cell group to which a dyeing agent for selectively dyeing a cancer-related gene product of a biological cell in chromatic color is applied and determines the malignancy level of canceration of the biological cell group based on a dyed state of the biological cell group in an obtained image has been known (see Patent Document 1).

In the related art, it was difficult to analyze the state of an undyed tissue at the cellular level.

Figure 32:
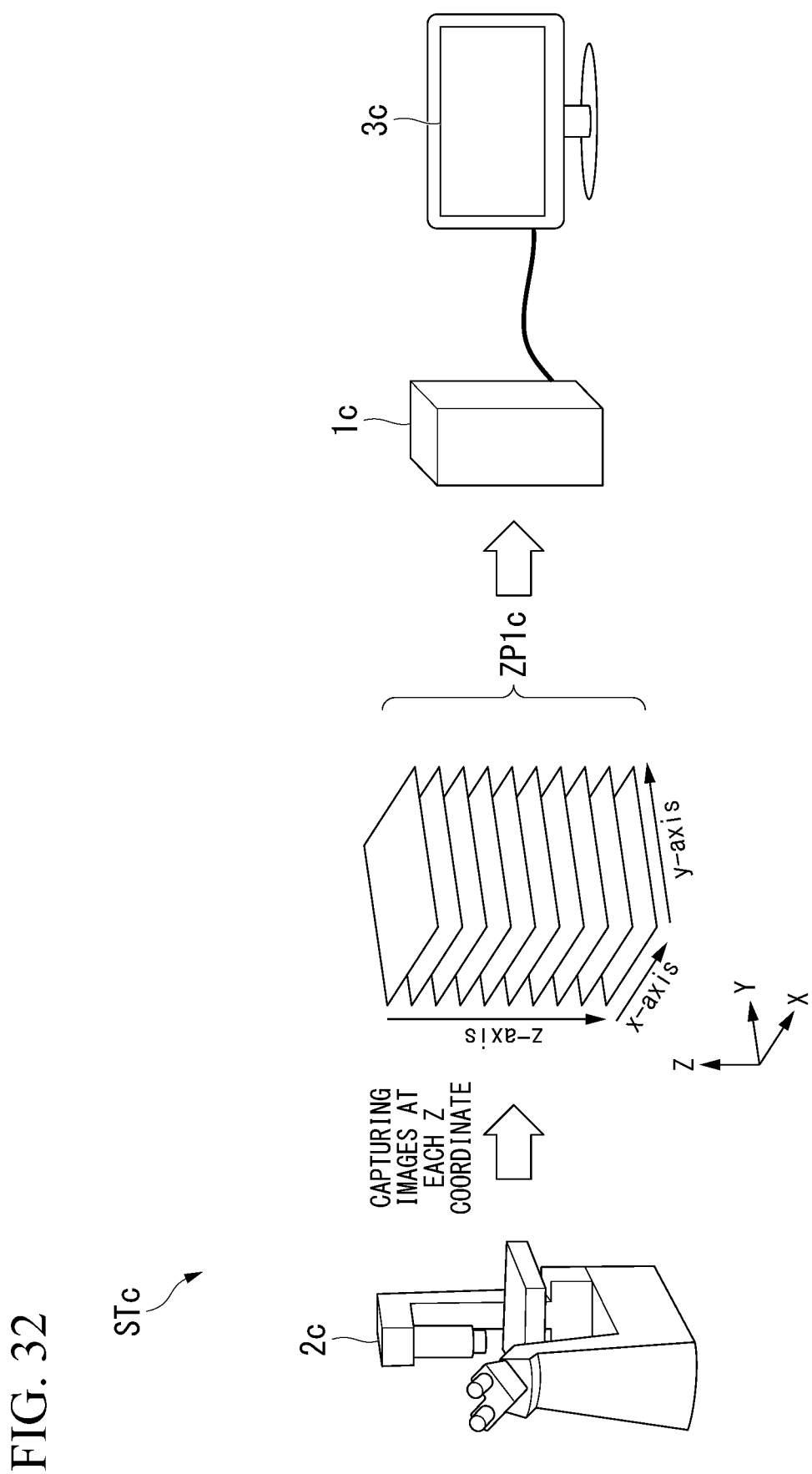
FIG. 32 is a diagram showing an example of a uterine cancer progress determination system according to a fourth embodiment.

FIG. 32 is a diagram showing an example of a uterine cancer progress determination system STc according to the embodiment. The uterine cancer progress determination system STc includes a cancer progress determination device 1c, a multiphoton microscope 2c, and a display device 3c. In the uterine cancer progress determination system STc, the cancer progress determination device 1c analyzes Z stack captured images ZP1c of a uterine tissue of an examinee captured by the multiphoton microscope 2c and determines progress of a uterine cancer of the examinee.

In the embodiment, the uterine tissue is, for example, a cervix tissue and a corpus uteri tissue.

The Z stack captured images ZP1c are Z stack images. The Z stack images refer to a set of a plurality of images captured by changing a distance from a uterine tissue in the Z axis direction. The Z stack captured images ZP1c are formed from a plurality of images obtained by capturing images of the uterine tissue at each Z coordinate. Here, capturing images of the uterine tissue at each Z coordinate is capturing images of the uterine tissue by variously changing a distance between an objective lens and the uterine tissue. The Z stack captured images ZP1c are a plurality of images captured by the multiphoton microscope 2c by changing the distance between the uterine tissue and a lens.

In the embodiment, the Z axis is selected in a direction oriented inward from an epithelial tissue of the uterine tissue. That is, a value of the Z axis is smaller on an imaging surface close to a uterine epithelial tissue. A value of the Z axis increases as the imaging surface is deeper inside the uterine tissue. The origin of the Z axis is selected at a shallow position close to the uterine epithelial tissue.

In this way, the Z stack captured images ZP1c are a plurality of cross-sectional images perpendicular in a depth direction of the uterine epithelial tissue of the examinee and are simply referred to as cross-sectional images. The depth direction is a direction oriented from a surface layer to a basal layer. The plurality of cross-sectional images may not be completely perpendicular in the depth direction of the uterine epithelial tissue of the examinee and may be inclined about ±5 degrees.

The multiphoton microscope 2c observes and images the uterine tissue of the examinee in an undyed state. The multiphoton microscope 2c images the uterine tissue using a nonlinear optical phenomena. As the nonlinear optical phenomena used in the imaging of the multiphoton microscope 2c, there is second harmonic generation (SHG).

SHG refers to a phenomenon in which light with a double frequency of excitation light is generated. SHG occurs by interaction with nonlinear optical crystal of a collagen fiber or the like.

When a tumor develops, fibrosis occurs in a surrounding tissue. Fibers occurring due to the fibrosis are formed from molecules containing various kinds of collagen. In some fibrillar collagen, SHG occurs. According to the embodiment, the multiphoton microscope 2c images a uterine tissue using SHG to generate second harmonic images. The second harmonic image is an image of a cross section of a uterine tissue generated based on light generated in second harmonic generation caused by interaction between the uterine tissue and excitation light emitted from an irradiation unit of the multiphoton microscope 2c. Hereinafter, the second harmonic image is referred to as an SHG image.

In the embodiment, the Z stack captured images ZP1c are Z stack captured images of the SHG images. Therefore, hereinafter, the Z stack captured images ZP1c are referred to as Z stack SHG images ZS1c. That is, the Z stack SHG images ZS1c are a plurality of SHG images obtained by imaging the uterine tissue using SHG by changing the distance from the uterine tissue in the Z axis direction. That is, the Z stack SHG images ZS1c are a plurality of cross-sectional images captured at each of a plurality of depths of a uterine epithelial tissue. Here, the cross-sectional images are second harmonic generation images obtained by the multiphoton microscope 2c.

A plurality of images included in the Z stack SHG images ZS1c are expressed as SHG images PSic (where i=1, 2, ..., N: N is the number of images included in the Z stack SHG images ZS1c) or the like.

The multiphoton microscope 2c captures the SHG image at each depth of the uterine tissue.

Figure 33:
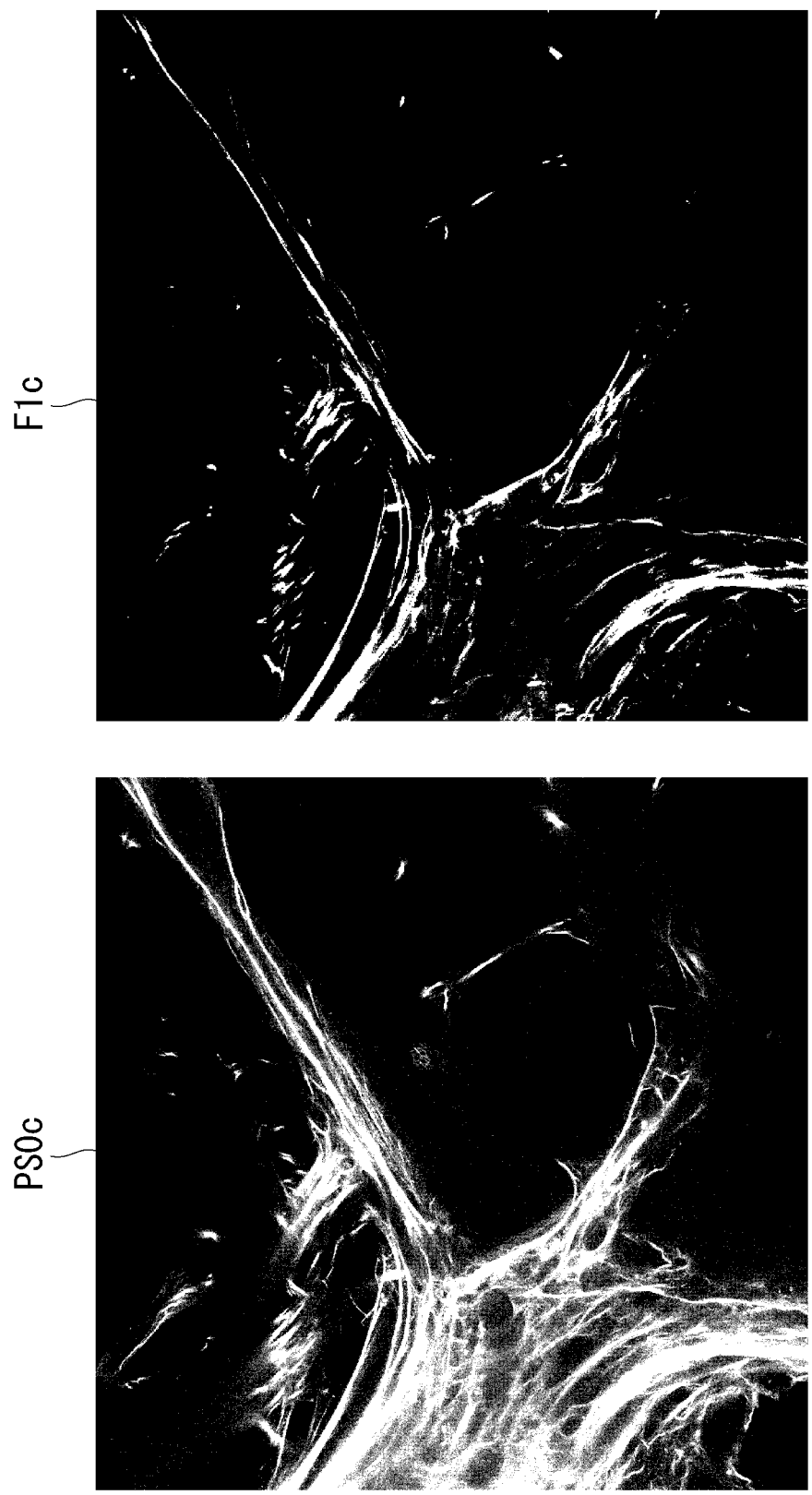
FIG. 33 is a diagram showing an example of a second harmonic generation image according to the fourth embodiment.

Here, the SHG images captured by the multiphoton microscope 2c will be described with reference to FIG. 33. FIG. 33 is a diagram showing an example of the SHG image PS0c according to the embodiment. In FIG. 33, a fiber-like structure image F1c is illustrated along with the SHG image PS0c for comparison. In the SHG image PS0c captured by the multiphoton microscope 2c, it can be understood that a fiber-like structure is imaged to the same degree as that of a fiber-like structure imaged in the fiber-like structure image F1c.

As a tumor develops, fibrosis spreads from a deep part to a superficial part of a uterine tissue.

Here, an aspect in which the fibrosis spreads from a deep part to a superficial part of a uterine tissue will be described with reference to FIG. 34. FIG. 34 is a diagram showing an example of a cross section of a uterine tissue at each stage of tumor progress according to the embodiment.

Figure 34A:
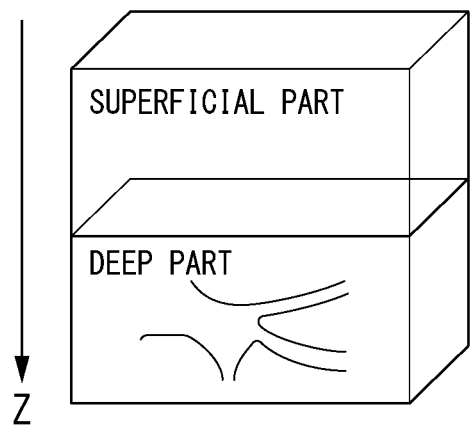
FIG. 34A is a diagram showing an example of a cross section of a uterine tissue at each stage of tumor progress according to the fourth embodiment.
Figure 34B:
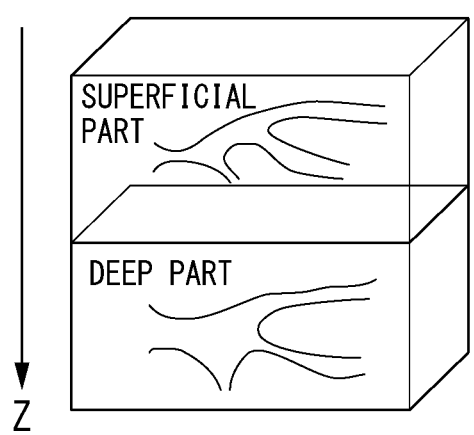
FIG. 34B is a diagram showing an example of a cross section of a uterine tissue at each stage of tumor progress according to the fourth embodiment.

In FIG. 34A, there is a fiber-like structure in the deep part of the uterine tissue. In FIG. 34B, fibrosis occurs in the superficial part on a cross section of the uterine tissue when the tumor develops.

In the embodiment, the Z axis is also set in a direction oriented inward from an epithelial tissue of the uterine tissue. As the tumor develops, the fibrosis spread from a part in which a value of the Z coordinate is large to a part in which a value of the Z coordinate is small in the uterine tissue.

In the superficial part of the uterine tissue, it is not known in advance at which depth the fibrosis occurs because of a difference in accordance with the stage of tumor progress. In the cancer progress determination device 1c, the fiber-like structure can be extracted even when the fibrosis occurs at any depth of the superficial part of the tissue by using the Z stack SHG images ZS1c.

Configuration of Uterine Cancer Determination Device

Figure 35:
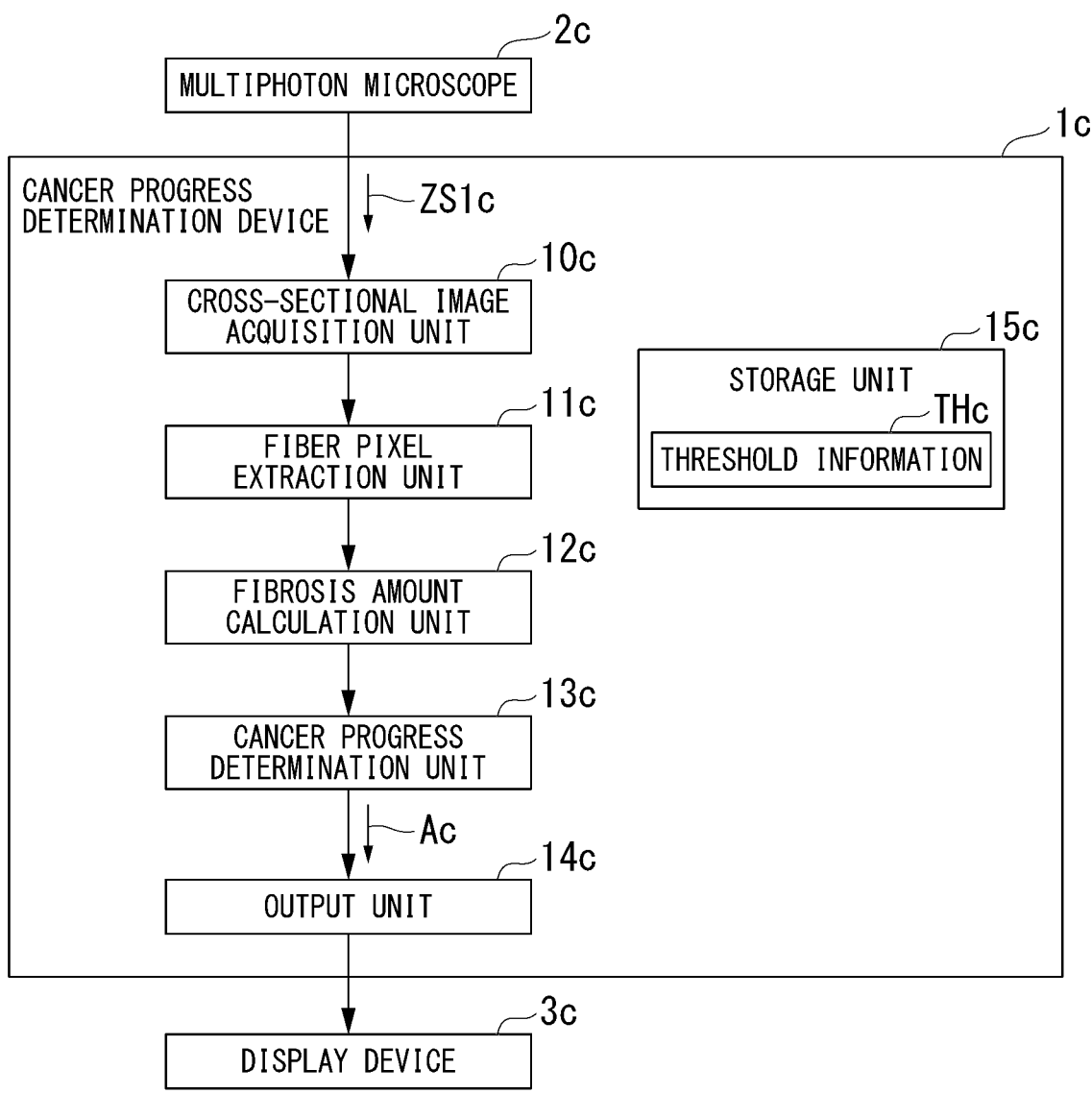
FIG. 35 is a diagram showing an example of a cancer progress determination device according to the fourth embodiment.

Next, a configuration of the cancer progress determination device 1c will be described with reference to FIG. 35. FIG. 35 is a diagram showing an example of the cancer progress determination device 1c according to the embodiment. The cancer progress determination device 1c is, for example, a computer.

The cancer progress determination device 1c includes a cross-sectional image acquisition unit 10c, a fiber pixel extraction unit 11c, a fibrosis amount calculation unit 12c, a cancer progress determination unit 13c, an output unit 14c, and a storage unit 15c. The cross-sectional image acquisition unit 10c, the fiber pixel extraction unit 11c, the fibrosis amount calculation unit 12c, the cancer progress determination unit 13c, and the output unit 14c are modules implemented by causing a central processing unit (CPU) to read a program from a read-only memory (ROM) and performing a process.

The cross-sectional image acquisition unit 10c acquires the Z stack SHG images ZS1c captured by the multiphoton microscope 2.

The fiber pixel extraction unit 11c extracts fiber pixels which are pixels in which the fiber-like structure is imaged among the pixels in SHG image PSic included in the Z stack SHG image ZS1c. Here, in the embodiment, the fiber pixel extraction unit 11c extracts the fiber pixels based on, for example, machine learning. The fiber pixel extraction unit 11c generates Z stack fiber-like structure images ZF1c from the Z stack SHG images ZS1c based on the extracted fiber pixels. The Z stack fiber-like structure image ZF1c is a Z stack image in which the fiber-like structure is shown.

Each of a plurality of images included in the Z stack fiber-like structure images ZF1c are referred to as fiber-like structure images PFic (where i=1, 2, ..., N: N is the number of images included in the Z stack fiber-like structure images ZF1c) or the like.

The fibrosis amount calculation unit 12c calculates an amount of the fiber-like structure imaged in the Z stack fiber-like structure image ZF1c generated by the fiber pixel extraction unit 11c. Hereinafter, the amount of the fiber-like structure imaged in the Z stack SHG image ZS1c is referred to as a fibrosis amount in some cases.

The cancer progress determination unit 13c determines the progress of a uterine cancer of the examinee based on the fibrosis amount calculated by the fibrosis amount calculation unit 12c. In the embodiment, the progress of the uterine cancer is classified in an ascending order of the degree of progress in accordance with a non-cancer, a precancer, or an invasive cancer, for example.

The output unit 14c outputs a determination result Ac of the cancer progress determination unit 13c to the display device 3c. The determination result Ac indicates progress of the uterine cancer of the examinee.

The display device 3c displays the determination result Ac determined by the cancer progress determination device 1c. The display device 3c is, for example, a display.

The storage unit 15c stores various kinds of information. The various kinds of information include, for example, a threshold information THc calculated from a case image of the examinee. The threshold information THc is information indicating a threshold for a fibrosis amount and includes a first threshold TH1c and a second threshold TH2c. The first threshold TH1c indicates a boundary between a fibrosis amount of the precancer and a fibrosis amount of the non-cancer. The second threshold TH2c indicates a boundary between a fibrosis amount of the precancer and a fibrosis amount of the invasive cancer. The second threshold TH2c is greater than the first threshold TH1c.

Cancer Progress Determination Process

Figure 36:
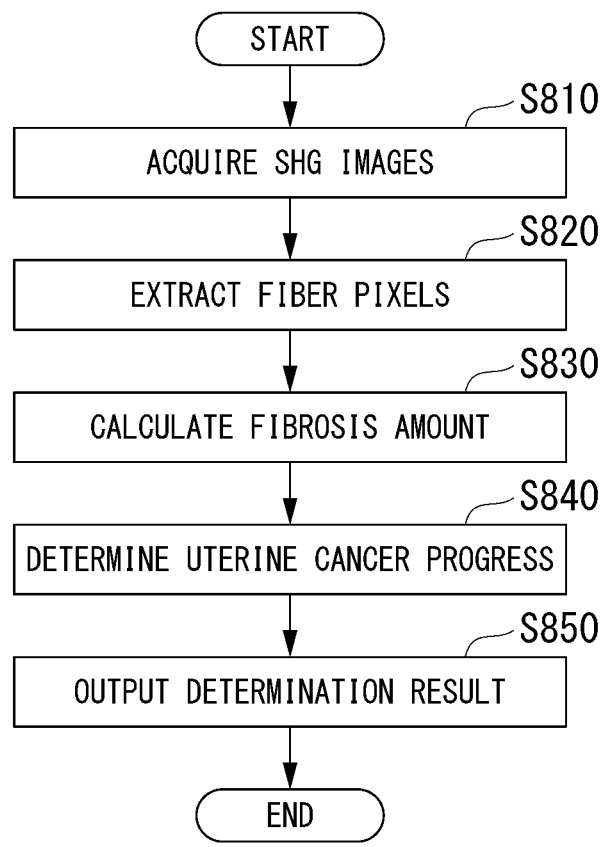
FIG. 36 is a diagram showing an example of a cancer progress determination process according to the fourth embodiment.

Next, a cancer progress determination process which is a process in which the cancer progress determination device 1c determines progress of the uterine cancer of the examinee will be described. FIG. 36 is a diagram showing an example of a cancer progress determination process according to the embodiment.

Step S810: the cross-sectional image acquisition unit 10c acquires the Z stack captured images ZP1c captured by the multiphoton microscope 2c. That is, the cross-sectional image acquisition unit 10c acquires cross-sectional images of the uterine epithelial tissue of the examinee.

Step S820: the fiber pixel extraction unit 11c extracts the fiber pixels which are the pixels in which the fiber-like structure is imaged among the pixels in each of the SHG image PSic included in the Z stack SHG image ZS1c. The fiber pixel extraction unit 11c generates the Z stack fiber-like structure images ZF1c from the Z stack SHG images ZS1c based on an extracted result. The fiber pixel extraction unit 11c supplies the generated Z stack fiber-like structure images ZF1c to the fibrosis amount calculation unit 12c.

Here, the fiber pixel extraction unit 11c determines whether the fiber-like structure is imaged in each pixel based on a predetermined reference and extracts the fiber pixels based on a determination result. The fiber pixel extraction unit 11c performs the determination based on, for example, machine learning. That is, the fiber pixel extraction unit 11c uses a reference generated through the machine learning as the predetermined reference for determining the fiber-like structure.

The fiber pixel extraction unit 11c uses, for example, a conditional generative adversarial network (GAN) as the machine learning. The conditional GAN is configured by two networks, a network called a generation unit and a network called an identification unit. The generation unit learns generation of a fake image which is not found out by the identification unit. On the other hand, the identification unit learns an identifier with which the fake image generated by the generation unit can be found out.

In the embodiment, the reference generated through the machine learning is a reference by which the identification unit of the conditional GAN determines that the fiber-like structure is imaged in the pixels.

The machine learning used by the fiber pixel extraction unit 11c may be machine learning other than the conditional GAN.

Here, the fiber-like structure image PF1c included in the Z stack fiber-like structure image ZF1c generated by the fiber pixel extraction unit 11c will be described with reference to FIG. 37. FIG. 37 is a diagram showing an example of a fiber-like structure image PF1c according to the embodiment.

The fiber-like structure image PF1c is an image in which the fiber-like structure is determined based on the SHG image PS1c included in the Z stack SHG image ZS1c. The SHG image PS1c is an SHG image in which a tissue of which a depth oriented inward from an epithelial tissue of a uterine tissue is 15 μm is imaged.

As described above, in the embodiment, the fiber pixel extraction unit 11c extracts the fiber pixels based on the Z stack captured image ZP1c acquired by the cross-sectional image acquisition unit 10c and the reference generated through the machine learning.

In the embodiment, the example of the fiber pixel extraction unit 11c that determines the fiber-like structure in the Z stack SHG image ZS1c using the machine learning has been described, but the present invention is not limited thereto. The fiber pixel extraction unit 11c may determine whether the fiber-like structure is imaged in the pixels, for example, by using a reference indicating inclusion in an area in which the pixels continue and which has a shape equal to or less than a predetermined width and equal to or greater than a predetermined length as the predetermined reference. The Z stack SHG images ZS1c may be configured not to include images classified to a non-cancer.

That is, the fiber pixel extraction unit 11c extracts the fiber pixels which are pixels in which the fiber-like structure is imaged among the pixels of the Z stack captured image ZP1c based on the predetermined reference and the Z stack captured image ZP1c acquired by the cross-sectional image acquisition unit 10c.

In the embodiment, the example of the fiber pixel extraction unit 11c that determines the fiber pixels has been described, but the present invention is not limited thereto. The fiber pixels may be determined by a user of the cancer progress determination device 1c. When the fiber pixels are determined by the user of the cancer progress determination device 1c, the cancer progress determination device 1c includes a manipulation input unit. The fiber pixel extraction unit 11c receives, for example, a manipulation of determining the fiber-like structure in the Z stack SHG image ZS1c via the manipulation input unit. The fiber pixel extraction unit 11c generates the Z stack fiber-like structure image ZF1c based on the received manipulation of determining the fiber-like structure.

Referring back to FIG. 36, the description of the cancer progress determination process will continue.

Step S830: the fibrosis amount calculation unit 12c calculates a fibrosis amount of a superficial part of the uterine tissue imaged as the Z stack SHG image ZS1c based on the Z stack fiber-like structure image ZF1c generated by the fiber pixel extraction unit 11c. Here, the Z stack fiber-like structure image ZF1c generated by the fiber pixel extraction unit 11c are Z stack image in which the fiber-like structure is shown in the Z stack SHG image ZS1c acquired by the cross-sectional image acquisition unit 10c. That is, the fibrosis amount calculation unit 12c calculates an amount of the fiber-like structure imaged in the Z stack SHG image ZS1c acquired by the cross-sectional image acquisition unit 10c. The fibrosis amount calculation unit 12c supplies the calculated fibrosis amount to the cancer progress determination unit 13c.

Here, the fibrosis amount calculation unit 12c calculates an amount of the fiber-like structure (a fibrosis amount) imaged in the Z stack SHG image ZS1c based on the fiber pixels extracted by the fiber pixel extraction unit 11c. The fibrosis amount calculation unit 12c calculates a ratio of an area of a part in which the fiber-like structure is imaged to the whole area of the Z stack fiber-like structure image ZFic as the fibrosis amount. The fibrosis amount calculation unit 12c calculates these areas based on the number of pixels. That is, the fibrosis amount calculation unit 12c calculates the ratio of the number of pixels of a part in which the fiber-like structure is imaged to the number of whole pixels of the Z stack fiber-like structure image ZFic as the fibrosis amount. Hereinafter, this ratio is referred to as a detection pixel ratio.

In the embodiment, the example of the fibrosis amount calculation unit 12c that calculates the ratio of the area of the part in which the fiber-like structure is imaged to the whole area of the Z stack fiber-like structure image ZFic as the fibrosis amount has been described, but the present invention is not limited thereto.

The fibrosis amount calculation unit 12c may calculate the area of the fiber-like structure imaged in the Z stack fiber-like structure image ZFic as the fibrosis amount or may calculate a length of the fiber-like structure or the number of the fiber-like structures as the fibrosis amount. The fibrosis amount calculation unit 12c may apply predetermined pre-processing to the Z stack fiber-like structure image ZFic to calculate the fibrosis amount. The predetermined preprocessing is, for example, a binarization process. Thus, it is possible to calculate the amount of the fiber-like structure imaged in the Z stack SHG image ZS1c more reliably. The preprocessing is not limited to the binarization process and a smoothing process or morphology processing may be applied.

The fibrosis amount calculation unit 12c may calculate a ratio of the number of pixels of the fiber-like structure to the number of whole pixels of the cross-sectional image or the total amount or the average amount of the fiber-like structures imaged in the plurality of Z stack fiber-like structure images ZFic included in the Z stack SHG images ZS1c as the fibrosis amount. When the ratio of the number of pixels of the fiber-like structure to the number of whole pixels of the cross-sectional image or the total amount or the average amount of the fiber-like structures imaged in the plurality of Z stack fiber-like structure images ZFic included in the Z stack SHG images ZS1c is calculated and there is a variation in the fibrosis amount among the SHG images ZSic included in the Z stack SHG images ZS1c, it is possible to inhibit deterioration in determination accuracy of the progress of the uterine cancer.

Figure 38:
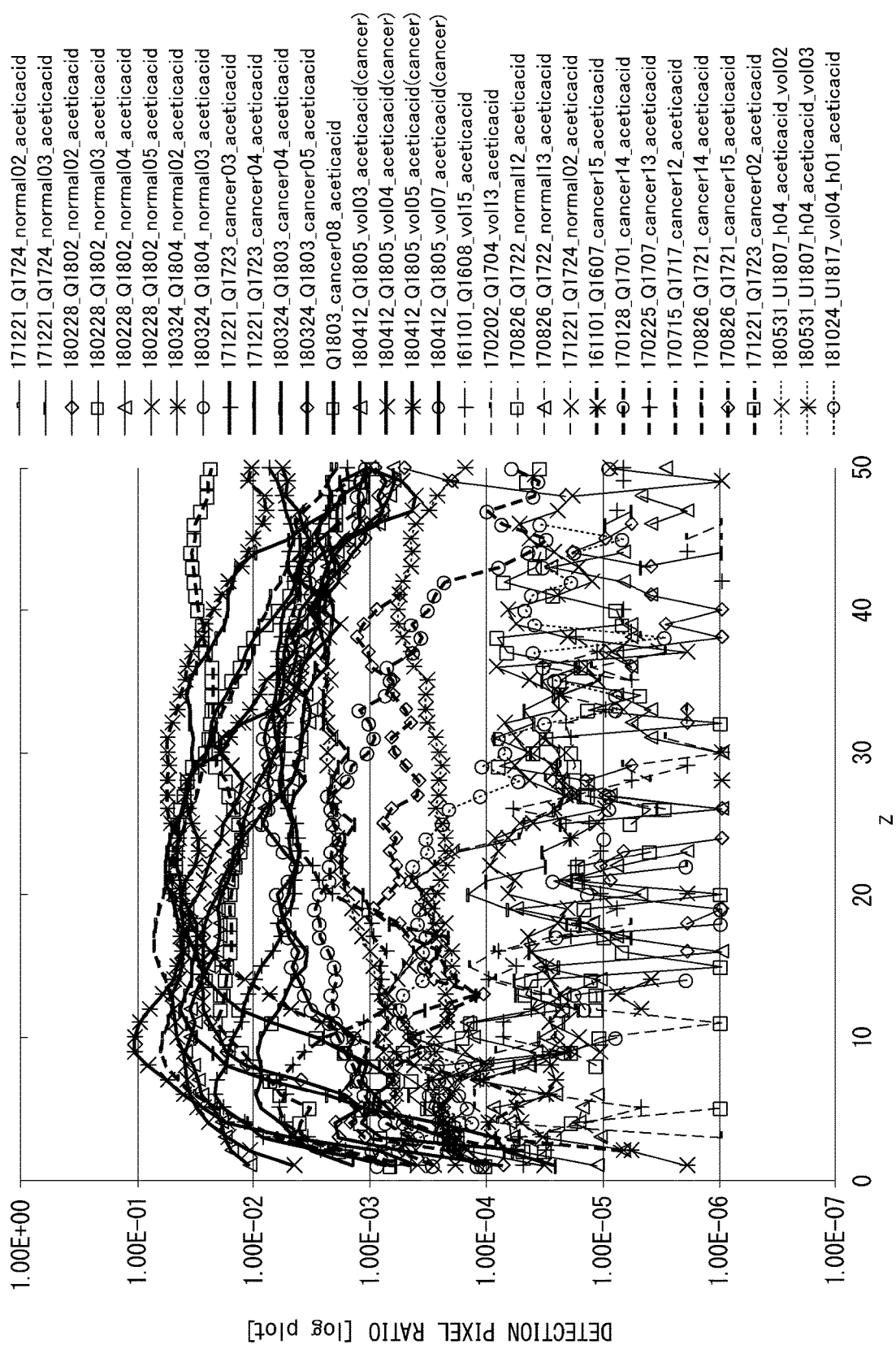
FIG. 38 is a diagram showing an example of a detection pixel ratio according to the fourth embodiment.

Here, the detection pixel ratio calculated by the fibrosis amount calculation unit 12c will be described with reference to FIGS. 38 and 39. FIG. 38 is a diagram showing an example of a detection pixel ratio according to the embodiment. In FIG. 38, when uterine tissues of the invasive cancer are 16 samples, uterine tissues of the precancer are 3 samples, and normal uterine tissues are 13 samples, each detection pixel ratio is shown in the Z axis of the Z stack images.

As the value of a coordinate of the Z axis increases, the depth from an epithelial tissue of the superficial part of the imaged uterine tissue is deeper. The value of the Z coordinate of the epithelial tissue is 0. The value of the Z coordinate of a boundary between a deep part and a superficial part of the uterine tissue is 50.

Figure 39:
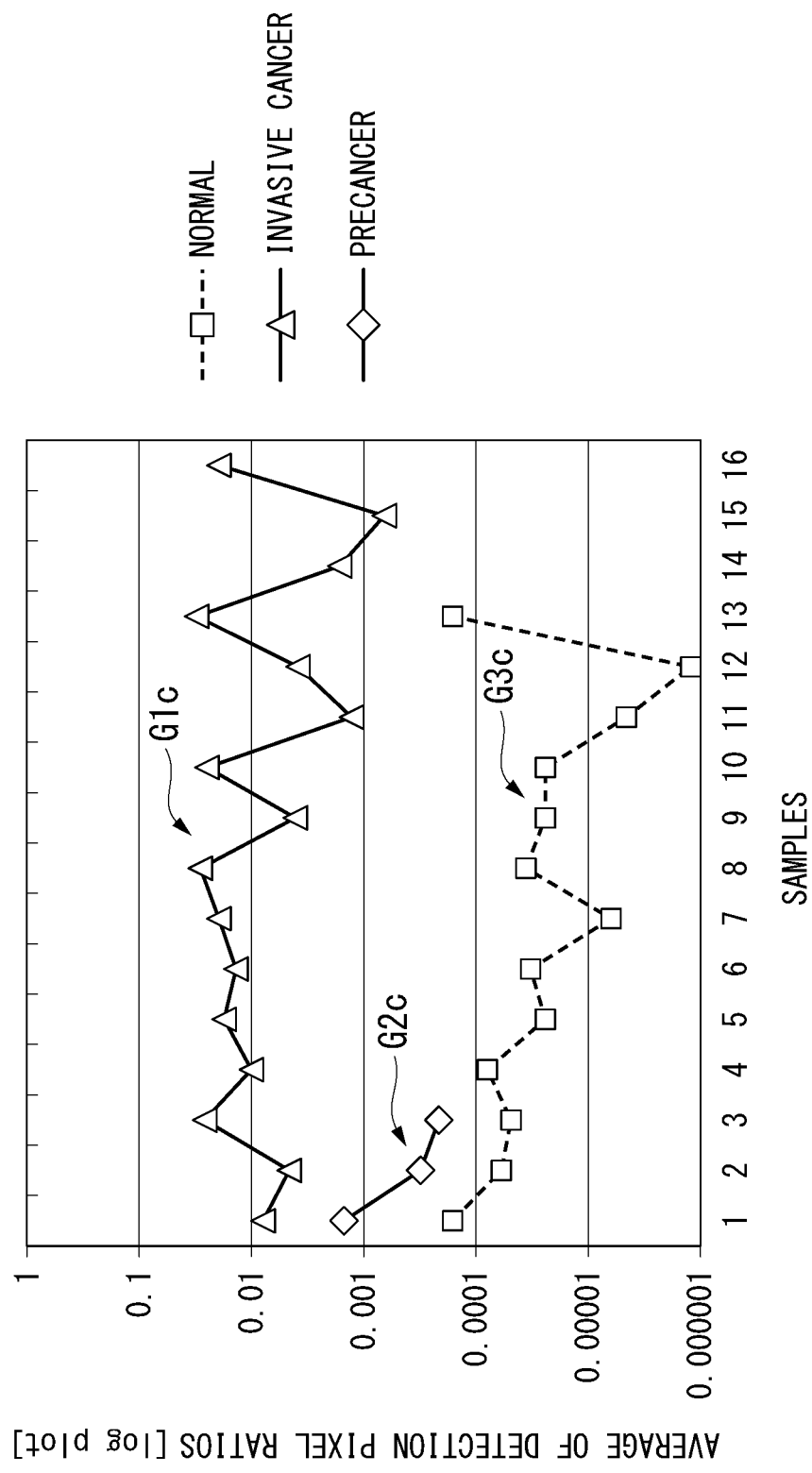
FIG. 39 is a diagram showing an example of an average of the detection pixel ratios in a superficial part of a uterine tissue according to the fourth embodiment.

FIG. 39 is a diagram showing an example of an average in a superficial part of a uterine tissue at the detection pixel ratio according to the embodiment. The average in the superficial part of the uterine tissue is the average for the values of the Z stack images on the Z axis. Three graphs illustrated in FIG. 39 indicate averages of the detection pixel ratios in the superficial part of the uterine tissue with numbers indicating samples. A graph G1c indicates the average of the detection pixel ratios in the uterine tissue of the invasive cancer. A graph G2c indicates the average of the detection pixel ratios in the uterine tissue of the precancer. A graph G3c indicates the average of the detection pixel ratios in the normal uterine tissue.

From the graphs G1c, G2c, and G3c, it can be understood that the detection pixel ratios are larger in the cancer tissue than in the normal tissue. From the graphs G1c and G2c, it can be understood that the detection pixel ratios are larger in the invasive cancer than in the precancer. As the cancer progress develops, the detection pixel ratios increase. Here, the detection pixel ratio corresponds to a fibrosis amount of the superficial part of the uterine tissue. Accordingly, as the cancer progress develops, the fibrosis amount of the superficial part of the uterine tissue increases.

Referring back to FIG. 36, the description of the cancer progress determination process will continue.

Step S840: the cancer progress determination unit 13c determines the progress of the uterine cancer of the examinee based on the detection pixel ratio calculated by the fibrosis amount calculation unit 12c, and the first threshold TH1c and the second threshold TH2c indicated by the threshold information THc. Here, the cancer progress determination unit 13c reads the threshold information THc from the storage unit 15c. The cancer progress determination unit 13c supplies the determined result as the determination result Ac to the output unit 14c.

Here, when the amount of fiber-like structure is equal to or less than the first threshold TH1c, the cancer progress determination unit 13c determines that the uterine epithelial tissue is a non-cancer tissue. Conversely, when the amount of fiber-like structure exceeds the first threshold TH1c, the cancer progress determination unit 13c determines that the examinee is infected or highly likely to be infected with the uterine cancer.

When the amount of fiber-like structure exceeds the first threshold TH1c and is equal to or less than the second threshold TH2c greater than the first threshold TH1c, the cancer progress determination unit 13c determines that the uterine cancer of the examinee is in a precancer state. When the amount of fiber-like structure exceeds the second threshold TH2c, the cancer progress determination unit 13c determines that the uterine cancer of the examinee is an invasive cancer.

Step S850: the output unit 14c outputs the determination result Ac to the display device 3c.

Then, the cancer progress determination device 1c ends the cancer progress determination process.

Figures 40, 41:
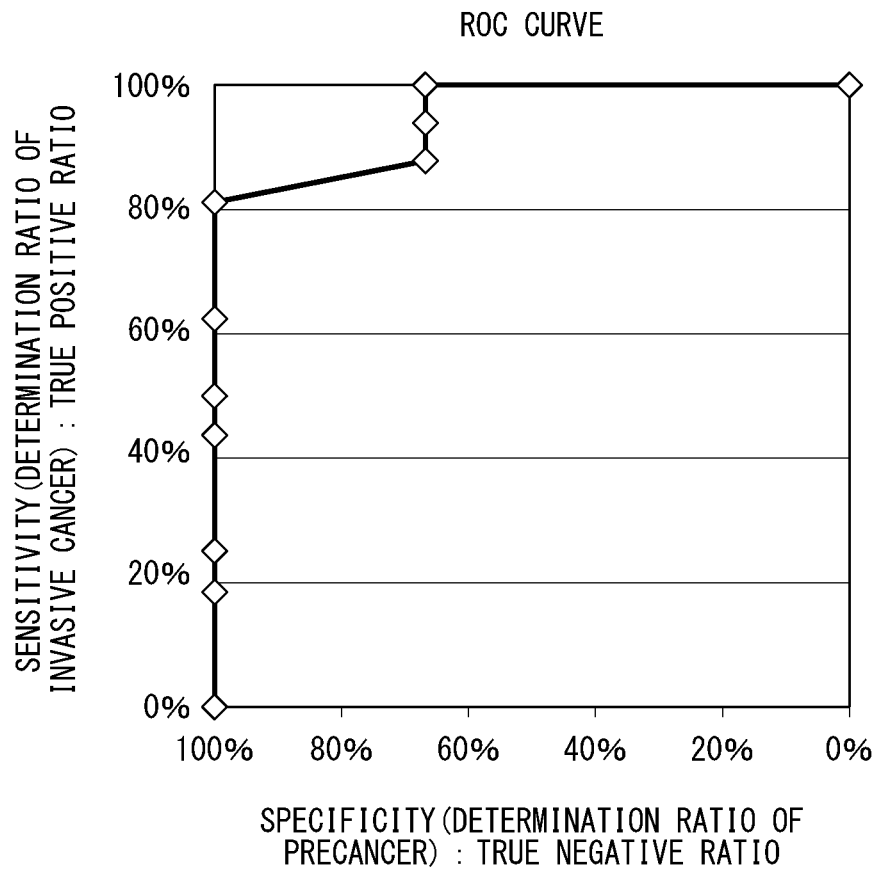
FIG. 40 is a diagram showing an example of an ROC curve indicating a determination ratio of a cancer progress determination unit according to the fourth embodiment.
FIG. 41 is a diagram showing an example of a relation between a determination ratio and a determination threshold of the cancer progress determination unit according to the fourth embodiment.

Here, a determination ratio of the cancer progress determination unit 13c will be described using a receiver operating characteristic (ROC) curve with reference to FIGS. 40 and 41. FIG. 40 is a diagram showing an example of an ROC curve indicating a determination ratio of the cancer progress determination unit 13c according to the embodiment. FIG. 41 is a diagram showing an example of a relation between a determination ratio and a determination threshold of the cancer progress determination unit 13c according to the embodiment.

The ROC curve of FIG. 40 indicates a determination ratio of an invasive cancer as sensitivity to a determination ratio of a precancer as specificity. In FIG. 40, an invasive cancer is caused to correspond to positiveness and a precancer is caused to correspond to negativeness for evaluation. That is, the determination ratio of the precancer corresponds to a true negative ratio and the determination ratio of the invasive cancer corresponds to a true positive ratio. In the ROC curve of FIG. 40, the value of the area under the ROC curve (AUC) is 0.88.

As illustrated in FIG. 41, when the determination threshold used by the cancer progress determination unit 13c is changed and the determination threshold is 0.0025, determination ratios at which sensitivity is 81.3 percent and specificity is 80.0 percent could be obtained. The value of the AUC of the ROC curve of FIG. 40 is the value when the determination threshold is 0.0025.

In the embodiment, the example of the cancer progress determination unit 13c that determines which is applied between the precancer or the invasive cancer as the cancer progress has been described, but the present invention is not limited thereto. The cancer progress determination unit 13c may determine which is applied among the following as the cancer progress:

(A) a precancer;
(B) an invasive cancer;
(C) mild dysplasia (CIN1), intermediate dysplasia (CIN2), or severe dysplasia carcinoma in situ (CIN3);
(D) a cancer for which treatment is necessary or a cancer for which treatment is not necessary. and
(E) a cancer for which treatment is necessary or a cancer for which treatment is not necessary.

As described above, the cancer progress determination device 1c according to the embodiment includes the cross-sectional image acquisition unit 10c, a calculation unit (in this example, the fibrosis amount calculation unit 12c), and the cancer progress determination unit 13c.

The cross-sectional image acquisition unit 10c acquires cross-sectional images (in this example, the SHG images PSic) of the uterine epithelial tissue of the examinee.

The calculation unit (in this example, the fibrosis amount calculation unit 12c) calculates an amount of fiber-like structure imaged in the cross-sectional image (in this example, the SHG image PSic) acquired by the cross-sectional image acquisition unit 10c.

The cancer progress determination unit 13c determines progress (in this example, a non-cancer, a precancer, or an invasive cancer) of the uterine cancer of the examinee based on the amount of fiber-like structure calculated by the calculation unit (in this example, the fibrosis amount calculation unit 12c).

In this configuration, the cancer progress determination device 1c according to the embodiment can determine the progress (in this example, a non-cancer, a precancer, or an invasive cancer) of the uterine cancer of the examinee based on the amount of fiber-like structure imaged in the cross-sectional image (in this example, the SHG image PSic) of the uterine epithelial tissue of the examinee. Therefore, it is possible to determine the progress (in this example, a non-cancer, a precancer, or an invasive cancer) of the uterine cancer without dyeing the uterine tissue.

The cancer progress determination device 1c according to the embodiment includes an extraction unit (in this example, the fiber pixel extraction unit 11c).

The extraction unit (in this example, the fiber pixel extraction unit 11c) extracts the fiber pixels which are pixels in which the fiber-like structure is imaged among the pixels of the cross-sectional image (in this example, the SHG image PSic) based on the cross-sectional image (in this example, the SHG image PSic) acquired by the cross-sectional image acquisition unit 10c and a predetermined reference (in this example, the reference generated through the machine learning).

The calculation unit (in this example, the fibrosis amount calculation unit 12c) calculates the amount of fiber-like structure imaged in the cross-sectional image (in this example, the SHG image PSic) based on the fiber pixels extracted by the extraction unit (in this example, the fiber pixel extraction unit 11c).

In this configuration, the cancer progress determination device 1c according to the embodiment can extract the fiber pixels which are the pixels in which the fiber-like structure is imaged among the pixels of the cross-sectional image (in this example, the SHG image PSic). Therefore, it is possible to reduce time and effort for extracting the fiber pixels among the pixels of the cross-sectional image (in this example, the SHG image PSic).

In the cancer progress determination device 1c according to the embodiment, the calculation unit (in this example, the fibrosis amount calculation unit 12c) calculates the area of the fiber-like structure imaged in the cross-sectional image (in this example, the SHG image PSic) as the amount of fiber-like structure.

In this configuration, the cancer progress determination device 1c according to the embodiment can calculate the area of the fiber-like structure imaged in the cross-sectional image (in this example, the SHG image PSic) as the amount of fiber-like structure. Therefore, it is possible to determine the progress (in this example, a non-cancer, a precancer, or an invasive cancer) of the uterine cancer based on the area of the fiber-like structure imaged in the cross-sectional image (in this example, the SHG image PSic) without dyeing the uterine tissue.

In the cancer progress determination device 1c according to the embodiment, the cross-sectional image (in this example, the SHG image PSic) is the second harmonic generation image obtained by the multiphoton microscope 2c.

In this configuration, in the cancer progress determination device 1c according to the embodiment, the cross-sectional image (in this example, the SHG image PSic) in which the fiber-like structure occurring in development of a tumor is imaged using the second harmonic generation can be used. Therefore, it is possible to determine the progress (in this example, a non-cancer, a precancer, or an invasive cancer) of the uterine cancer using the fiber-like structure imaged based on the second harmonic generation without dyeing the uterine tissue.

It is possible to determine the progress without dyeing the uterine tissue.

In the cancer progress determination device 1c according to the embodiment, the cross-sectional images (in this example, the SHG images PSic) are a plurality of cross-sectional images (in this example, the Z stack SHG images ZS1c) imaged at a plurality of depths of the uterine epithelial tissue of the examinee. The calculation unit (in this example, the fibrosis amount calculation unit 12c) calculates the total amount or the average amount of the fiber-like structures imaged in the plurality of cross-sectional images (in this example, the Z stack SHG images ZS1c) or the ratio of the number of pixels of the fiber-like structures to the number of pixels of the cross-sectional images.

In this configuration, the cancer progress determination device 1c according to the embodiment can determine the progress (in this example, a non-cancer, a precancer, or an invasive cancer) of the uterine cancer based on the total amount or the average amount of the fiber-like structures imaged in the plurality of cross-sectional images (in this example, the Z stack SHG images ZS1c) or of the number of pixels of the fiber-like structures to the number of pixels of the cross-sectional images. Therefore, it is possible to inhibit deterioration in the determination accuracy of the progress (in this example, a non-cancer, a precancer, or an invasive cancer) of the uterine cancer when there is a variation in the amount of fiber-like structure among the plurality of cross-sectional images (in this example, the Z stack SHG images ZS1c).

In the cancer progress determination device 1c according to the embodiment, the cancer progress determination unit 13c determines which is applied among the following as the progress of the uterine cancer:

(A) a precancer;
(B) an invasive cancer;
(C) mild dysplasia (CIN1), intermediate dysplasia (CIN2), or severe dysplasia carcinoma in situ (CIN3);
(D) a microinvasive squamous cell carcinoma or a squamous cell carcinoma; and
(E) a cancer for which treatment is necessary or a cancer for which treatment is not necessary.

In this configuration, the cancer progress determination device 1c according to the embodiment can determine which is applied among the above-described items (A) to (E) as the progress of the uterine cancer based on the amount of fiber-like structure in the cross-sectional image (in this example, the SHG image PSic). Therefore, it is possible to determine which is applied among the above-described items (A) to (E) as the progress of the uterine cancer without dyeing the uterine tissue.

In the cancer progress determination device 1c according to the embodiment, the cancer progress determination unit 13c determines that the uterine epithelial tissue is a non-cancer tissue when the amount of fiber-like structure is equal to or less than the first threshold TH1c. When the amount of fiber-like structure exceeds the first threshold TH1c, the cancer progress determination unit 13c determines that the examinee is infected or highly likely to be infected with the uterine cancer.

In this configuration, in the cancer progress determination device 1c according to the embodiment, based on the amount of fiber-like structure in the cross-sectional image (in this example, the SHG image PSic), it is possible to determine whether the uterine tissue is a non-cancer tissue as the progress of the uterine cancer or the examinee is infected or highly likely to be infected with the uterine cancer.

In the cancer progress determination device 1c according to the embodiment, the cross-sectional image is an image of a precancer or an invasive cancer. When the amount of fiber-like structure exceeds the first threshold TH1c and is equal to or less than the second threshold TH2c greater than the first threshold TH1c, the cancer progress determination unit 13c determines that the examinee is infected with the precancer as the progress of the uterine cancer. When the amount of fiber-like structure exceeds the second threshold TH2c, the cancer progress determination unit 13c determines that the examinee is infected with the invasive cancer.

In this configuration, the cancer progress determination device 1c according to the embodiment can determine whether the examinee gets the precancer or the invasive cancer as the progress of the uterine cancer based on the amount of fiber-like structure in the cross-sectional image (in this example, the SHG image PSic).

In the cancer progress determination device 1c according to the embodiment, the cross-sectional image is a cross-sectional image of a precancer or an invasive cancer. When the progress of the uterine cancer of the examinee is the precancer or the invasive cancer and the amount of fiber-like structure is less than the first threshold TH1c, the cancer progress determination unit 13c determines that the progress of the uterine cancer of the examinee is the precancer. When the amount of fiber-like structure exceeds the first threshold TH1c, the cancer progress determination unit 13c determines that the progress of the uterine cancer of the examinee is the invasive cancer.

In this configuration, the cancer progress determination device according to the embodiment can determine the precancer with high accuracy by performing the determination from the images which are the cross-sectional images (the Z stack SHG images ZS1c), the cross-sectional images of the precancer or the invasive cancer, which are the images in which the uterine epithelial tissue of the examinee is the precancer or the invasive cancer.

Parts of the uterine cancer determination devices 1, 1a, and 1b and the cancer progress determination device 1c according to the above-described embodiments, for example, the nucleus region image generation unit 10, the feature amount processing unit 11, the data division unit 12, the classification model generation unit 13, the cancer tissue determination unit 14, the output unit 15, the manipulation input unit 16, the nucleus region image generation unit 10a, the SHG image acquisition unit 18b, the cancer progress determination unit 19b, the cross-sectional image acquisition unit 10c, the fiber pixel extraction unit 11c, the fibrosis amount calculation unit 12c, the cancer progress determination unit 13c, and the output unit 14c may be implemented by a computer. In this case, a program implementing the control function may be recorded on a computer-readable recording medium and the program recorded on the recording medium may be caused to be read and executed in a computer system for the implementation. The "computer system" mentioned here is a computer system embedded in the uterine cancer determination devices 1, 1a, or 1b or the cancer progress determination device 1c and includes an OS or hardware such as a peripheral device. The "computer-readable recording medium" is a portable medium such as a flexible disc, a magneto-optical disc, a ROM, or a CD-ROM or a storage device such as a hard disk embedded in a computer system. Further, the "computer-readable recording medium" may include a line that retains a program in a short time or dynamically, such as a communication line in a case in which a program is transmitted via a network such as the Internet or a telephone line, and a medium that retains a program for a given time, such as an internal volatile memory of a computer system serving as a server or a client in this case. The program may be a program that implements some of the above-described functions or may be a program that can be implemented in combination with a program in which the above-described functions have already been recorded on a computer system.

Some or all of the uterine cancer determination devices 1, 1a, and 1b and the cancer progress determination device 1c according to the above-described embodiments may be implemented as integrated circuits such as large-scale integration (LSI) circuits. Each functional block of the uterine cancer determination devices 1, 1a, and 1b and the cancer progress determination device 1c may be realized as an individual processor or some or all of the uterine cancer determination devices 1, 1a, and 1b and the cancer progress determination device 1c may be integrated as a processor. The scheme for the integrated circuits is not limited to LSI and may be implemented with a dedicated circuit or a general-purpose process. When a circuit integration technology substituting LSI emerges with advance of semiconductor technologies, an integrated circuit by the technology may be used.

The embodiments of the present invention have been described above in detail with reference to the drawings, but specific configurations are not limited to the above-described configurations and various design changes or the like can be made within the scope of the present invention without departing from the gist of the present invention.

REFERENCE SIGNS LIST 1, 1a, 1b Uterine cancer determination device
100 THG image acquisition unit
14 Cancer tissue determination unit
ZT1 Z stack THG image
1c Cancer progress determination device
10c Cross-sectional image acquisition unit
11c Fiber pixel extraction unit
12c Fibrosis amount calculation unit
13c Cancer progress determination unit
PSic SHG image
ZS1c Z stack SHG image

What is claimed is:

1. A cancer determination device comprising:
an irradiation unit configured to irradiate an undyed uterine tissue with excitation light;
a third harmonic image acquisition unit configured to acquire a third harmonic image of the uterine tissue based on light generated in third harmonic generation caused by interaction between the uterine tissue and the excitation light;
a cancer tissue determination unit configured to determine a likelihood that the uterine tissue is a cancer tissue based on a state of a cell nucleus in the third harmonic image;
a second harmonic image acquisition unit configured to acquire second harmonic images based on light generated in second harmonic generation caused by the interaction between the uterine tissue and the excitation light; and
a cancer progress determination unit configured to determine cancer progress based on states of fiber-like structures in the second harmonic images when the cancer tissue determination unit determines that the likelihood that the uterine tissue is a cancer tissue is high, wherein
each of the second harmonic images and the third harmonic images are a plurality of cross-sectional images captured at a plurality of depths of the uterine tissue in a direction oriented inward from an epithelial tissue of the uterine tissue,
the depth is common to the second harmonic image and the third harmonic image,
the cancer tissue determination unit performs a first determination process wherein the first determination process determines, based on feature amounts of the cell nucleus which are extracted from the third harmonic image and are according to the depth, whether the uterine tissue is a cancer tissue or a normal tissue, and
the cancer progress determination unit performs a second determination process wherein the second determination process determines, based on an amount of the fiber-like structures imaged in the second harmonic images which is according to the depth, whether the uterine tissue which is determined as a cancer tissue in the first determination process is a precancer or an invasive cancer.

2. The cancer determination device according to claim 1, wherein a state of the cell nucleus is at least one selected from a group formed of areas of cell nuclei, densities of the cell nuclei, and shapes of the cell nuclei.

3. The cancer determination device according to claim 2, wherein the cancer tissue determination unit determines that a likelihood that the tissue is a cancer tissue is high when at least one of following features is satisfied:
(i) an average of the areas of the cell nuclei is larger than in normal tissues;
(ii) a variation in the areas of the cell nuclei is greater than in normal tissues;
(iii) density of the cell nuclei is higher than in normal tissues;
(iv) a variation in the density of the cell nuclei is greater than in normal tissues;
(v) distortion of the shapes of the cell nuclei is greater than in normal tissues; and
(vi) a variation in the shapes of the cell nuclei is greater than in normal tissues.

4. The cancer determination device according to claim 1, wherein the cancer tissue determination unit determines a likelihood that the tissue is a cancer tissue based on the state of the cell nucleus in the third harmonic image with reference to a classification model learned using learning third harmonic images of normal tissues and/or learning third harmonic images of cancer tissues.

5. The cancer determination device according to claim 4, wherein the learning third harmonic images are a plurality of cross-sectional images of an epithelial tissue.

6. The cancer determination device according to claim 4 wherein the third harmonic images are a plurality of cross-sectional images of an epithelial tissue.

7. The cancer determination device according to claim 6, wherein the cancer tissue determination unit determines a likelihood that the tissue is a cancer tissue in each of the plurality of third harmonic images and calculates a likelihood that the tissue is a cancer tissue based on a ratio of the third harmonic images in which the likelihood that the tissue is determined to be a cancer tissue is high to all the third harmonic images.

8. The cancer determination device according to claim 1, wherein the cancer progress determination unit determines which is applied among the following as the cancer progress:
  (A) a precancer;
  (B) an invasive cancer;
  (C) mild dysplasia (CIN1), intermediate dysplasia (CIN2), or severe dysplasia carcinoma in situ (CIN3);
  (D) a microinvasive squamous cell carcinoma or a squamous cell carcinoma; and
  (E) a cancer for which treatment is necessary or a cancer for which treatment is not necessary.

9. The cancer determination device according to claim 1, further comprising:
  a calculation unit configured to calculate an amount of the fiber-like structure imaged in the second harmonic image acquired by the second harmonic image acquisition unit,
  wherein the state of the fiber-like structure is determined based on the amount of the fiber-like structure calculated by the calculation unit.

10. The cancer determination device according to claim 9, further comprising:
  an extraction unit configured to extract fiber pixels which are pixels in which the fiber-like structure is imaged among pixels of the second harmonic image based on the second harmonic image and a predetermined reference,
  wherein the calculation unit calculates the amount of the fiber-like structure based on the fiber pixels extracted by the extraction unit.

11. The cancer determination device according to claim 9, wherein the calculation unit calculates an area of the fiber-like structure imaged in the second harmonic image as the amount of the fiber-like structure.

12. The cancer determination device according to claim 9, wherein the calculation unit calculates a total amount or an average amount of the fiber-like structures imaged in the plurality of cross-sectional images or a ratio of the number of pixels of the fiber-like structure to the number of whole pixels of the cross-sectional images.

13. The cancer determination device according to claim 9, wherein the cancer progress determination unit determines the cancer progress as precancer when the amount of the fiber-like structure exceeds a first threshold and is equal to or less than a second threshold greater than the first threshold, and
  wherein the cancer progress determination unit determines the cancer progress as invasive cancer when the amount of the fiber-like structures exceeds the second threshold.

14. The cancer determination device according to claim 9,
  wherein the second harmonic image is a cross-sectional image of the precancer or the invasive cancer,
  wherein the cancer progress determination unit determines the cancer progress as precancer when the amount of the fiber-like structure is equal to or less than a first threshold, and
  wherein the cancer progress determination unit determines the cancer progress as invasive cancer when the amount of the fiber-like structure exceeds the first threshold.

15. A cancer determination method comprising:
  an irradiation step of irradiating an undyed uterine tissue with excitation light;
  a third harmonic image acquisition step of acquiring a third harmonic image of the uterine tissue based on light generated in third harmonic generation caused by interaction between the uterine tissue and the excitation light;
  a cancer tissue determination step of determining a likelihood that the uterine tissue is a cancer tissue based on a state of a cell nucleus in the third harmonic image;
  a second harmonic image acquisition step of acquiring second harmonic images based on light generated in second harmonic generation caused by the interaction between the uterine tissue and the excitation light; and
  a cancer progress determination step of determining cancer progress based on states of fiber-like structures in the second harmonic images when the cancer tissue determination step determines that the likelihood that the uterine tissue is a cancer tissue is high, wherein
  each of the second harmonic images and the third harmonic images are a plurality of cross-sectional images captured at a plurality of depths of the uterine tissue in a direction oriented inward from an epithelial tissue of the uterine tissue,
  the depth is common to the second harmonic image and the third harmonic image,
  the cancer tissue determination step performs a first determination process wherein the first determination process determines, based on feature amounts of the cell nucleus which are extracted from the third harmonic image and are according to the depth, whether the uterine tissue is a cancer tissue or a normal tissue, and
  the cancer progress determination step performs a second determination process wherein the second determination process determines, based on an amount of the fiber-like structures imaged in the second harmonic images which is according to the depth, whether the uterine tissue which is determined as a cancer tissue in the first determination process is a precancer or an invasive cancer.

16. A computer-readable non-transitory medium storing instructions which, when executed by a computer, cause the computer to execute:
  an irradiation step of irradiating an undyed uterine tissue with excitation light;
  a third harmonic image acquisition step of acquiring a third harmonic image of the uterine tissue based on light generated in third harmonic generation caused by interaction between the uterine tissue and the excitation light;
  a cancer tissue determination step of determining a likelihood that the uterine tissue is a cancer tissue based on a state of a cell nucleus in the third harmonic image;

a second harmonic image acquisition step of acquiring second harmonic images based on light generated in second harmonic generation caused by the interaction between the uterine tissue and the excitation light; and a cancer progress determination step of determining cancer progress based on states of fiber-like structures in the second harmonic images when the cancer tissue determination step determines that the likelihood that the uterine tissue is a cancer tissue is high, wherein each of the second harmonic images and the third harmonic images are a plurality of cross-sectional images captured at a plurality of depths of the uterine tissue in a direction oriented inward from an epithelial tissue of the uterine tissue, the depth is common to the second harmonic image and the third harmonic image, the cancer tissue determination step performs a first determination process wherein the first determination process determines, based on feature amounts of the cell nucleus which are extracted from the third harmonic image and are according to the depth, whether the uterine tissue is a cancer tissue or a normal tissue, and the cancer progress determination step performs a second determination process wherein the second determination process determines, based on an amount of the fiber-like structures imaged in the second harmonic images which is according to the depth, whether the uterine tissue which is determined as a cancer tissue in the first determination process is a precancer or an invasive cancer.

* * * * *